United States Patent [19]

Makarow

[11] Patent Number: 5,677,172
[45] Date of Patent: Oct. 14, 1997

[54] METHOD FOR PRODUCTION OF PROTEINS IN YEAST

[76] Inventor: Marja Makarow, Nervanderinkatu 12 A 8, FIN-00100 Helsinki, Finland

[21] Appl. No.: 295,676

[22] PCT Filed: Mar. 11, 1993

[86] PCT No.: PCT/FI93/00088

§ 371 Date: Sep. 9, 1994

§ 102(e) Date: Sep. 9, 1994

[87] PCT Pub. No.: WO93/18167

PCT Pub. Date: Sep. 16, 1993

[30] Foreign Application Priority Data

Mar. 11, 1992 [FI] Finland ................... 921059

[51] Int. Cl.$^6$ .................... C07H 21/04; C12N 15/63; C12N 15/00; C12P 21/00
[52] U.S. Cl. .................. 435/320.1; 536/23.1; 536/23.4; 435/69.7; 435/69.9; 435/71.1; 435/255; 435/320.1
[58] Field of Search ................... 536/23.1, 23.4; 435/69.7, 69.9, 71.1, 255, 320.1

[56] References Cited

U.S. PATENT DOCUMENTS

| 4,797,359 | 1/1989 | Finkelstein | 435/69.1 |
| 4,914,026 | 4/1990 | Brake et al. | 435/91.4 |

FOREIGN PATENT DOCUMENTS

| 0220689 | 5/1987 | European Pat. Off. |
| 89/08661 | 9/1989 | WIPO |
| 90/10075 | 9/1990 | WIPO |
| 92/11378 | 7/1992 | WIPO |

OTHER PUBLICATIONS

Nevalainen, "Membrane Traffic in Mitotic and Interphase Yeast Cells", Doctoral thesis, Univ. of Helsinki, pp. 1–61 (1991).
Makarow et al, Proc. Natl. Acad. Sci. USA, vol. 83, pp. 8117–8121 (Nov. 1986).
Duran–Torres et al, "A Secretory Heat Shock Protein of Saccharomyces cerevisiae", pp. 1–15.
Nevalainen et al, Eur. J. Biochem., vol. 178, pp. 39–46 (1988).
Nevalainen et al, Eur. J. Biochem., vol. 184, pp. 165–172 (1989).
Makarow et al, The Journal of Cell Biology, vol. 104, pp. 67–75 (Jan. 1987).
Nevalainen et al, "Uptake of Endocytic Markers into Mitotic Yeast Cells", Univ. of Helsinki, pp. 1–6 (1991).
Ruohola, Doctoral thesis, "Biochemical and Genetic . . . in Yeast", Univ. of Helsinki, Abstract (1989).
Brake et al, Proc. Natl. Acad. Sci. USA, vol. 81, pp.4642–4646 (Aug. 1984).
Lupashin et al, Dokl. Akad. Nauk SSSR, 317(5), pp. 1257–1260 (1991).
Simonen et al, "Journal of Biological Chemistry" vol. 269, No. pp. 1–7 (1994).
Jamsa et al "Yeast" vol. 10, pp. 355–370 (1994).
Russo et al, "Proc. Natl. Acad. Sci. USA" vol. 89, pp. 3671–3675 (1992).

Primary Examiner—George G. Elliott
Assistant Examiner—Andrew Wang
Attorney, Agent, or Firm—Birch, Stewart, Kolasch & Birch, LLP

[57] ABSTRACT

The present invention concerns the production of useful proteins on the growth medium of yeast by using the hsp150 protein or fragments or derivatives thereof as a carrier. The authentic hsp150 protein, encoded by the hsp150 gene of Saccharomyces cerevisiae, is secreted efficiently to the growth medium. In the new recombinant DNA vectors the gene encoding the desired protein is joined to the hsp150 nucleotide sequence. The fusion gene is transformed to a yeast host to express the respective fusion protein. The signal sequence of the hsp150 protein, or another sequence, guides the fusion protein to the secretory pathway, and the hsp150-carrier takes it to the medium, from where it is harvested. During the secretion protein, the protein product may or may not be detached from the hsp150 carrier by proteolytic enzymes, according to the occurrence or created cleavage sites at carrier-product junction.

21 Claims, 37 Drawing Sheets

FIGURE 1A

```
        AGTGATCTTACTATTCCTATTCGGAAATTATTAAAGACAAAAAGCTCATTAATGGCTTTCCGTCTGTAGTGATAAGTCGCCAACTCA
-396
                                              **    ****              *
        GCCTAAATTTTCATTTCTTTACCAGATCAGAAAACTAATAGTACAAATGAGTGTTTTCTCAAGCGGAACACCACATTTGAGCTAAATT
-306
                                    ***    **          ***    *
        TAGATTTTGGTCAAAATAAGAAAGATCCTAAAAAAGGAATGGTTGGTGAAAAATTTATTAGCTTGAATGGTAGGAATCCTCGAGA TATAA
-216
                ***                **                                              ***
        AAGGAACACTTGAAGTCTAACGACAATCAATTTCGATTATGTCCTTCCTTTTACCTCAAAGCTCAAAAAATATCAATAAGAAACTCATA
-126
                        ***   *  **
        TTCCTTTTCTAACCCTAGTACAATAATAATATA ATG CAA TAC AAA AAG ACT TTG GTT GCC TCT GCT TTG GCC GCT
-36                                       Met Gln Tyr Lys Lys Thr Leu Val Ala Ser Ala Leu Ala Ala

ACT ACA TTG GCC▼GCC TAT GCT CCA TCT GAG CCT TGG TCC ACT TTG ACT CCA ACA GCC ACT TAC AGC GGT GGT
+43     Thr Thr Leu Ala Ala Tyr Ala Pro Ser Glu Pro Trp Ser Thr Leu Thr Pro Thr Ala Thr Tyr Ser Gly Gly
+15           1

GTT ACC GAC TAC GCT TCC ACC TTC GGT ATT GCC GTT CAA CCA ATC TCC ACT ACA TCC AGC GCA TCA TCT GCA
+115    Val Thr Asp Tyr Ala Ser Thr Phe Gly Ile Ala Val Gln Pro Ile Ser Thr Thr Ser Ser Ala Ser Ser Ala
+39

GCC ACC ACA GCC TCA TCT AAG GCC AAG AGA ACT GCT TCC CAA ATT GGT GAT GGT CAA GTC CAA GCT GCT ACC
+187    Ala Thr Thr Ala Ser Ser Lys Ala Lys Arg Ala Ala Ser Gln Ile Gly Asp Gly Gln Val Gln Ala Ala Thr
+63                                         2

ACT ACT GCT TCT GTC TCT ACC AAG AGT ACC GCT GCC GCC GTT TCT CAG ATC GGT GAT GGT ATC CAA GCT
+259    Thr Thr Ala Ser Val Ser Thr Lys Ser Thr Ala Ala Ala Val Ser Gln Ile Gly Asp Gly Ile Gln Ala
+87
```

FIGURE 1B

```
+331  ACT ACT AAG ACT ACC GCT GCT GTC TCT CAA ATT GGT GAT GGT CAA ATT CAA GCT ACC AAG ACT ACC
+111  Thr Thr Lys3Thr Thr Ala Ala Val Ser Gln Ile Gly Asp Gly Gln Ile Gln Ala Thr Lys Thr Thr

+403  TCT GCT AAG ACT ACC GCC GCT GCT TCT CAA ATC AGT GAT GGT CAA ATC CAA GCT ACC ACC ACT TTA
+135  Ser Ala Lys Thr Thr Ala Ala Ala Ser Gln Ile Ser Asp Gly Gln Ile Gln Ala Thr Thr Thr Leu

+475  GCC CCA AAG AGC ACC GCT GCT GCT TCT CAA ATC GGT GAT GGT CAA ATC CAA GTT ACC ACC ACT TTA
+159  Ala Pro Lys Ser Thr Ala Ala Ala Ser Gln Ile Gly Asp Gly Gln Ile Gln Val Thr Thr Thr Leu

+547  GCC CCA AAG AGC ACC GCT GCT GCT TCT CAA ATC GGT GAT GGT CAA ATC CAA GTT ACC AAG ACT ACC
+183  Ala Pro Lys Ser Thr Ala Ala Ala Ser Gln Ile Gly Asp Gly Gln Ile Gln Val Thr Lys Thr Thr

+619  GCT GCT GTC TTT CAA ATT GGT GAT GGT CAA GTT CTT GCT ACC ACC ACT CGT GCC GCC GTT TCT
+207  Ala Ala Val Phe Gln Ile Gly Asp Gly Gln Val Leu Ala Thr Thr Thr Arg Ala Ala Val Ser

+691  CAA ATC GGT GAT GGT CAA GTT CAA GCT ACC AAG ACT GCT GTC TCT CAA ATC GGT GAT GGT
+231  Gln Ile Gly Asp Gly Gln Val Gln Ala Thr Lys4Thr Thr Ala Ala Val Ser Gln Ile Gly Asp Gly

+763  CAA GTT CAA GCA ACT ACC AAA ACC GCC GCA GTA AGC GAT GGC CAA GTC CAA GTT CAA GCC ACT
+255  Gln Val Gln Ala Thr Thr Lys Thr Ala Ala Val Ser Asp Gly Gln Val Gln Val Gln Ala Thr

+835  ACA AAA ACT ACT CAA GCA GCC AGC GCC GAT GGC CAA GTC CAA GTC ACT ACT GCT ACT TCC GCT TCT
+279  Thr Lys Thr Thr Gln Ala Ala Ser Ala Asp Gly Gln Val Gln Val Thr Thr Ala Thr Ser Ala Ser

+907  GCA GCC GCT ACC TCC ACT GAC CCA GTC GAT GCT GTC TCC TGT AAG ACT TCT GGT ACC TTA GAA ATG AAC TTA
+303  Ala Ala Ala Thr Ser Thr Asp Pro Val Asp Ala Val Ser Cys Lys Thr Ser Gly Thr Leu Glu Met Asn Leu
```

FIGURE 1C

```
+979   AAG GGC GGT ATC TTA ACT GAC GGT AAG GGT AGA ATT GTT GCT AAC AGA CAA TTC CAA TTT GAC
+327   Lys Gly Gly Ile Leu Thr Asp Gly Lys Gly Arg Ile Val Ala Asn Arg Gln Phe Gln Phe Asp

+1051  GGT CCA CCA CAA GCT GGT GCC ATC TAC GCT GGT TGG TCT ATA ACT CCA GAC GGT AAC TTG GCT ATT
+351   Gly Pro Pro Gln Ala Gly Ala Ile Tyr Ala Gly Trp₆Ser Ile Thr Pro Asp Gly Asn Leu Ala Ile

+1123  GGT GAC AAT GAT GTC TTC TAC CAA TGT TTG TCC GGT ACT TTC TAC AAC TTG TAC GAC GAA CAC ATT GGT AGT
+375   Gly Asp Asn Asp Val Phe Tyr Gln Cys Leu Ser Gly Thr Phe Tyr Asn₇Leu Tyr Asp Glu His Ile Gly Ser

+1195  CAA TGT ACT CCA GTC CAC TTG GAA GCT ATC GAT TTG ATA GAC TGT TAAGCAGAAAACTATTAGTTCTTTTATCCT
+399   Gln Cys Thr Pro Val His Leu Glu Ala Ile Asp Leu Ile Asp Cys

+1270  AGAAGTGTCCTTTTCTACTACTACTCTAGTCGCATCCATTCCTTTGCATTTATCTTTTCTGATGACTTTTTCTCATTGCATTGATTAGA

+1360  AAGGAAAAAAGCGGTTGGCCAATCCATTCTTCCGAGAATTGGCTAGCCATATACTTGATGTTTTCCCATTATTGGTTCGTTGCAATGCT

+1450  AATTTTCTTAATTGCCCCTTATATACTCTTCCATAAAATGTTTTTTTATAACTAATAATTTTCTGTATATCATTATCTAATAATCTTATAAA

+1540  ATGTTAAAAGACTTGGAAAGCAACGAGTGATCGTGACCACATAATTGCCTCGCTACACGGCAAAAATAAGCCAGTCCTAATGTGTATAT

+1630  TAAAGGCTGCATGTGGCTACGTC
```

```
 73--AA-SQIGDGQVQAATTT 88
 96TAAAVSQIGDGQIQATTKT114
115TAAAVSQIGDGQIQATTKT133
139TAAAVSQISDGQIQATTTT157
163TAAAVSQIGDGQVQATTTT181
187TAAAVSQIGDGQVQATTKT205
206TAAAVFQIGDGQVLATTKT224
225TRAAVSQIGDGQVQATTKT243
244TAAAVSQIGDGQVQATTKT262
263TAAAVSQITDGQVQATTKT281
282TQAA-SQVSDGQVQATTAT299
```

FIG. 3A FIG. 3B FIG. 3C FIG. 3D
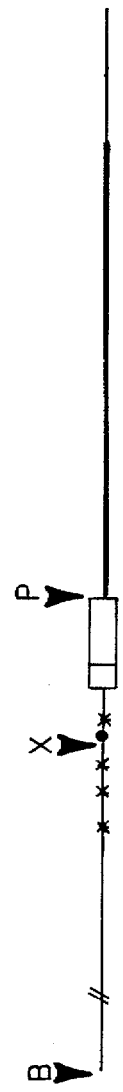

SEQUENCE LISTING ( 1 ) GENERAL INFORMATION:

( i i i ) NUMBER OF SEQUENCES: 21

( 2 ) INFORMATION FOR SEQ ID NO: 1:

( i ) SEQUENCE CHARACTERISTICS:
        ( A ) LENGTH: 2048 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Saccharomyces cerevisiae ( i x ) FEATURE:
        ( A ) NAME/KEY: CDS
        ( B ) LOCATION: 397..1638

( i x ) FEATURE:
        ( A ) NAME/KEY: sig_peptide
        ( B ) LOCATION: 397..450

( i x ) FEATURE:
        ( A ) NAME/KEY: mat_peptide
        ( B ) LOCATION: 451..1638

( i x ) FEATURE:
        ( A ) NAME/KEY: misc_feature
        ( B ) LOCATION: 115..128
        ( D ) OTHER INFORMATION: /note= "(HSE) Heat promoter-like
            sequence"

( i x ) FEATURE:
        ( A ) NAME/KEY: misc_feature
        ( B ) LOCATION: 200..212
        ( D ) OTHER INFORMATION: /note= "(HSE) Heat promoter-like
            sequence"

( i x ) FEATURE:
        ( A ) NAME/KEY: misc_feature
        ( B ) LOCATION: 223..235
        ( D ) OTHER INFORMATION: /note= "(HSE) Heat promoter-like
            sequence"

( i x ) FEATURE:
        ( A ) NAME/KEY: misc_feature
        ( B ) LOCATION: 282..294
        ( D ) OTHER INFORMATION: /note= "(HSE) Heat promoter-like
            sequence"

( i x ) FEATURE:
        ( A ) NAME/KEY: misc_feature
        ( B ) LOCATION: 266..270
        ( D ) OTHER INFORMATION: /note= "TATA-sequence"

( i x ) FEATURE:
        ( A ) NAME/KEY: misc_feature
        ( B ) LOCATION: 613..1293
        ( D ) OTHER INFORMATION: /note= "Repetitive sequence"

( x i ) SEQUENCE DESCRIPTION: SEQ ID NO: 1:

```
AGTGATCTTA   CTATTTCCTA   TTTCGGAAAT   TATTAAAGAC   AAAAAGCTC   ATTAATGGCT        60

TTCCGTCTGT   AGTGATAAGT   CGCCAACTCA   GCCTAATTTT   TCATTTCTTT   ACCAGATCAG      120

GAAAACTAAT   AGTACAAATG   AGTGTTTTCT   CAAGCGGAAC   ACCACATTTT   GAGCTAAATT      180
```

-continued

| | | | | | |
|---|---|---|---|---|---|
| TAGATTTTGG | TCAAAATAAG | AAAGATCCTA | AAAAAGGAAT | GGTTGGTGAA | AAATTTATTA | 240 |
| GCTTGAATGG | TAGGAATCCT | CGAGATATAA | AAGGAACACT | TGAAGTCTAA | CGACAATCAA | 300 |
| TTTCGATTAT | GTCCTTCCTT | TTACCTCAAA | GCTCAAAAAA | ATATCAATAA | GAAACTCATA | 360 |
| TTCCTTTTCT | AACCCTAGTA | CAATAATAAT | AATATA ATG | CAA TAC AAA | AAG ACT | 414 |
| | | | Met Gln -18 | Tyr Lys -15 | Lys Thr | |

```
TTG GTT GCC TCT GCT TTG GCC GCT ACT ACA TTG GCC GCC TAT GCT CCA         462
Leu Val Ala Ser Ala Leu Ala Ala Thr Thr Leu Ala Ala Tyr Ala Pro
        -10              -5                        1

TCT GAG CCT TGG TCC ACT TTG ACT CCA ACA GCC ACT TAC AGC GGT GGT         510
Ser Glu Pro Trp Ser Thr Leu Thr Pro Thr Ala Thr Tyr Ser Gly Gly
 5              10                  15                      20

GTT ACC GAC TAC GCT TCC ACC TTC GGT ATT GCC GTT CAA CCA ATC TCC         558
Val Thr Asp Tyr Ala Ser Thr Phe Gly Ile Ala Val Gln Pro Ile Ser
                25                  30                      35

ACT ACA TCC AGC GCA TCA TCT GCA GCC ACC ACA GCC TCA TCT AAG GCC         606
Thr Thr Ser Ser Ala Ser Ser Ala Ala Thr Thr Ala Ser Ser Lys Ala
            40                  45                  50

AAG AGA GCT GCT TCC CAA ATT GGT GAT GGT CAA GTC CAA GCT GCT ACC         654
Lys Arg Ala Ala Ser Gln Ile Gly Asp Gly Gln Val Gln Ala Ala Thr
        55                  60                  65

ACT ACT GCT TCT GTC TCT ACC AAG AGT ACC GCT GCC GCC GTT TCT CAG         702
Thr Thr Ala Ser Val Ser Thr Lys Ser Thr Ala Ala Ala Val Ser Gln
 70                 75                  80

ATC GGT GAT GGT CAA ATC CAA GCT ACT ACT AAG ACT ACC GCT GCT GCT         750
Ile Gly Asp Gly Gln Ile Gln Ala Thr Thr Lys Thr Thr Ala Ala Ala
 85                 90                  95                  100

GTC TCT CAA ATT GGT GAT GGT CAA ATT CAA GCT ACC ACC AAG ACT ACC         798
Val Ser Gln Ile Gly Asp Gly Gln Ile Gln Ala Thr Thr Lys Thr Thr
            105                 110                 115

TCT GCT AAG ACT ACC GCC GCT GCC GTT TCT CAA ATC AGT GAT GGT CAA         846
Ser Ala Lys Thr Thr Ala Ala Ala Val Ser Gln Ile Ser Asp Gly Gln
            120                 125                 130

ATC CAA GCT ACC ACC ACT ACT TTA GCC CCA AAG AGC ACC GCT GCT GCC         894
Ile Gln Ala Thr Thr Thr Thr Leu Ala Pro Lys Ser Thr Ala Ala Ala
        135                 140                 145

GTT TCT CAA ATT GGT GAT GGT CAA GTT CAA GCT ACC ACC ACT ACT TTA         942
Val Ser Gln Ile Gly Asp Gly Gln Val Gln Ala Thr Thr Thr Thr Leu
150                 155                 160

GCC CCA AAG AGC ACC GCT GCT GCC GTT TCT CAA ATC GGT GAT GGT CAA         990
Ala Pro Lys Ser Thr Ala Ala Ala Val Ser Gln Ile Gly Asp Gly Gln
165                 170                 175                 180

GTT CAA GCT ACT ACT AAG ACT ACC GCT GCT GCT GTC TTT CAA ATT GGT        1038
Val Gln Ala Thr Thr Lys Thr Thr Ala Ala Ala Val Phe Gln Ile Gly
            185                 190                 195

GAT GGT CAA GTT CTT GCT ACC ACC AAG ACT ACT CGT GCC GCC GTT TCT        1086
Asp Gly Gln Val Leu Ala Thr Thr Lys Thr Thr Arg Ala Ala Val Ser
            200                 205                 210

CAA ATC GGT GAT GGT CAA GTT CAA GCT ACT ACC AAG ACT ACC GCT GCT        1134
Gln Ile Gly Asp Gly Gln Val Gln Ala Thr Thr Lys Thr Thr Ala Ala
        215                 220                 225

GCT GTC TCT CAA ATT GGT GAT GGT CAA GTT CAA GCA ACT ACC AAA ACC        1182
Ala Val Ser Gln Ile Gly Asp Gly Gln Val Gln Ala Thr Thr Lys Thr
        230                 235                 240

ACT GCC GCA GCT GTT TCC CAA ATT ACT GAC GGT CAA GTT CAA GCC ACT        1230
Thr Ala Ala Ala Val Ser Gln Ile Thr Asp Gly Gln Val Gln Ala Thr
245                 250                 255                 260

ACA AAA ACC ACT CAA GCA GCC AGC CAA GTA AGC GAT GGC CAA GTC CAA        1278
Thr Lys Thr Thr Gln Ala Ala Ser Gln Val Ser Asp Gly Gln Val Gln
```

```
         265                          270                          275
GCT ACT ACT GCT ACT TCC GCT TCT GCA GCC GCT ACC TCC ACT GAC CCA          1326
Ala Thr Thr Ala Thr Ser Ala Ser Ala Ala Ala Thr Ser Thr Asp Pro
            280                 285                 290

GTC GAT GCT GTC TCC TGT AAG ACT TCT GGT ACC TTA GAA ATG AAC TTA          1374
Val Asp Ala Val Ser Cys Lys Thr Ser Gly Thr Leu Glu Met Asn Leu
            295                 300                 305

AAG GGC GGT ATC TTA ACT GAC GGT AAG GGT AGA ATT GGT TCT ATT GTT          1422
Lys Gly Gly Ile Leu Thr Asp Gly Lys Gly Arg Ile Gly Ser Ile Val
            310                 315                 320

GCT AAC AGA CAA TTC CAA TTT GAC GGT CCA CCA CCA CAA GCT GGT GCC          1470
Ala Asn Arg Gln Phe Gln Phe Asp Gly Pro Pro Pro Gln Ala Gly Ala
325                 330                 335                 340

ATC TAC GCT GCT GGT TGG TCT ATA ACT CCA GAC GGT AAC TTG GCT ATT          1518
Ile Tyr Ala Ala Gly Trp Ser Ile Thr Pro Asp Gly Asn Leu Ala Ile
            345                 350                 355

GGT GAC AAT GAT GTC TTC TAC CAA TGT TTG TCC GGT ACT TTC TAC AAC          1566
Gly Asp Asn Asp Val Phe Tyr Gln Cys Leu Ser Gly Thr Phe Tyr Asn
            360                 365                 370

TTG TAC GAC GAA CAC ATT GGT AGT CAA TGT ACT CCA GTC CAC TTG GAA          1614
Leu Tyr Asp Glu His Ile Gly Ser Gln Cys Thr Pro Val His Leu Glu
            375                 380                 385

GCT ATC GAT TTG ATA GAC TGT TAAGCAGAAA ACTATTAGTT CTTTTATCCT             1665
Ala Ile Asp Leu Ile Asp Cys
            390             395

GATGACTTTT TCTCATTTGC ATTGATTAGA AAGGAAAAAA AGAAGTGTCC TTTTCTACTA        1725
CTACTCTAGT CGCATCCATT CCTTTGCATT TATCTTTTCT GCGGTTGGCC AATCCATTCT        1785
TCCGAGAATT TGGCTAGCCA TACTTGATGT TTTCCCATTA TTGGTTCGTT TGGCAATGCT        1845
AATTTTCTTA ATTGCCCCTT ATATACTCTT CCATAAAATG TTTTTTTTAT AACTAATTTT        1905
CTGTATATCA TTATCTAATA ATCTTATAAA ATGTTAAAAA GACTTGGAAA GCAACGAGTG        1965
ATCGTGACCA CATAATTGCC TCGCTACACG GCAAAAATAA GCCAGTCCTA ATGTGTATAT        2025
TAAAGGCTGC ATGTGGCTAC GTC                                                2048
```

( 2 ) INFORMATION FOR SEQ ID NO: 2:

( i ) SEQUENCE CHARACTERISTICS:
        ( A ) LENGTH: 413 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
Met Gln Tyr Lys Lys Thr Leu Val Ala Ser Ala Leu Ala Ala Thr Thr
-18         -15                 -10                 -5

Leu Ala Ala Tyr Ala Pro Ser Glu Pro Trp Ser Thr Leu Thr Pro Thr
    -1  1                  5                  10

Ala Thr Tyr Ser Gly Gly Val Thr Asp Tyr Ala Ser Thr Phe Gly Ile
15                  20                  25                  30

Ala Val Gln Pro Ile Ser Thr Thr Ser Ser Ala Ser Ala Ala Thr
                35                  40                  45

Thr Ala Ser Ser Lys Ala Lys Arg Ala Ala Ser Gln Ile Gly Asp Gly
            50                  55                  60

Gln Val Gln Ala Ala Thr Thr Thr Ala Ser Val Ser Thr Lys Ser Thr
            65                  70                  75

Ala Ala Ala Val Ser Gln Ile Gly Asp Gly Gln Ile Gln Ala Thr Thr
            80                  85                  90
```

```
Lys  Thr  Thr  Ala  Ala  Ala  Val  Ser  Gln  Ile  Gly  Asp  Gly  Gln  Ile  Gln
 95                      100                     105                      110

Ala  Thr  Thr  Lys  Thr  Thr  Ser  Ala  Lys  Thr  Thr  Ala  Ala  Ala  Val  Ser
               115                     120                          125

Gln  Ile  Ser  Asp  Gly  Gln  Ile  Gln  Ala  Thr  Thr  Thr  Thr  Leu  Ala  Pro
               130                     135                          140

Lys  Ser  Thr  Ala  Ala  Ala  Val  Ser  Gln  Ile  Gly  Asp  Gly  Gln  Val  Gln
          145                     150                     155

Ala  Thr  Thr  Thr  Thr  Leu  Ala  Pro  Lys  Ser  Thr  Ala  Ala  Ala  Val  Ser
          160                     165                     170

Gln  Ile  Gly  Asp  Gly  Gln  Val  Gln  Ala  Thr  Thr  Lys  Thr  Thr  Ala  Ala
175                     180                     185                     190

Ala  Val  Phe  Gln  Ile  Gly  Asp  Gly  Gln  Val  Leu  Ala  Thr  Thr  Lys  Thr
               195                     200                          205

Thr  Arg  Ala  Ala  Val  Ser  Gln  Ile  Gly  Asp  Gly  Gln  Val  Gln  Ala  Thr
               210                     215                     220

Thr  Lys  Thr  Thr  Ala  Ala  Ala  Val  Ser  Gln  Ile  Gly  Asp  Gly  Gln  Val
          225                     230                     235

Gln  Ala  Thr  Thr  Lys  Thr  Thr  Ala  Ala  Ala  Val  Ser  Gln  Ile  Thr  Asp
     240                     245                     250

Gly  Gln  Val  Gln  Ala  Thr  Thr  Lys  Thr  Thr  Gln  Ala  Ala  Ser  Gln  Val
255                     260                     265                     270

Ser  Asp  Gly  Gln  Val  Gln  Ala  Thr  Thr  Ala  Thr  Ser  Ala  Ser  Ala  Ala
               275                     280                     285

Ala  Thr  Ser  Thr  Asp  Pro  Val  Asp  Ala  Val  Ser  Cys  Lys  Thr  Ser  Gly
               290                     295                     300

Thr  Leu  Glu  Met  Asn  Leu  Lys  Gly  Gly  Ile  Leu  Thr  Asp  Gly  Lys  Gly
               305                     310                     315

Arg  Ile  Gly  Ser  Ile  Val  Ala  Asn  Arg  Gln  Phe  Gln  Phe  Asp  Gly  Pro
     320                     325                     330

Pro  Pro  Gln  Ala  Gly  Ala  Ile  Tyr  Ala  Ala  Gly  Trp  Ser  Ile  Thr  Pro
335                     340                     345                     350

Asp  Gly  Asn  Leu  Ala  Ile  Gly  Asp  Asn  Asp  Val  Phe  Tyr  Gln  Cys  Leu
               355                     360                     365

Ser  Gly  Thr  Phe  Tyr  Asn  Leu  Tyr  Asp  Glu  His  Ile  Gly  Ser  Gln  Cys
               370                     375                     380

Thr  Pro  Val  His  Leu  Glu  Ala  Ile  Asp  Leu  Ile  Asp  Cys
               385                     390                     395
```

( 2 ) INFORMATION FOR SEQ ID NO: 3:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: modified_base
        ( B ) LOCATION: one-of(3, 6, 9, 12, 15, 18, 21)
        ( D ) OTHER INFORMATION: /mod_base=i ( i x ) FEATURE:
        ( A ) NAME/KEY: -
        ( B ) LOCATION: 1..38
        ( D ) OTHER INFORMATION: /label=oligonucleotide
        / note= "synthetic oligonucleotide designed for
        screening of HSP150 gene"

( x i ) SEQUENCE DESCRIPTION: SEQ ID NO: 3:

GCNCCNGCNT GNGGNGGNGG NCCRTCRAAY TGRAAYTG                                    38

( 2 ) INFORMATION FOR SEQ ID NO: 4:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 6..12
        ( D ) OTHER INFORMATION: /function="ClaI restriction site"

( i x ) FEATURE:
        ( A ) NAME/KEY: misc_feature
        ( B ) LOCATION: 13..18
        ( D ) OTHER INFORMATION: /function="KpnI restriction site"

( i x ) FEATURE:
        ( A ) NAME/KEY: misc_feature
        ( B ) LOCATION: 18..23
        ( D ) OTHER INFORMATION: /function="PstI restriction site"

( i x ) FEATURE:
        ( A ) NAME/KEY: -
        ( B ) LOCATION: 1..42
        ( D ) OTHER INFORMATION: /label=oligonucleotide
            / note= "synthetic primer used to create
            recognition sites"

( x i ) SEQUENCE DESCRIPTION: SEQ ID NO: 4:

GCTTATATCG ATGGTACCTG CAGTCACCCA GAAACGCTGG TG                               42

( 2 ) INFORMATION FOR SEQ ID NO: 5:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 7..12
        ( D ) OTHER INFORMATION: /function="HindIII restriction
            site"

( i x ) FEATURE:
        ( A ) NAME/KEY: -
        ( B ) LOCATION: 1..32
        ( D ) OTHER INFORMATION: /label=oligonucleotide
            / note= "synthetic primer used to create
            recognition sites"

( x i ) SEQUENCE DESCRIPTION: SEQ ID NO: 5:

GCAACCAAGC TTGAGTAAAC TTGGTCTGAC AG                                          32

( 2 ) INFORMATION FOR SEQ ID NO: 6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
  ( A ) NAME/KEY: misc_feature
  ( B ) LOCATION: 7..12
  ( D ) OTHER INFORMATION: /function="PstI restriction site"

( i x ) FEATURE:
  ( A ) NAME/KEY: -
  ( B ) LOCATION: 1..30
  ( D ) OTHER INFORMATION: /label=oligonucleotide
        / note= "synthetic primer used to create
        recognition sites"

( x i ) SEQUENCE DESCRIPTION: SEQ ID NO: 6:

GCTTATCTGC AGCTCACCCA GAAACGCTGG    30

( 2 ) INFORMATION FOR SEQ ID NO: 7:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 4..9
    ( D ) OTHER INFORMATION: /function="HindIII restriction
          site"

( i x ) FEATURE:
    ( A ) NAME/KEY: -
    ( B ) LOCATION: 1..29
    ( D ) OTHER INFORMATION: /label=oligonucleotide
          / note= "synthetic 3'primer used to create
          recognition sites"

( x i ) SEQUENCE DESCRIPTION: SEQ ID NO: 7:

GCGAAGCTTC TAGTTGCAGT AGTTCTCCA    29

( 2 ) INFORMATION FOR SEQ ID NO: 8:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 5..10
    ( D ) OTHER INFORMATION: /function="KpnI restriction site"

( i x ) FEATURE:
    ( A ) NAME/KEY: -
    ( B ) LOCATION: 1..30
    ( D ) OTHER INFORMATION: /label=oligonucleotide
          / note= "synthetic 5'primer used to create
          recognition sites"

( x i ) SEQUENCE DESCRIPTION: SEQ ID NO: 8:

GGCCGGTACC TTTGTGAACC AACACCTGTG    30

( 2 ) INFORMATION FOR SEQ ID NO: 9:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 4..9
    ( D ) OTHER INFORMATION: /function="KpnI restriction site"

( i x ) FEATURE:
    ( A ) NAME/KEY: -
    ( B ) LOCATION: 1..35
    ( D ) OTHER INFORMATION: /label=oligonucleotide
        / note= "synthetic 5'primer used to create
        recognition sites"

( x i ) SEQUENCE DESCRIPTION: SEQ ID NO: 9:

GCCGGTACCA AGAGATTTGT GAACCAACAC CTGTG      35

( 2 ) INFORMATION FOR SEQ ID NO: 10:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: -
        ( B ) LOCATION: 1..22
        ( D ) OTHER INFORMATION: /label=oligonucleotide
            / note= "synthetic primer for confirmation of
            insulin nucleotide sequence"

( x i ) SEQUENCE DESCRIPTION: SEQ ID NO: 10:

ACGTATCTAC CAACGATTTG AC      22

( 2 ) INFORMATION FOR SEQ ID NO: 11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: -
        ( B ) LOCATION: 1..18
        ( D ) OTHER INFORMATION: /label=oligonucleotide
            / note= "synthetic primer for confirmation of
            insulin nucleotide sequence"

( x i ) SEQUENCE DESCRIPTION: SEQ ID NO: 11:

TTCTGCAGCC GCTACCTC      18

( 2 ) INFORMATION FOR SEQ ID NO: 12:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 5..10
        ( D ) OTHER INFORMATION: /function="HindIII restriction
            site"

( i x ) FEATURE:
  ( A ) NAME/KEY: -
  ( B ) LOCATION: 1..31
  ( D ) OTHER INFORMATION: /label=oligonucleotide
    / note= "synthetic 3'primer for BDNF synthesis"

( x i ) SEQUENCE DESCRIPTION: SEQ ID NO: 12:

CTCCAAGCTT ACTATCTTCC CCTTTTAATG G      31

( 2 ) INFORMATION FOR SEQ ID NO: 13:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: misc_feature
  ( B ) LOCATION: 5..10
  ( D ) OTHER INFORMATION: /function="KpnI restriction site"

( i x ) FEATURE:
  ( A ) NAME/KEY: -
  ( B ) LOCATION: 1..27
  ( D ) OTHER INFORMATION: /label=oligonucleotide
    / note= "synthetic 5'primer for proBDNF synthesis"

( x i ) SEQUENCE DESCRIPTION: SEQ ID NO: 13:

ACATGGTACC ATGAAGGCTG CGCCCAT      27

( 2 ) INFORMATION FOR SEQ ID NO: 14:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: misc_feature
  ( B ) LOCATION: 5..10
  ( D ) OTHER INFORMATION: /function="KpnI restriction site"

( i x ) FEATURE:
  ( A ) NAME/KEY: -
  ( B ) LOCATION: 1..27
  ( D ) OTHER INFORMATION: /label=oligonucleotide
    / note= "synthetic 5'primer for mature BDNF
    synthesis"

( x i ) SEQUENCE DESCRIPTION: SEQ ID NO: 14:

ACATGGTACC AGGGTTCGGC GCCACTC      27

( 2 ) INFORMATION FOR SEQ ID NO: 15:

( i ) SEQUENCE CHARACTERISTICS:
  ( A ) LENGTH: 29 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: misc_feature
  ( B ) LOCATION: 5..10
  ( D ) OTHER INFORMATION: /function="KpnI restriction site"

( i x ) FEATURE:

-continued ( A ) NAME/KEY: -
                    ( B ) LOCATION: 1..29
                    ( D ) OTHER INFORMATION: /label=oligonucleotide
                            / note= "synthetic 5'primer for proNT-3 synthesis"

( x i ) SEQUENCE DESCRIPTION: SEQ ID NO: 15:

ACATGGTACC AACAACATGG ATCAAAGGA                                                29

( 2 ) INFORMATION FOR SEQ ID NO: 16:

( i ) SEQUENCE CHARACTERISTICS:
                    ( A ) LENGTH: 29 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i x ) FEATURE:
                    ( A ) NAME/KEY: misc_feature
                    ( B ) LOCATION: 5..10
                    ( D ) OTHER INFORMATION: /function="HindIII restriction
                            site"

( i x ) FEATURE:
                    ( A ) NAME/KEY: -
                    ( B ) LOCATION: 1..29
                    ( D ) OTHER INFORMATION: /label=oligonucleotide
                            / note= "synthetic 3'primer for proNT-3 synthesis"

( x i ) SEQUENCE DESCRIPTION: SEQ ID NO: 16:

ACATAAGCTT GCCAATTCAT GTTCTTCCG                                                29

( 2 ) INFORMATION FOR SEQ ID NO: 17:

( i ) SEQUENCE CHARACTERISTICS:
                    ( A ) LENGTH: 29 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i x ) FEATURE:
                    ( A ) NAME/KEY: misc_feature
                    ( B ) LOCATION: 5..10
                    ( D ) OTHER INFORMATION: /function="KpnI restriction site"

( i x ) FEATURE:
                    ( A ) NAME/KEY: -
                    ( B ) LOCATION: 1..29
                    ( D ) OTHER INFORMATION: /label=oligonucleotide
                            / note= "synthetic 3'primer for mature NT-3
                            synthesis"

( x i ) SEQUENCE DESCRIPTION: SEQ ID NO: 17:

ACATGGTACC CGGAGGAAAC GCTATGCAG                                                29

( 2 ) INFORMATION FOR SEQ ID NO: 18:

( i ) SEQUENCE CHARACTERISTICS:
                    ( A ) LENGTH: 18 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i x ) FEATURE:
                    ( A ) NAME/KEY: -
                    ( B ) LOCATION: 1..18
                    ( D ) OTHER INFORMATION: /label=oligonucleotide
                            / note= "synthetic 3'primer for mutation of HSP150
                            gene"

( x i ) SEQUENCE DESCRIPTION: SEQ ID NO: 18:

GACGTAGCCA CATGCAGC                                                                                    18

( 2 ) INFORMATION FOR SEQ ID NO: 19:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 6..11
        ( D ) OTHER INFORMATION: /function="XhoI restriction site"

( i x ) FEATURE:
        ( A ) NAME/KEY: misc_feature
        ( B ) LOCATION: 25..30
        ( D ) OTHER INFORMATION: /function="SpeI restriction site"

( i x ) FEATURE:
        ( A ) NAME/KEY: -
        ( B ) LOCATION: 1..45
        ( D ) OTHER INFORMATION: /label=oligonucleotide
        / note= "synthetic mutagenic 5'primer for mutation
        of HSP150 gene"

( x i ) SEQUENCE DESCRIPTION: SEQ ID NO: 19:

GAATCCTCGA GATATAAAAG GAACACTAGT TGTCTAACGA CAATC                                                      45

( 2 ) INFORMATION FOR SEQ ID NO: 20:

( i ) SEQUENCE CHARACTERISTICS:
        ( A ) LENGTH: 35 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "DNA (synthetic)"

( i i i ) HYPOTHETICAL: NO ( i v ) ANTI-SENSE: NO ( i x ) FEATURE:
        ( A ) NAME/KEY: misc_feature
        ( B ) LOCATION: 1..35
        ( D ) OTHER INFORMATION: /label="XhoI-SalI fragment, see Fig.
        35B"

( i x ) FEATURE:
        ( A ) NAME/KEY: modified_base
        ( B ) LOCATION: 22
        ( D ) OTHER INFORMATION: /function="T to A to make SpeI
        restriction site"

( i x ) FEATURE:
        ( A ) NAME/KEY: modified_base
        ( B ) LOCATION: 24
        ( D ) OTHER INFORMATION: /function="A to T to make SpeI
        restriction site"

( i x ) FEATURE:
        ( A ) NAME/KEY: modified_base
        ( B ) LOCATION: 25
        ( D ) OTHER INFORMATION: /function="A to T to make SpeI
        restriction site"

( x i ) SEQUENCE DESCRIPTION: SEQ ID NO: 20:

TCGAGATATA AAAGGAACAC TTGAAGTCTA ACGAC                                                                 35

( 2 ) INFORMATION FOR SEQ ID NO: 21:

( i ) SEQUENCE CHARACTERISTICS:
( A ) LENGTH: 18 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO: 21:

```
Met Gln Tyr Lys Lys Thr Leu Val Ala Ser Ala Leu Ala Ala Thr Thr
 1               5                  10                    15
Leu Ala
```

METHOD FOR PRODUCTION OF PROTEINS IN YEAST

FIELD OF THE INVENTION

The invention comprises a method, by which useful proteins are secreted through the secretory route of yeast while being posttranslationally modified. The production and secretion is achieved by transformation of yeast cells with a recombinant DNA vector containing the isolated or synthesized HSP150 gene, or a fragment or derivative thereof, of *Saccharomyces cerevisiae* or another yeast, joined to a gene encoding a foreign protein. The fusion gene is expressed under the control of the HSP150 control elements or other control elements.

DESCRIPTION OF THE PRIOR ART

The Secretory Route of Yeast

The yeast cells offer an alternative for the prokaryotes for the production of heterologous proteins by recombinant DNA-technology mainly because they can secrete proteins via the secretory pathway to the exterior of the plasma membrane, either to the cell wall or to the growth medium (Terkamp-Olson and Valenzuela, Curt. Opinion Biotechnol. 1:28-35, 1990). The secretory pathway of yeast consists of the endoplasmic reticulum (ER), Golgi apparatus and secretory vesicles, and it operates similarly as the mammalian secretory pathway. A nascent or newly synthesized polypeptide crosses the ER membrane due to its signal sequence, and is translocated to the lumen of the ER. Vesicles bud off from the ER membrane and fuse with the Golgi membrane and thus transport secretory proteins to the Golgi. The Golgi consists of many membrane-bound compartments through which the secretory proteins pass by vesicular traffic. The vesicles which bud off from the last Golgi subcompartment, fuse with the plasma membrane, and thus the soluble contents of the secretory vesicles are delivered to the cell wall, or to the growth medium. The enzymes resident in the compartments of the secretory route modify secretory proteins with glycans, proteolytic cleavages, disulfide bonds, fatty acylation, oligomerization etc. (Schekman, Annu Rev. Cell Biol. 1:115-143, 1985). These modifications occur similarly, though not identically, in yeast and mammalian cells. For instance, the glycans are different in these two organisms (Ballou, The Molecular Biology of the Yeast Saccharomyces, Strathern, Jones and Broach (eds.) Cold Spring Harbor Laboratory, Cold Spring Harbor, pp. 335-360, 1992). The modifications yield a protein molecule whose conformation is correct or more correct than that of a protein produced in prokaryotic cells (Curtis et al., PNAS 88:5809-5813, 1991). Many of the desired heterologous proteins are secretory proteins. Mammalian proteins expressed in yeast are expected to be modified and folded authentically, and to be secreted to the growth medium. Secretion is desired, since purification of the product from the medium is far more easy than from cell lysates.

The Secretory Proteins of the Yeast *S. cerevisiae*

Diffusion Across the Cell Wall

The number of known proteins which are secreted from *S. cerevisiae* to the cell wall or growth medium is only about 15. Most of them remain intercalated within the cell wall (de Nobel and Barnett, Yeast 7:313-132, 1991). α-Factor (Julius et al., Cell 36:309-318, 1984), Barl protease° (MacKay et al., PNAS 85:55-59, 188), killer toxin and exo-β-1-3-glucanase (Klebl and Tanner, J. Bacteriol. 171:6259-6264, 1989) cross the cell wall and diffuse to the growth medium. The small size of α-factor and killer toxin may explain their facile diffusion across the cell wall, whereas the rules by which other proteins are or are not retained within the cell wall are not known.

Glycosylation

Almost all known secretory proteins of *S cerevisiae* are N-glycosylated during secretion. N-glycan may consist of as many as 200 mannose residues. Yeast-specific N-glycosylation may alter the biological activity of a mannnalian protein, and since N-glycans are immunogenic, proteins which carry them cannot be used as therapeutic agents (Kukuruzinska et al., Annu Rev. Biochem. 56:914-944, 1987).

Regulation

Most of the proteins secreted to the exterior of the plasma membrane of *S. cerevisiae* are not expressed constitutively, but regulated by nutritional conditions the mating type. For instance invertase is expressed only when the glucose concentration of the medium is low. α-Factor is synthesized only in Mate cells and the Barl protease in Mata cells.

Secretion of Glycoproteins in Sec Mutants

The sec mutants of *S. cerevisiae* are temperature-sensitive strains where proteins are secreted normally at 25° C. At the restrictive temperature (37° C.), secretory proteins are synthesized normally, but their intracellular transport is arrested, according to the sec mutation, in different compartments of the secretory route: in the cytoplasm, ER, in vesicles operating between the ER and the Golgi, in different subcompartments of the Golgi, or in secretory vesicles (Schekman, Annu. Rev. Cell Biol. 1:115-143, 1985). All tested secretory proteins have been reported to be arrested intracellularly at 37° C. The following proteins stop in the Golgi complex in the original sec7 mutant: Invertase (Novick et al., Cell 21:205-215, 1980), killer toxin (Bussey et al., Mol. Cell. Biol. 3:133362-1370, 1983), glycoproteins of the cell wall (Novick and Schekman, J. Cell Biol. 96:541-547, 1983), mannans of the cell wall (Sanz et al., Biochim. Biophys. Acta 924:193-203, 1987), α-factor (Julius et al., Cell 36:309-318, 1984), a-agglutinin (Watzele et al., EMBO J. 7:1483-1488, 1988), acid phosphatase (Novick et al., Cell 21:205-215, 1980), α-galactosidase (Tschopp et al., J. Bacteriol. 160:966-970, 1984), CPY of the vacuole (Stevens et al., Cell 30:439-448, 1982) and sulphate permease (Novick et al., Cell 21:205-215, 1980).

Use of Secretory Proteins of *S. cerevisiae* in Secretion of Heterologous Proteins Many foreign proteins have been produced in *S. cerevisiae* intracellularly (Terkamp-Olson and Valenzuela, Biotechnology 1:28-35, 1990). Because the present invention is based on the secretory nature of the product of the HSP150 gene, I will present examples of protein products which have been produced in yeast taking advantage of the secretory route. Secretory heterologous proteins have been produced in yeast in a few cases from authentic structural genes with their own signal sequences, and mostly by using other yeast or mammalian or synthetic signal sequences. Since authentic secretory proteins of mammalian cells often fail to be secreted, sequences of yeast secretory proteins are needed to help the heterologous polypeptide chain to be transported to the exterior of the yeast cell. Other modifications comprise removal of glycosylation sites and removal or addition of proteolytic cleavage sites. The promoters used are often strong constitutive or inducible yeast promoters.

Many heterologous proteins are not secreted by their own signal sequences (Cabezon et al., PNAS 81:6594-6590, 1984; Etcheverry et al., Biotechnology 4:726-730, 1986). The choice of the most efficient signal sequence for each secretory heterologous protein is empiric. An authentic signal sequence has been used e.g. in the production of human lysozyme (Yoshimura et al., BBRC145:712–718, 1987; Jigami et al., Gene 43:273–279, 1986), for *Aspergillus niger* gluco-oxidase (Frederick et al., J. Biol. Chem. 265:3793–3802, 1990), and for human α-amylase and serum albumin (Sato et al., Gene 83:355–356, 1989; Sleep et al., Biotechnology 8:42–46, 1990). Human lysozyme has been expressed also with a synthetic signal sequence (Yamamoto et al., BBRC 149:431–436, 1989). The signal secquence of *S. cerevisiae* invertase has been used in production of pro-urokinase. The production level was as high as 15 mg/l, and two thirds of the product were secreted to the growth medium (Melnick et al., J. Biol. Chem. 265:801–807, 1990). Interleukine-1β was secreted from *S. cerevisiae* with the *Candida albicans* glucoamylase signal sequence (Livi et al., J. Biol. Chem. 266:15348–15355, 1991), and with the signal sequence of killer toxin of *Kluyveromyces lactis* (Baldari et al., EMBO J. 6:229–234, 1987).

The system mostly used system for the secretion of heterologous proteins in *S. cerevisiae* is pre-pro-α-factor, which consists of an amino-terminal signal sequence (pre) followed by the pro-portion, which together consist of 89 amino acids. The pro-portion has 3 N-glycans and its six C-terminal amino acids are Lys-Arg-Glu-Ala-Glu-Ala$_{89}$ (spacer). The spacer is followed by four repeats of a 13 amino acid β-factor portion which are separated from each other by similar spacers as above. The kex2 protease which is located in the Golgi cleaves the polypeptide chain at the C-terminal side of each pair of basic amino acids. The dipeptidylaminopeptidase (STE13 gene product) removes the Glu-Ala pairs and liberates the mature α-factor molecules from the carrier. In the production system, the heterologous protein is fused by recombinant DNA technology in frame to the pre-pro-portion of α-factor, which leads the fusion protein to the secretory pathway and takes it to the Golgi. The kex2 protease liberates the heterologous protein from the pro-portion, and the Glu-Ala residues are removed with varying efficiency. The α-factor pre-pro-carrier has been used to secrete from *S. cerevisiae* human epidermal growth fact o r (hEGF), β-endorfin, interferons, granulocyte/ macrophage colony stimulating factor (GM/CSF), serum albumin and nerve growth factor (hNGF) (Brake et al., PNAS 81:4642–4646, 1984; Bitter et al., PNAS 81:5330, 1984; Singh et al., Nucl Acid. Res. 12:8927, 1984; Cantrell et al., PNAS 82:6250–6254, 1985; Sleep et al., Biotechnology 8:42–46, 1990; Sakai et al., Biotechnology 9: 1382–1385, 1991).

Alternatively, a heterologous protein can be detached from a carrier sequence after secretion with proteolytic enzymes, or chemically (Moks et al., Biotechnology 5:379–382, 1987), provided that the junction between the carrier and the product contains the required amino acids.

The industrial production of human insulin is a successful application of the α-factor system in *S. cerevisiae*. The gene encoding human insulin has been joined in frame to the nucleotide sequence encoding the pre-pro-portion of α-factor, either preserving or removing the codons for the glutamate and alanine residues downstream of the kex2 site (Thim et al., PNAS 83:6766–6770, 1986). The insulin molecule itself consists of the parts B-Arg-Arg-C-Lys-Arg-A. The oligopeptides B, C and A are thus separated by the recognition sites Arg-Arg and Lys-Arg of the kex2 protease. Indeed, the kex2-protease detaches the B, C and A parts from each other when the fusion protein reaches the late Golgi. The cleavage may occur inefficiently if the expression level of the fusion protein is high (Thim et al., 1986), and does not occur at all if the Glu-Ala sequences are missing (Zsebo et al., J. Biol. Chem. 261:5858, 1986). In the α-factor system the essential part for efficient secretion is the pro-portion, since the signal sequence can be exchanged to another (Sleep et al., Biotechnology 8:42–46, 1990; Clements et al., Gene 106:267–272, 1991). The fusion gene can be expressed either under the control of the α-factor promoter, or under another promoter.

The Bar1 protease is translocated to the secretory route by its signal sequence and is secreted across the cell wall to the growth medium, like α-factor. It is N-glycosylated and does not appear to be processed by the kex2 protease though it has kex2 sites. It has been attempted to be used similarly as α-factor for heterotogous protein secretion from yeast. The gene encoding the foreign protein is joined to the BAR1 gene or a fragment thereof, and the fusion protein is expected to be secreted efficiently to the growth medium (EP-patent application 220 689).

Other Yeasts as Hosts for Heterologous Protein Production

Other yeasts besides *S. cerevisiae* can be used as hosts for protein production provided that transformation methods and expression vectors are available (Buckholz and Gleeson, Biotechnology 9:1067–1072, 1992). *Kluyveromyces lactis* secretes efficiently pro-chymosin to the growth medium, whereas *S. cerevisiae* does not secrete this product (van den Berg et al., Biotechnology 8:135–139, 1990). *Pichia pastoris* secretes lysozyme into the medium (Digan et al., Biotechnology 7:160–164, 1989). The glycosylation apparatus of *P. pastoris* is different from that of *S. cerevisiae*, since it does not hyperglycosylate proteins (Grinna and Tschopp, Yeast, 5: 107–115, 1989). *Schizosaccharomyces pombe* has deviated in evolution very far from *S. cerevisiae* and its cell cycle resembles that of mammalian cells (Forsburg and Nurse, Annu. Rev. Cell Biol. 7:27–256, 1991). The 2μ plasmids of *S. cerevisiae* function in *Torulaspora delbrueckii*, which is traditionally used in baking and secondary fermentation of wines.

DESCRIPTION OF THE INVENTION

The HSP150 Gene and the hsp150 Protein

I have cloned the novel HSP150 gene from the yeast *S. cerevisiae*, which encodes the secretory protein hsp150. The secretion characteristics, glycosylation and the regulation of the protein are different from those of other known secretory proteins of *S. cerevisiae*. The invention comprises the use of the HSP150 gene to produce and secrete other proteins from yeast.

In *S. cerevisiae* about 90% of newly synthesized hsp150 is secreted across the cell wall to the growth medium. Thus, hsp150 is one of the rare yeast proteins known to be secreted to the growth medium. In the several sec mutants, notably sec7, hsp150 is secreted at the restrictive temperature (37° C.), in contrast to other known secretory proteins. Hsp150 is O-glycosylated with di-, tri-, tetra- and pentamannosides. The regulation of the HSP150 gene differs from that of other genes encoding secretory proteins, since heat shock and nitrogen starvation activate its transcription. When cells are shifted from 25° C. to 37° C., the expression of the hsp150 protein is dramatically increased. The hsp150 protein has been described in the doctoral thesis of my student Leena Nevalainen (ISBN 952-90-2953-5, Yliopistopaino, Helsinki 1991).

The HSP150 gene was cloned by screening the cDNA library of *S. cerevisiae* with an oligonucleotide, synthesized according to the amino acid sequence of a peptide cleaved from the hsp150 protein which had been purified from the growth medium of *S. cerevisiae*. The sequence of the positive clones was different from any other known cloned DNA sequence. The deduced amino acid sequence revealed no significant homology with known proteins (FIG. 1). The primary translation product of 413 amino acids consists of an N-terminal amino acid signal sequence, of subunit I of 54 amino acids, and of subunit II of 341 amino acids. Subunit II consists largely of a repetitive region where a 19 amino acid peptide is repeated 11 times (FIG. 2). This region appears not to adopt any conformation but occurs as an unstructured random coil.

The primary translation product of HSP150 is translocated through the ER membrane to the lumen. The signal sequence is removed and mannose residues are attached to serine and threonine residues. The protein is transported to the Golgi complex, where the glycans are extended to their final sizes. Hsp150 has no potential N-glycosylation sites, and about 25% of its amino acids are serines and threonines, potential O-glycosylation sites.

Besides the removal of the signal sequence, hsp150 is processed with another proteolytic cleavage. Subunits I and II are detached from each other, apparently in the late Golgi by the kex2 protease. However, they remain noncovalently attached to each other, unlike the cleavage products of α-factor and killer toxin. The dimer is then secreted via secretory vesicles to the exterior of the plasma membrane and diffuses across the cell wall to the growth medium.

The hsp150 protein is secreted at the restrictive temperature in the sec7, sec3, sec10 and sec21 mutants, where other known proteins accumulate in the ER, Golgi or secretory vesicles. Thus, under these conditions oly few other proteins besides hsp150 are secreted.

The regulation of the level of the hsp150 protein occurs at the transcriptional level. Heat shock and nitrogen starvation at the physiological temperature result in activation of transcription. Due to this, HSP150 is a stress gene (Lindquist and Craig, Annu. Rev. Genet. 22:631–677, 1988).

The hsp150 protein appears to be conserved, since antigenic homologs were found in other yeasts like *Kluyveromyces marxianus, Torulaspora delbrueckii* and *Schizosaccharomyces pombe*. An antigenic homolog is a protein that is recognized by anti-hsp150 antiserum. The expression of all studied homologs was increased by heat shock. All homologs of the *S. cerevisiae* HSp150 gene are called here HSP150 genes and all homologs of the *S. cerevisiae* hsp150 proteins are called hsp150 proteins.

The Use of the HSP150 Gene in Secretion of Other Proteins

The invention provides a novel DNA structure which encodes a carrier protein to guide other proteins to the secretory route of yeast to be secreted to the exterior of the cell. In the vectors of this invention, the gene encoding the desired protein is joined in frame to the isolated or synthesized HSP150 gene, or to a fragment or a derivative thereof. The repetitive random coil region of hsp150 may be perticularly advantageous to be joined to other proteins. The desired protein can be produced as a fusion protein, in which case it can be detached from the carrier protein after secretion by proteolytic or chemical cleavage. Alternatively, the protein product can be cleaved from the carrier protein intracellularly by enzymes located in the secretory organelles.

When the recombinant DNA construct encoding the fusion protein is transformed to a sec strain where under restrictive conditions predominantly hsp150 is secreted, the host cells perform the purification of the protein product not only from cellular proteins, but also from many secretory proteins.

The fusion gene is expressed under the control of the upstream and downstream control elements of the HSP150 gene, or of other control elements. A heat shock promoter and a nutrient-responsive promoter of HSP150 can be used to regulate the expression of the fusion gene by temperature or nutrient starvation, respectively.

Because antigenic homologs of *S. cerevisiae* hsp150 are expressed also in other yeasts, the HSP150 homologs of these yeasts can be used to express heterologous proteins in *S. cerevisiae* or other yeasts.

DETAILED DESCRIPTION OF THE USE OF THE HSP150 GENE FOR PROTEIN PRODUCTION

To localize the part of the hsp150 protein which allows a hsp150-fusion protein to be secreted to the growth medium, different fragments of the HSP150 structural gene (FIG. 1) are joined in frame to the gene encoding the desired protein, followed by examination of the expression of the fusion protein. The hsp150 protein can be assumed to consist of at least four domains. These are 1) the signal sequence (amino acids 1–18 of the primary translation product), subunit I (amino acids 19–72), the repetitive random coil region of subunit II (amino acids 73–299) and the C-terminus of subunit II (amino acids 300–413; FIG. 2). Note that in FIGS. 1 and 2 the first amino acid of the primary translation product is amino acid number 1, whereas in SEQ ID No. 1 the first amino acid of the mature protein following the signal sequence is amino acid number 1, and the first amino acid of the primary translation product is number –18.

In the first embodiment of the invention the hsp150-signal sequence is used to translocate the fusion protein to the secretory pathway. In another embodiment, any other functional natural signal sequence, any synthetic signal sequence, or any hybrid signal sequence is used instead of, or in addition to the hsp150-signal sequence. A DNA molecule where e.g. the signal sequence is not authentic, is called a derivative. The function of a nonauthentic signal sequence is tested by comparing the amount of secreted protein product to that remaining intracellular. In a third embodiment the foreign protein is engineered between the signal sequence and the hsp150 sequence.

Because a cut within a protein domain often leads to incorrect folding and consequently to problems in secretion, the fragments of hsp150 to be fused to a heterologous protein should form intact domains. The PstI fusion contains the signal sequence and 45 of the 54 amino acids of hsp150 subunit I (FIG. 3). The KpnI fusion contains the hsp150 signal sequence, subunit I, the repetitive region of subunit II plus the next 22 amino acids. The ClaI fusion contains the whole hsp150 protein except for the 4 C-terminal amino acids. The new vectors contain the gene encoding the desired protein, fused to the 3'-end of the PstI, KpnI or ClaI fragments described above (FIG. 3). The recombinant DNA molecules containing one of the above mentioned fusion genes, under the control of the HSP150 promoter, are transformed into *S. cerevisiae*. The production of the protein product is investigated by measuring its level in the growth medium, cell wall and inside of the cell, by determining biological activity, or by Western blotting or inununoprecipitation experiments, or other methods developed for protein detection.

In another embodinent, any HSP150 sequence, encoding a biologically active or functional fragment or a derivative of the hsp150 protein is fused to the gene encoding the desired protein. In the context of the present invention, the terms "biological activity of a hsp150 protein" and "functionality of a hsp150 protein" refer to the particular secretion characteristics of the hsp150 protein. In a derivative, the HSp150 DNA may have been modified by site directed mutagenesis, or by addition of linkers. Another example of linkers is the addition of proteolytically or chemically clearable sites for the detachment of the protein product from the carrier protein inside or outside of the cell. In the case of the PstI fragment, the heterologous protein will not be cleaved from the hsp150 carrier by intracellular enzymes, due to lack of cleavage sites, and this results in secretion of the fusion protein.

In the case of the KpnI and ClaI fragments, subunit I will probably be cleaved, but the protein product will remain joined to the hsp150 sequence. When a kex2 recognition site, a linker containing a pair of basic amino acids, is added between the hsp150 and the product sequences, the carrier sequence has to guide the fusion protein to the late Golgi, where cleavage takes place. Thereafter the released protein product is secreted by itself. Alternatively, a fusion protein without cleavage sites will be expressed and the product will be released after secretion by enzymes, or chemically, or by cocultivation of a strain secreting the kex2 protease (Brenner and Fuller PNAS 89:922–926, 1992). Different subunits of a heterologous protein may be separated from each other by peptide or polypeptide linkers in the fusion protein.

A protein product here is any heterologous protein, a fragment or a functional derivative thereof, which one wishes to secrete from yeast. The DNA encoding this protein can be modified, for instance by removing sequences coding for the signal sequence or glycosylation sites. Large yeast-specific N-glycans may disturb the biological activity or immunogenicity of the product. In this case the product is expressed from a derivative from which the desired codons have been removed (Travi et al., J. Biol. Chem. 260:4384–4389, 1985). If the product has natural internal kex2 sites, the cleavage of which would destroy it, a derivative is used where those codons have been removed. If the removal of undesired kex2 sites would disturb the biological activity or the secretion of the product, the protein product is expressed in a strain where the KEX2 gene has been disrupted.

Yeast genes expressing their products at high or low level use different codons for many amino acids. Different codons encoding the same amino acid are called synonymous or degenerate codons. Codon usage differs in yeasts, prokaryotes and mammalians (Bennetzen and Hall, J. Biol. Chem. 257:3026–3031, 1982; Guthrie and Abelson, The Molecular Biology of the Yeast Saccharomyces, Strathern, Jones and Broach (eds.), 1982, Cold Spring Harbor N.Y.). The codon usage of HSP150 in S. cerevisiae is that of strongly expressed genes. The level of the hsp150 protein produced and secreted in the sec7 strain in one hour at 37° C. was about 0.5–1 mg/l. When a mammalian gene is expressed in yeast, the poor availability of rarely used codons may decrease the expression level. The whole gene can then be synthesized using different, strongly expressed synonymous codons (Kotula and Curtis, Biotechnology 9: 1386–1389, 1991). A derivative of a DNA fragment can thus be composed of synonymous (degenerate) codons.

The HSP150 recombinant gene is cloned into any vector which replicates autonomously or integrates into the genome of yeast. The copy number of autonomously replicating plasmids, e.g. YEp plasmids may be high, but their mitotic stability may be insufficient (Bitter et al., Meth. Enzymol. 153:516–544, 1987). They contain the 2μ-plasmid sequence responsible for autonomous replication, and an E. coli sequence responsible for replication in E. coli. The vectors contain a genetic marker for selection of yeast transformants, and an antibiotic resistance gene for selection in E. coli. The episomal vectors containing the ARS and CEN sequences occur as a single copy per cell and they are more stable than the YEp vectors. Integrative vectors are used when a DNA fragment is integrated as one or multiple copies into the yeast genome. In this case the recombinant DNA is stable and no selection is needed (Struhl et al., PNAS 76:1035–1039, 1989; Powels et al., Cloning vectors, I-IV, et seq. Elsevier, 1985; Sakai et al., Biotechnology 9:1382–1385, 1991).

Each vector has an origin of replication, which functions in the selected host cell. The vectors have restriction endonuclease sites for insertion of the fusion gene and promoter sequences, and selection markers. The vectors may be modified by removal or addition of restriction sites, or removal of other unwanted nucleotides. The HSP150-gene fusions can be placed under the control of any promoter (Stretler et al., Biotechnology 7:55–60, 1989). One can choose a constitutive or regulated yeast promoter. The strong promoters of e.g. phosphoglycerate kinase (PGK) gene, other genes encoding glycolytic enzymes, and the α-factor gene, are constitutive. When a constitutive promoter is used, the product is synthesized during cell growth. The ADH2 promoter is regulated with ethanol and glucose, the GAL-1-10 and GAL7 promoters with galactose and glucose, the PHO5 promoter with phosphate, and the metallothionine promoter with copper. The heat shock promoters, to which the HSP150 promoter belongs, are regulated by temperature. Hybrid promoters can also be used. A regulated promoter is used when continuous expression of the desired product is harmful for the host cells. Instead of yeast promoters, a strong prokaryotic promoter such as the T7 promoter, can be used, but in this case the yeast strain has to be transformed with a gene encoding the respective polymerase. For transcription termination, the HSP150 terminator, or any other functional terminator is used. Here, promoters and terminators are called control elements.

The present invention is not restricted to any specific vector, promoter, terminator, foreign protein or host cell. Probably the most advantageous hosts are yeasts. In addition to different strains of S. cerevisiae, other yeasts like Kluyveromyces, Torulaspora, Schizosaccharomyces and Pichia can be used. The essential feature of a host, concerning the present application, is a funtional secretory route. Because antigenic homologs of the hsp150 protein were found in many different yeasts besides Saccharomyces, their HSP150 homologs, or allelic derivatives of the HSP150 gene, can be used for production and secretion of useful proteins similarly as described above for the S. cerevisiae HSP150 gene. Any DNA sequences hybridizing to any fragment of the HSP150 DNA sequence can be used to produce a carrier (poly)peptide to secrete a heterologous protein, provided that this particular carrier sequence has the required secretion characteristics.

Because hsp150 is secreted in some of the S. cerevisiae sec mutants under restrictive conditions where many other proteins remain intracellular, the HSP150 fusion gene is transformed into these strains, from which the genomic HSP150 gene has or has not been disrupted. When the transformant has reached a suitable density under permissive conditions, the cells are shifted to nonpermissive temperature. Under nonpermissive conditions, most secretory proteins cease to be secreted, but the fusion protein or the protein product released from the hsp150 carrier continues to be secreted. The advantage gained from secretion is thus manyfold. At the same time the expression of the fusion protein increases due to heat shock, when the fusion gene is under the control of the heat shock promoter. A disadvantage is that the sec mutants do not survive at the restrictive temperature. When cells are shifted back to 25° C., can heat induction be repeated for several cycles.

BRIEF DESCRIPTION OF THE DRAWINGS

FIGS. 1A and 1C. THE NUCLEOTIDE SEQUENCE OF THE HSP150 GENE AND THE AMINO ACID SEQUENCE OF THE hsp150 PROTEIN DEDUCED FROM IT The TATA-element upstream from the HSP150 structural gene is boxed and the HSE-like sequences are underlined with dots. Those nucleotides of the HSE-like elements which conform with the consensus HSE, are marked with stars. Open and closed arrowheads denote the signal sequence and subunit I cleavage sites, respectively. The underlined amino acid sequences 1 and 2 were obtained by direct N-terminal amino acid sequencing of purified hsp150 protein. Amino acid sequences 3–7 were obtained by direct amino acid sequencing of tryptic peptides of hsp150. Downstream from the structural gene, two putative transcription termination signals are doubly underlined. The first amino acid of the primary translation product is designated number 1.

FIG. 2A represents a schematic picture of the hsp150 protein. The N-terminal signal sequence (ss) of 18 amino acids is followed by subunit I of 54 amino acids and subunit II of 341 amino acids. The signal sequence is cleaved between alanines 18 and 19. Subunit I is cleaved off between arginine$_{72}$ and alanine$_{73}$. The shaded boxes represent a peptide which is repeated 11 times in subunit II. FIG. 2B shows the amino acid sequence of the repetitive region, where the homologous peptides are aligned. Two identical peptides presented in bold letters. The amino acid numbering is like in FIGS. 1A–1C. In FIG. 1B, the first peptide, numbered 73–88, corresponds to residues 55 to 70 of SEQ. I.D. NO. 2. As to subsequent peptides, the peptide numbered 96–114 corresponds to residues 78 to 96 of SEQ. I.D. NO. 2. The peptide numbered 115–133 corresponds to residues 97 to 115 of SEQ. I.D. NO. 2. The peptide numbered 139–157 corresponds to residues 121 to 139 of SEQ. I.D. NO. 2. The peptide numbered 163–181 corresponds to residues 145 to 164 of SEQ. I.D. NO. 2. The peptide numbered 187–205 corresponds to residues 169 to 187 of SEQ. I.D. NO. 2. The peptide numbered 206–224 corresponds to residues 188 to 206 of SEQ. I.D. NO. 2. The peptide numbered 225–243 corresponds to residues 207 to 225 of SEQ. I.D. NO. 2. The peptide numbered 244–262 corresponds to residues 226 to 244 of SEQ. I.D. NO. 2. The peptide numbered 263–281 corresponds to residues 245 to 262 of SEQ. I.D. NO. 2. The peptide numbered 282–299 corresponds to residues 263 to of SEQ. I.D. NO. 2.

FIGS. 3A–3D. SCHEMATIC PICTURES OF FUSION GENES CONSISTING OF DIFFERENT FRAGMENTS OF THE HSP150-GENE AND A REPORTER GENE

FIG. 3A represents the structural HSP150 gene, like described in FIG. 2A. A heterologous gene (black line) has been fused downstream from the BamHI-PstI fragment (FIG. 3B), BamHI-KpnI fragment (FIG. 3C) or BamHI-ClaI fragment (FIG. 3B) of HSP150. Stars and dots in the upstream flanking sequence represent HSE-like sequences and the TATA-box, respectively. The letters denote restriction sites for BamHI (B), XhoI (X), PstI (P), KpnI (K) and ClaI (C). The upstream sequences, structural genes and downstream sequences have not been drawn to scale.

The HSP150 cDNA has been ligated to the EcoRI site of the Bluescript vector.

Figure 5:
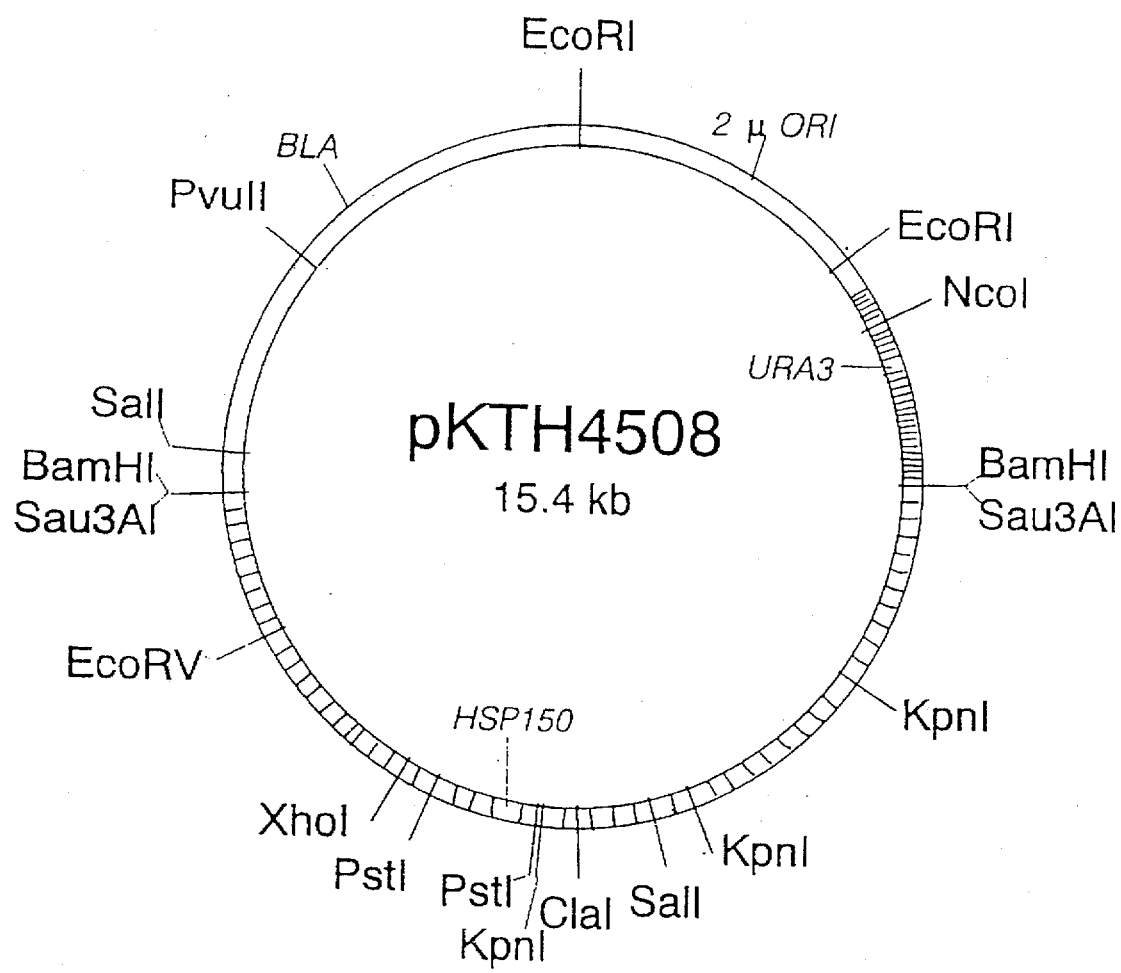

FIG. 5. PLASMID pKTH4508

The genomic clone of HSP150 contains the HSP150 gene in a 7.6 kb Sau3AI fragment ligated to the BamHI site of the YEp24 vector. The restriction pattern of pKTH4509 is identical with that of pKTH4508.

Figure 6:
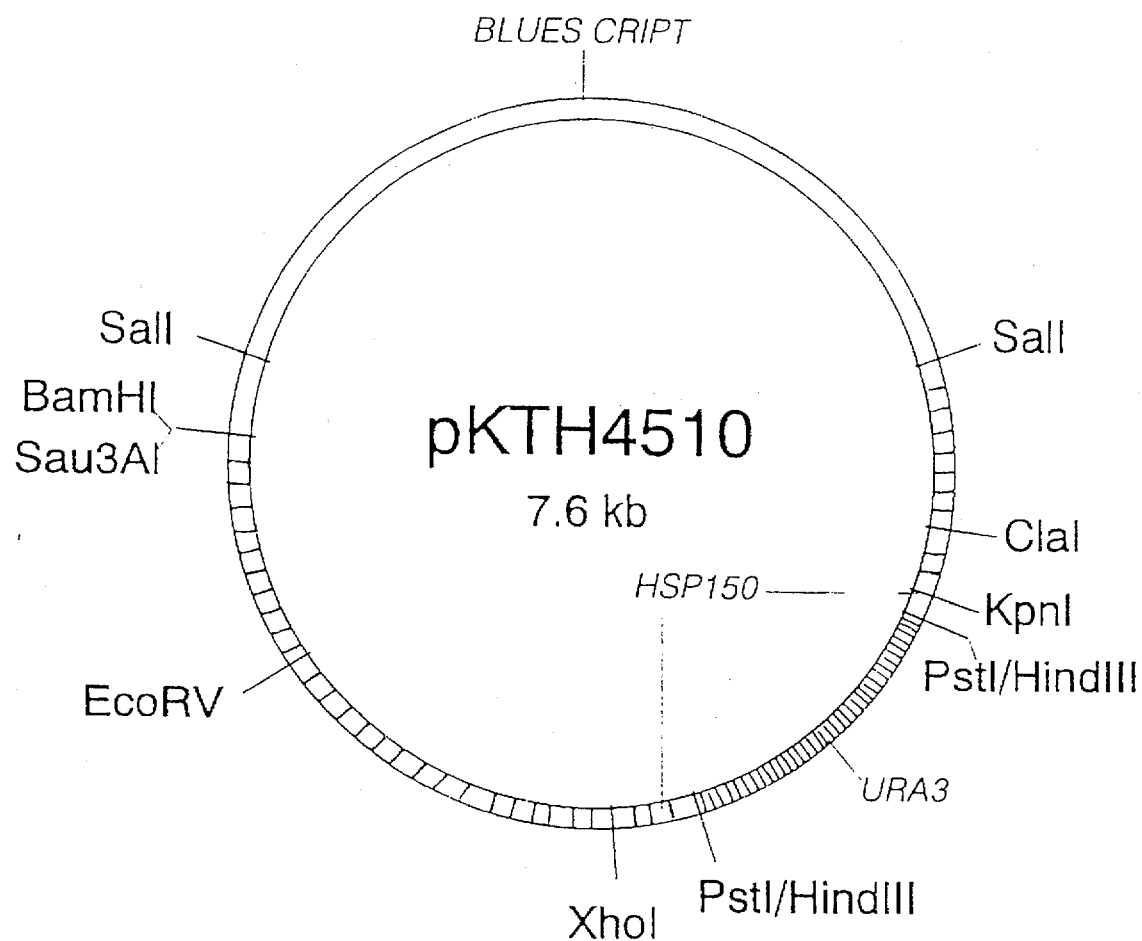

FIG. 6. PLASMID pKTH4510

The HSP150 gene has been disrupted with the URA3 gene.

Figure 7A:
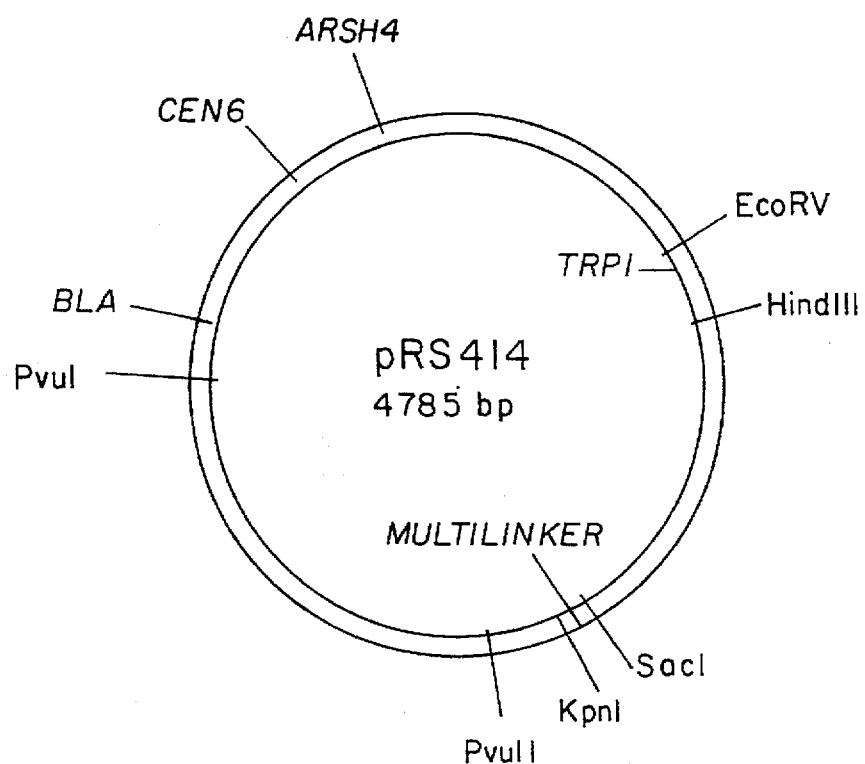
Figure 7B:
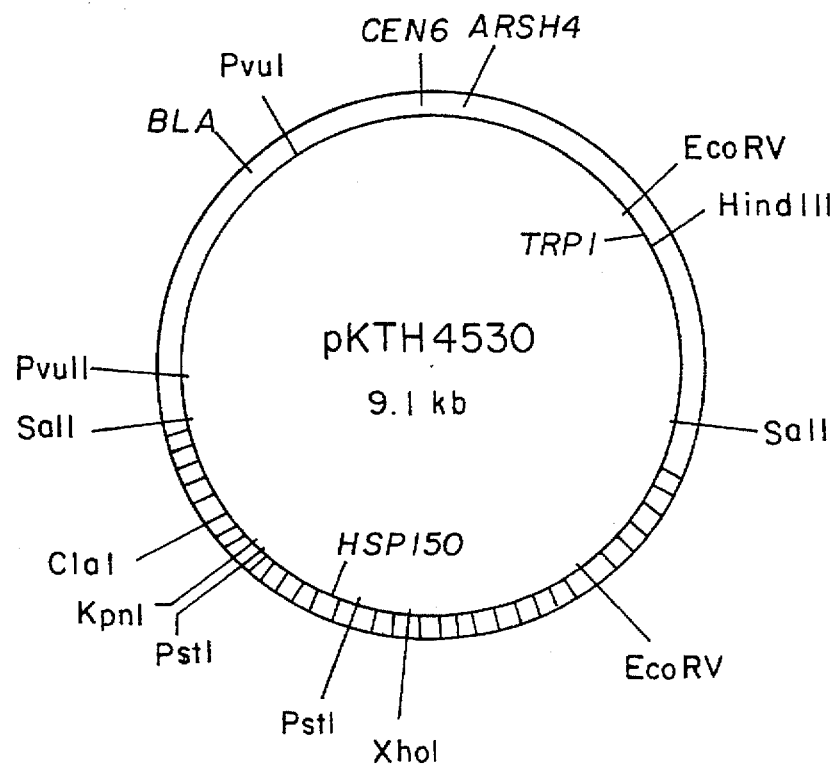

FIGS. 7A and 7B. PLASMIDS pRS414 and pKTH4530

The about 4.3 kb SalI-SalI fragment of HSP150 has been transferred from plasmid pKTH4508 (FIG. 5) to the SalI site of pRS414.

Figure 8:
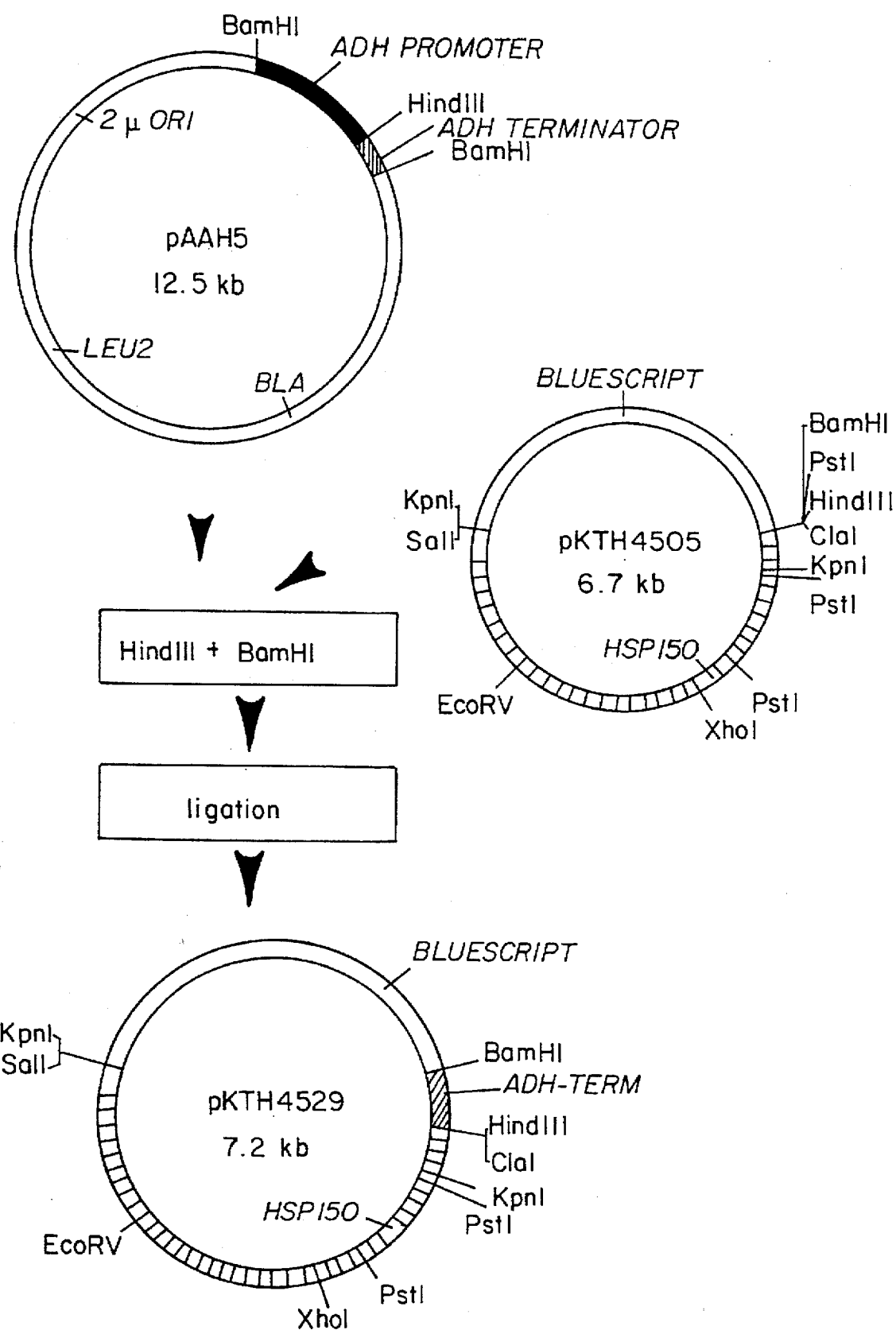

FIG. 8. CONSTRUCTION OF PLASMID pKTH4529

The alcohol dehydrogenase terminator ADH-TERM has been transferred from pAAH5 to pKTH4505.

Figure 9:
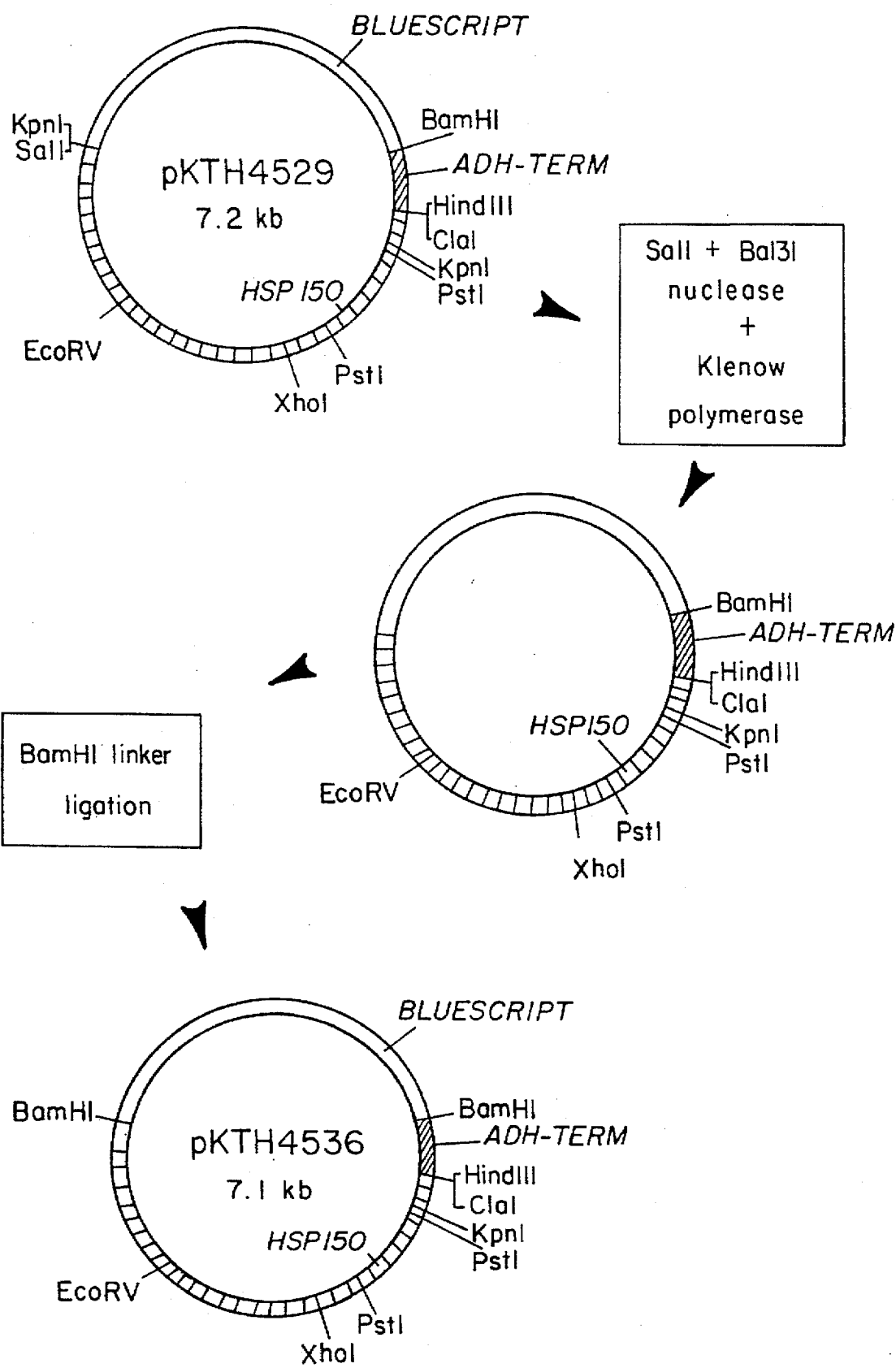

FIG. 9. CONSTRUCTION OF pKTH4536

The KpnI site of pKTH4529 was removed by cutting the plasmid at the SalI site and digesting the DNA with Ba131 nuclease. The ends of the DNA molecule were converted blunt ended with Klenow enzyme and a BamHI linker was ligated to them (Table 1).

Figure 10:
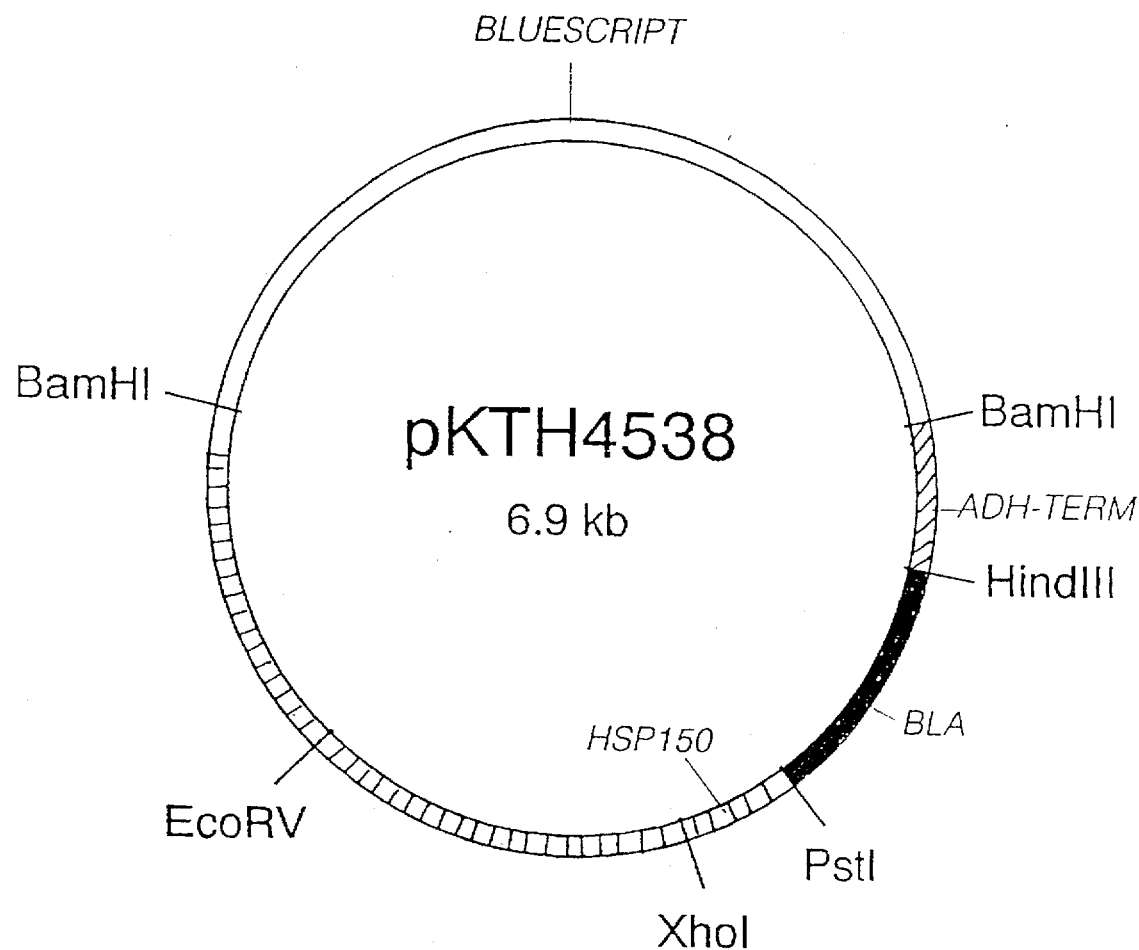

FIG. 10. PLASMID pKTH4538

The PstI-HindIII fragment of about 1000 base pairs of the plasmid pKTH4536 (FIG. 9) has been replaced by the bla gene of 811 base pairs synthesized by PCR.

Figure 11:
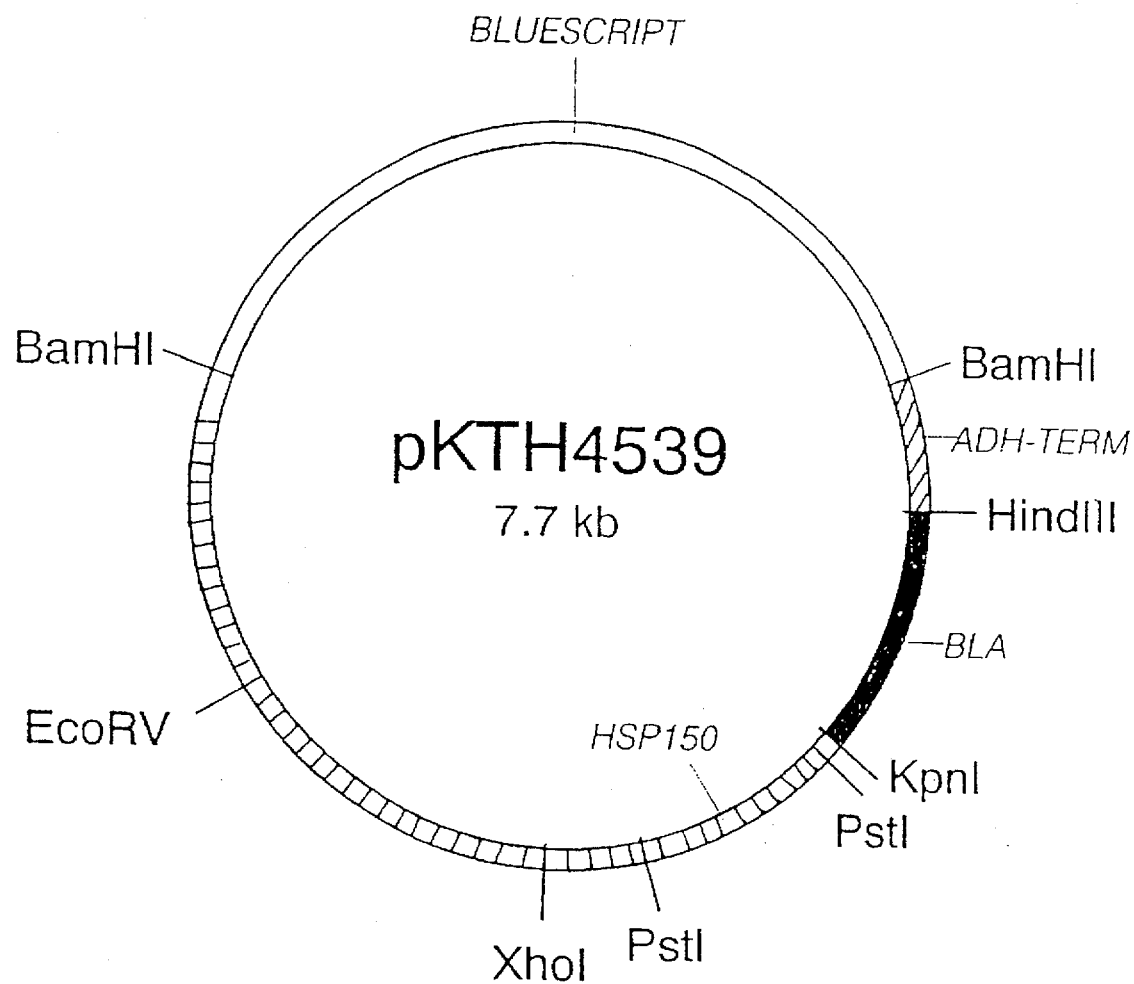

FIG. 11. PLASMID pKTH4539

The KpnI-HindIII fragment of 265 base pairs of plasmid pKTH4536 (FIG. 9) has been replaced by the 816 base pair bla gene synthesized by PCR.

Figure 12:
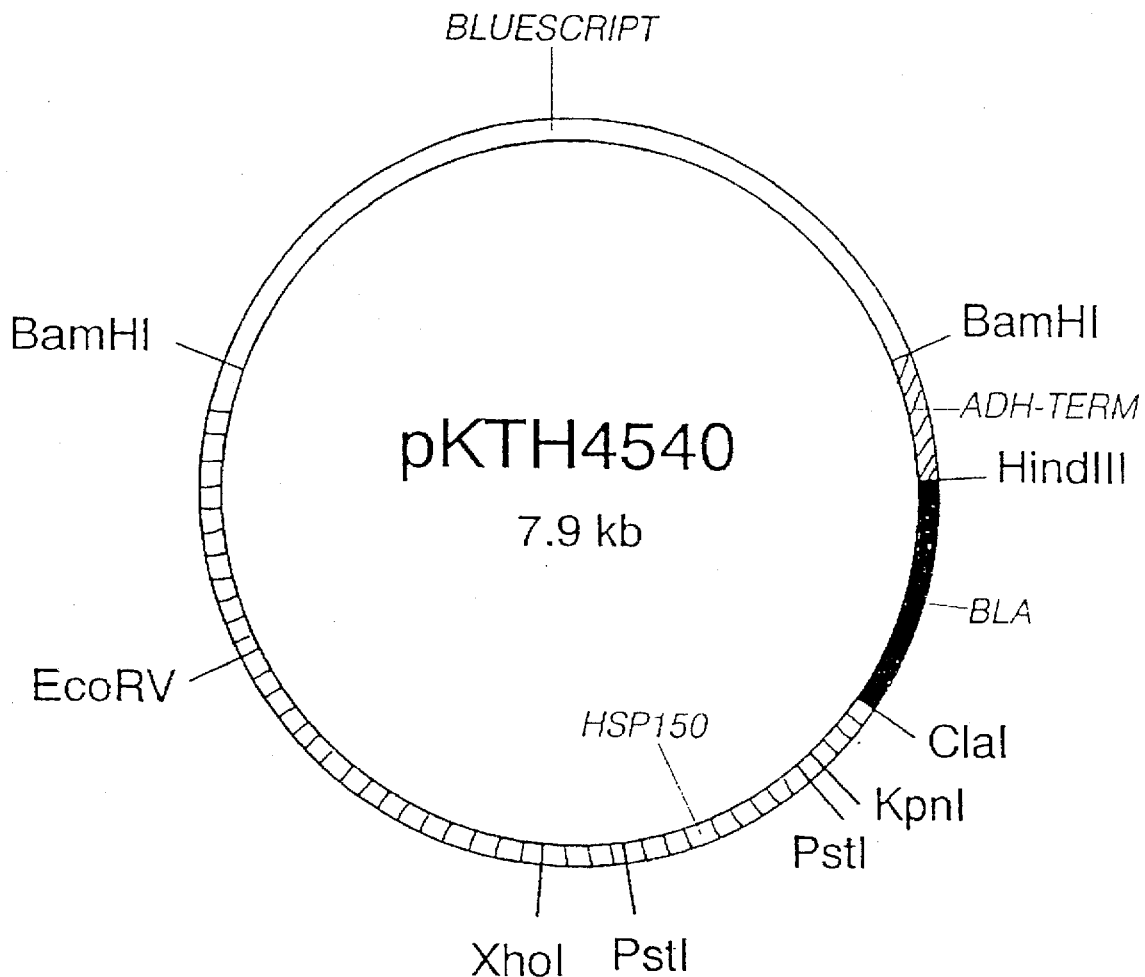

FIG. 12. PLASMID pKTH4540

The 823 base pair bla gene has been ligated between the ClaI and HindIII sites of plasmid pKTH4536 (FIG. 9).

Figure 13:
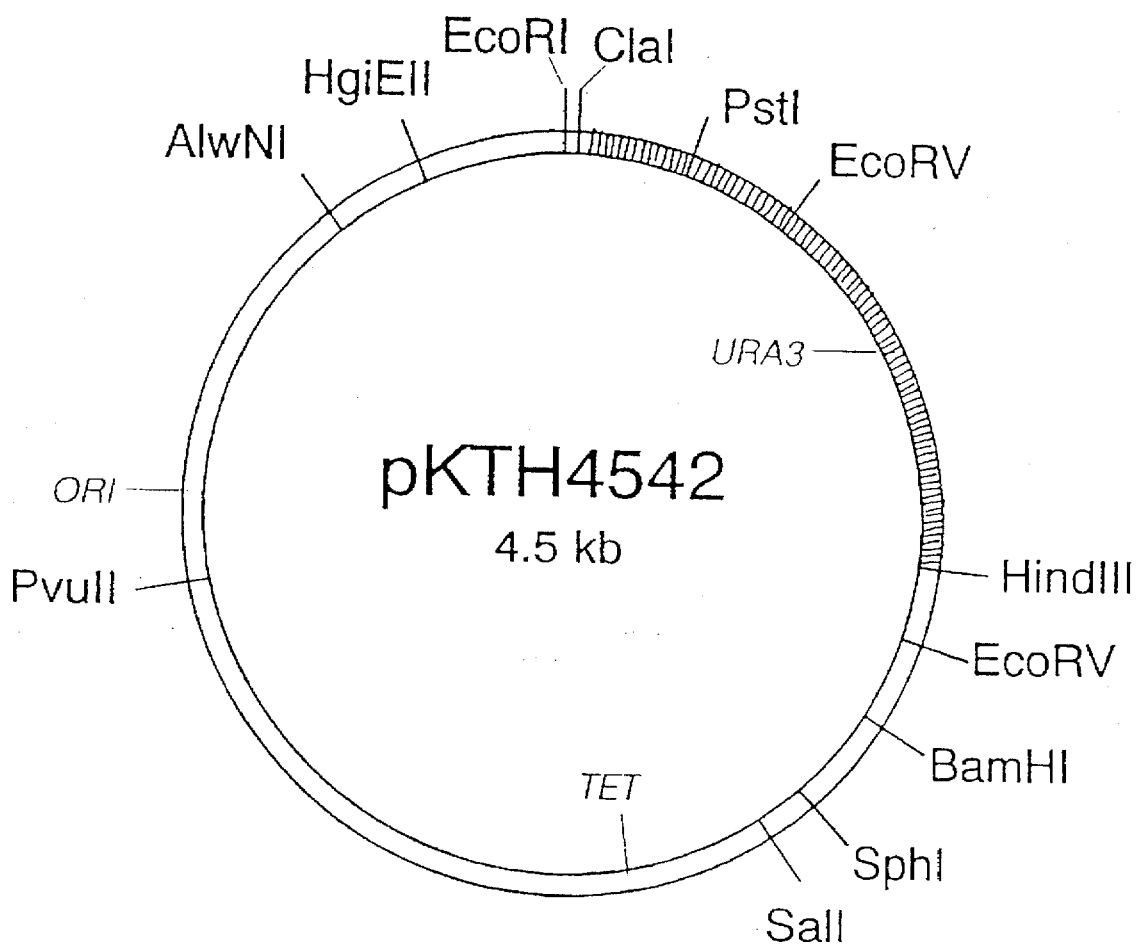

FIG. 13. PLASMID pKTH4542

The integration vector used for the HSP150-bla fusion.

Figure 14:
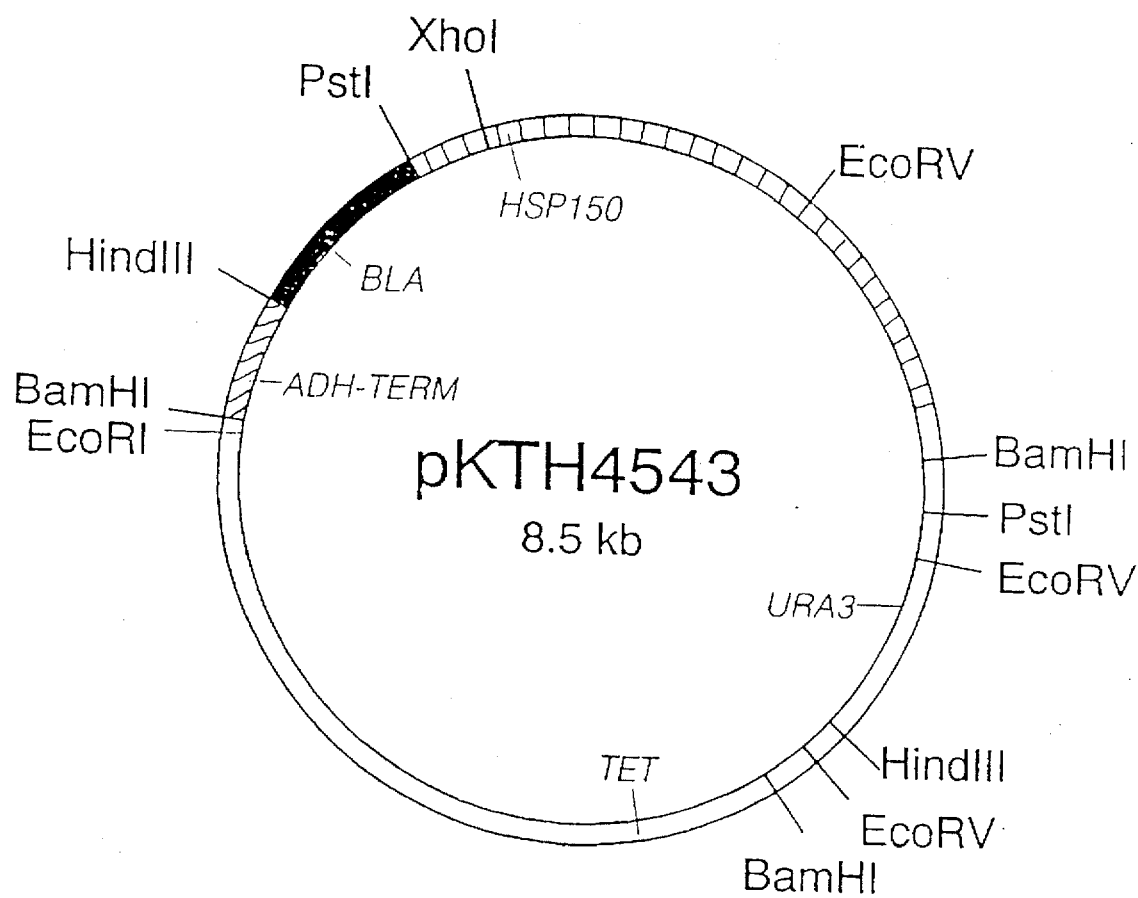

FIG. 14. PLASMID pKTE4543

The HSR150-bla gene fusion of plasmid pKTH4538 (FIG. 10) has been transferred as a BamHI fragment to the ClaI site of pKTH4542.

Figure 15:
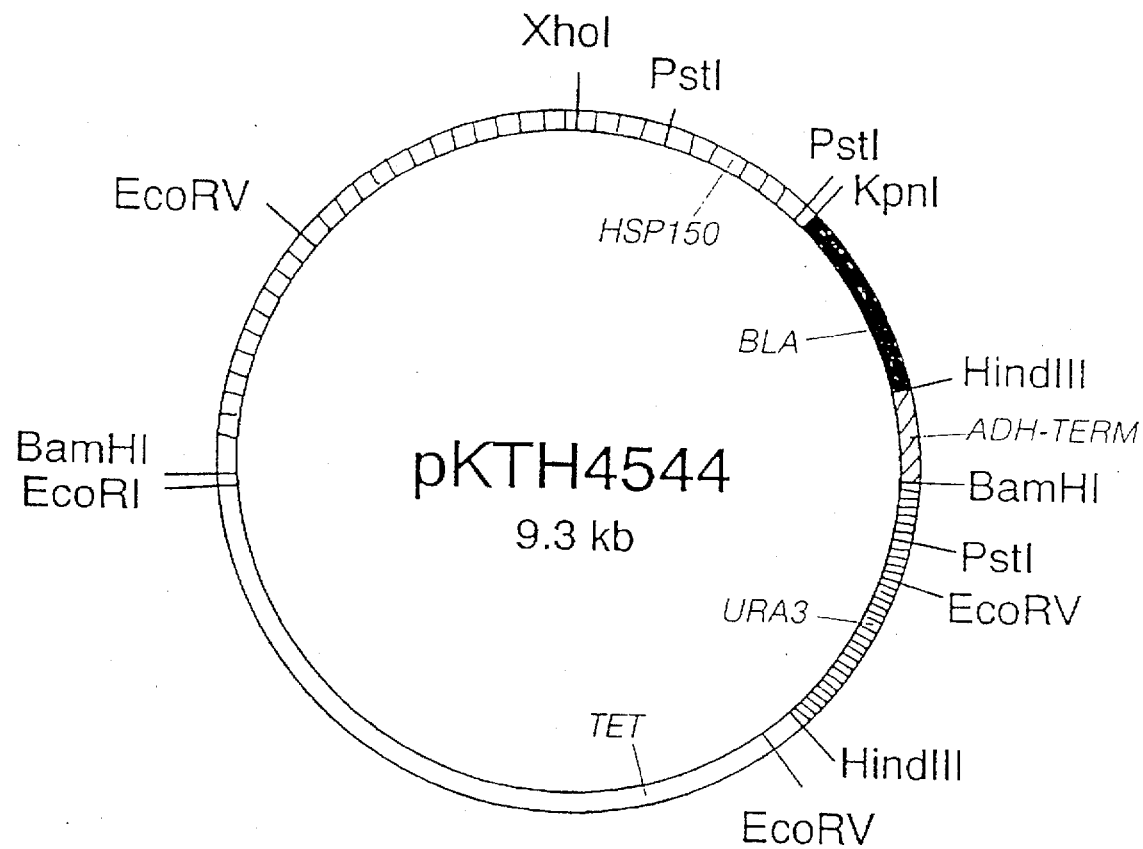

FIG. 15. PLASMID pKTH4544

The HSP150-bla gene fusion of plasmid pKTH4539 (FIG. 11) has been transferred as a BamHI fragment to the ClaI site of pKTH4542.

Figure 16:
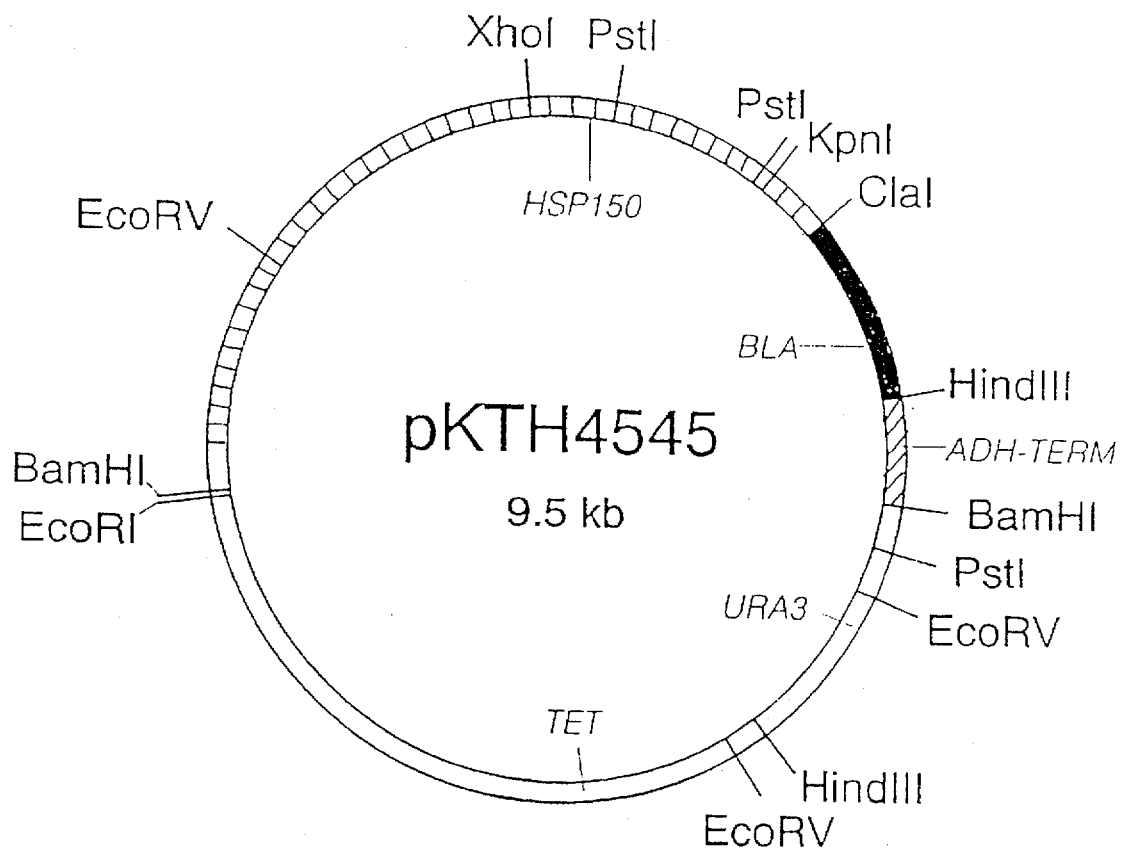

FIG. 16. PLASMID pKTH4545

The HSP150-bla gene fusion of plasmid pKTH4540 (FIG. 12) has been transferred as a BamHI fragment to the ClaI site of pKTH4542.

Figure 17:
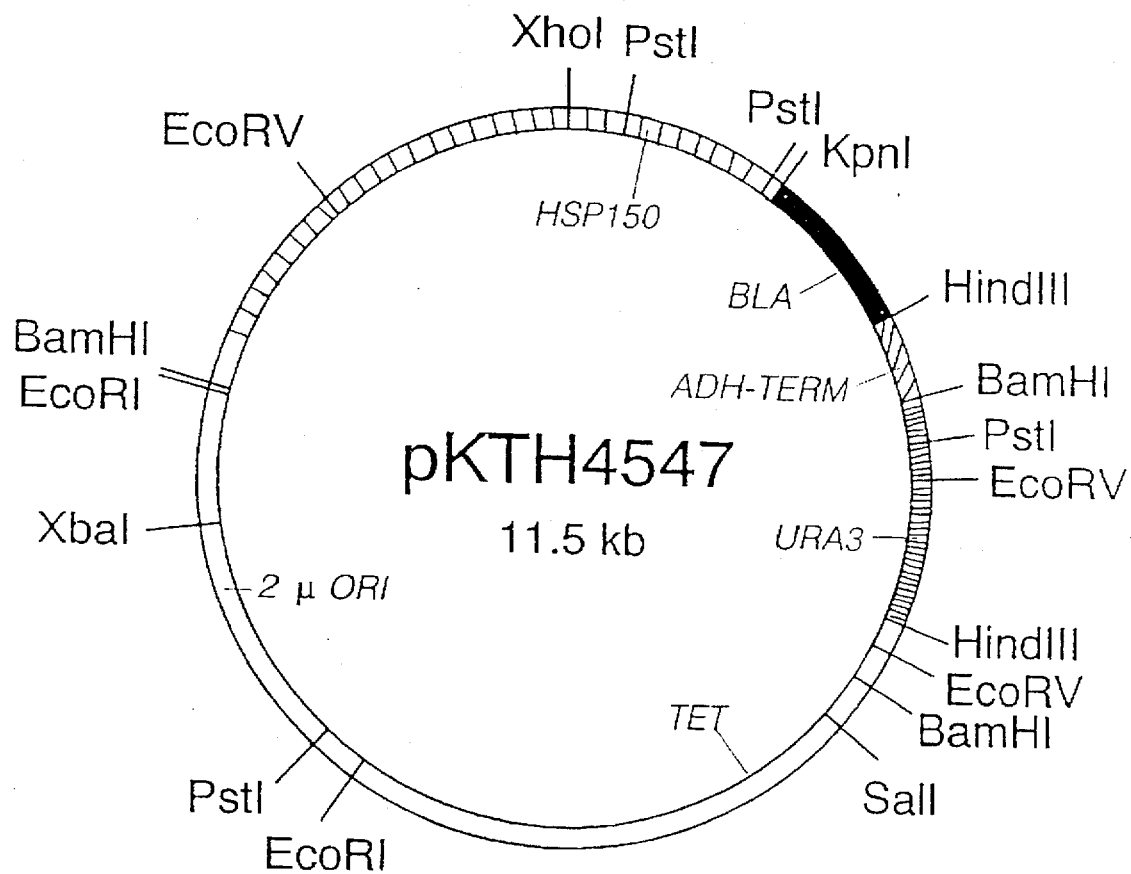

FIG. 17. PLASMID pKTH4547

The sequence responsible for replication (2v) of YEp24 has been transferred as a 2241 base pair EcoRI fragment to the EcoRI site of pKTH4544 (FIG. 15).

Figure 18:
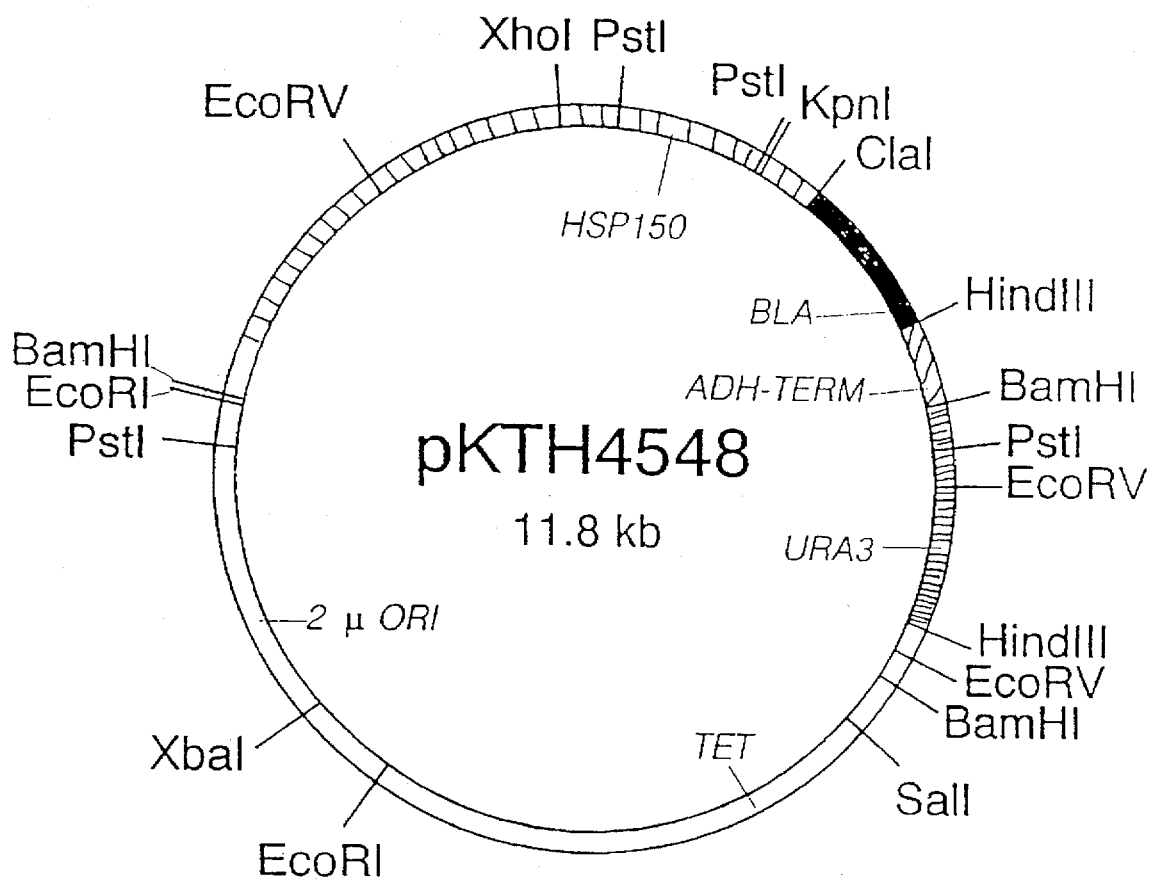

FIG. 18. PLASMID pKTE4548

The 2241 base pair sequence responsible for replication (2μ) of YEp24 has been transferred as an EcoRI fragment to the EcoRI site of plasmid pKTH4545 (FIG. 16).

Figure 19:
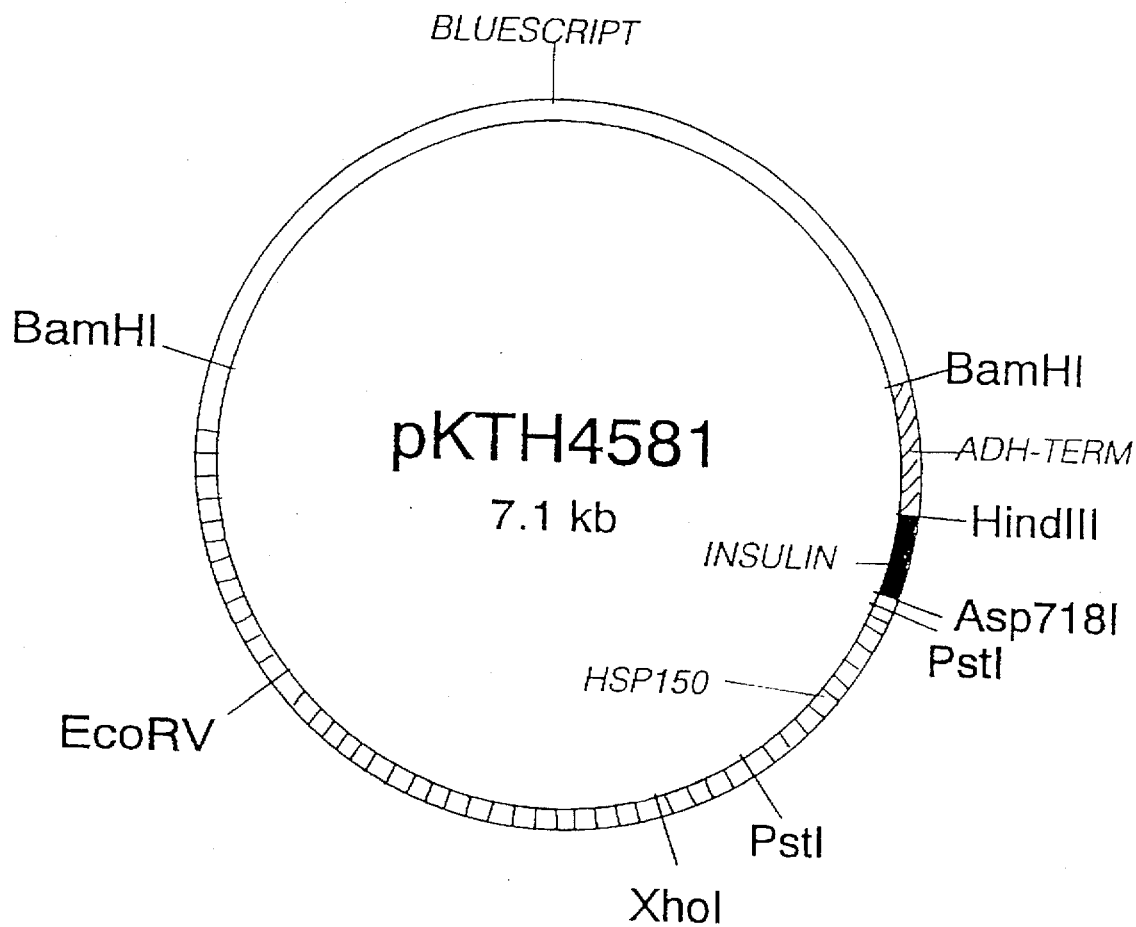

FIG. 19. PLASMID pKTH4581

The Asp718—HindIII PCR-fragment of human insulin cDNA was ligated to the HSP150 gene fragment of plasmid pKTH4539, from which the β-lactamase gene had been removed by Asp718-HindIII digestion, to create plasmid pKTH4581.

Figure 20:
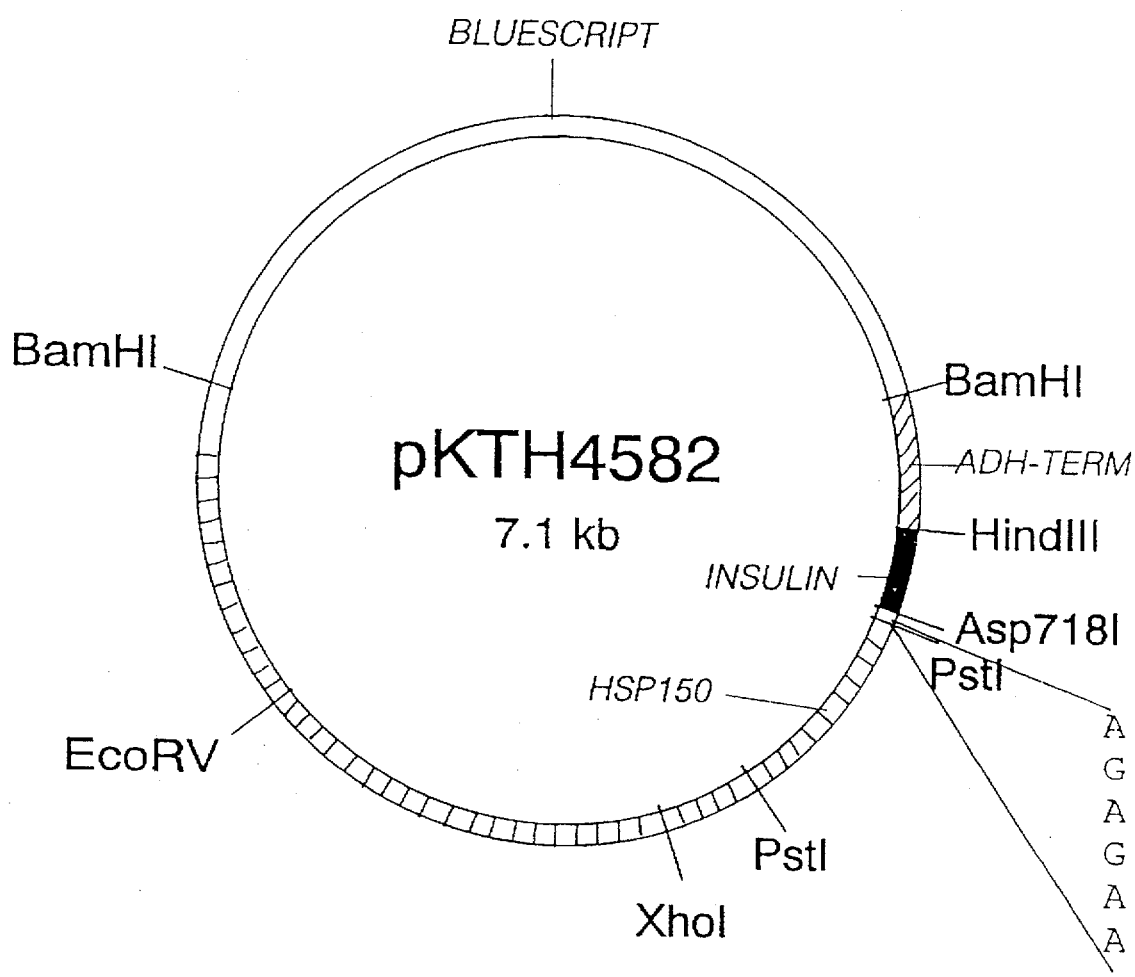

FIG. 20. PLASMID pKTH4582

Plasmid pKTH4582 is identical to pKTH4581 (FIG. 19), except that the sequence AAGAGA was added to the junction of the HSP150 and insulin cDNA fragments.

Figure 21:
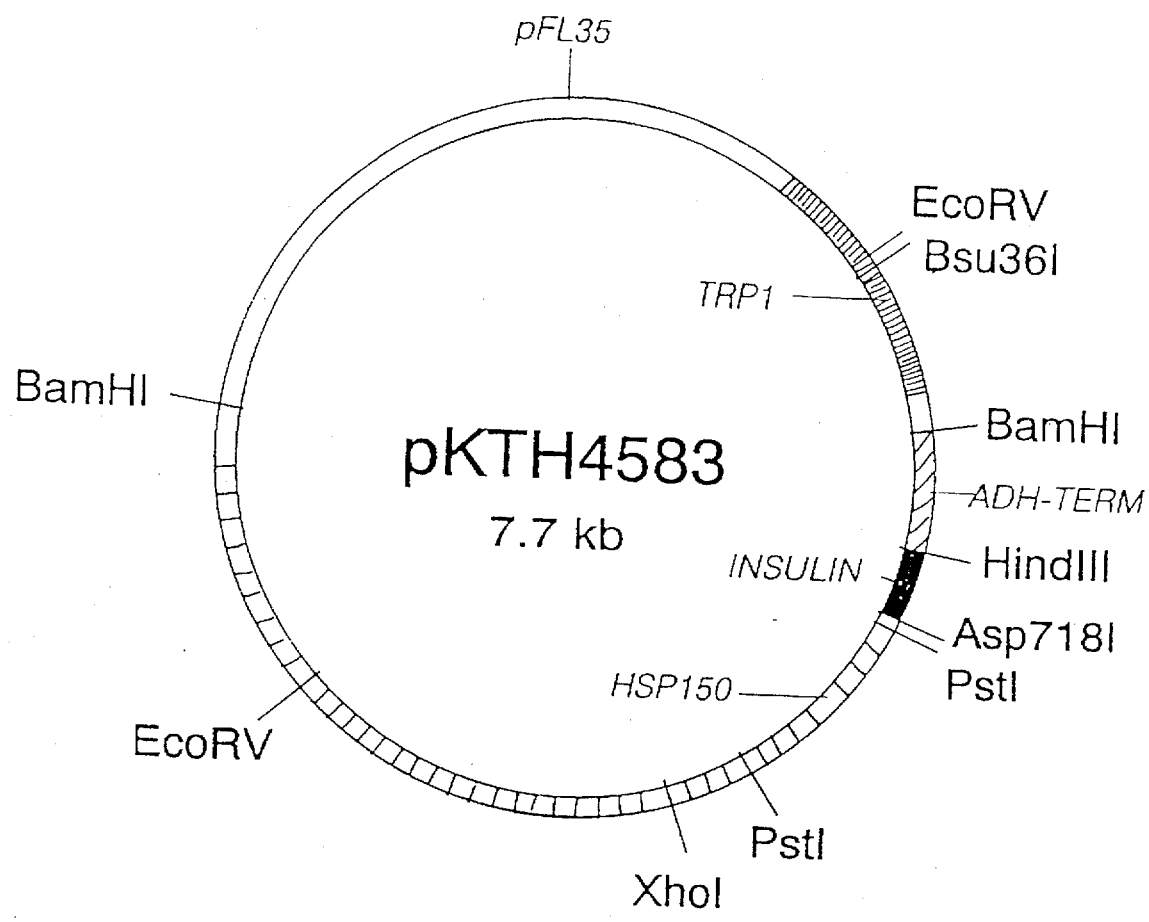

FIG. 21. PLASMID pKTH4583

The HSP150 insulin cDNA fusion was removed by BamHI digestion from plasmid pKTH4581 and ligated to plasmid pFL35 to create pKTH4583.

Figure 22:
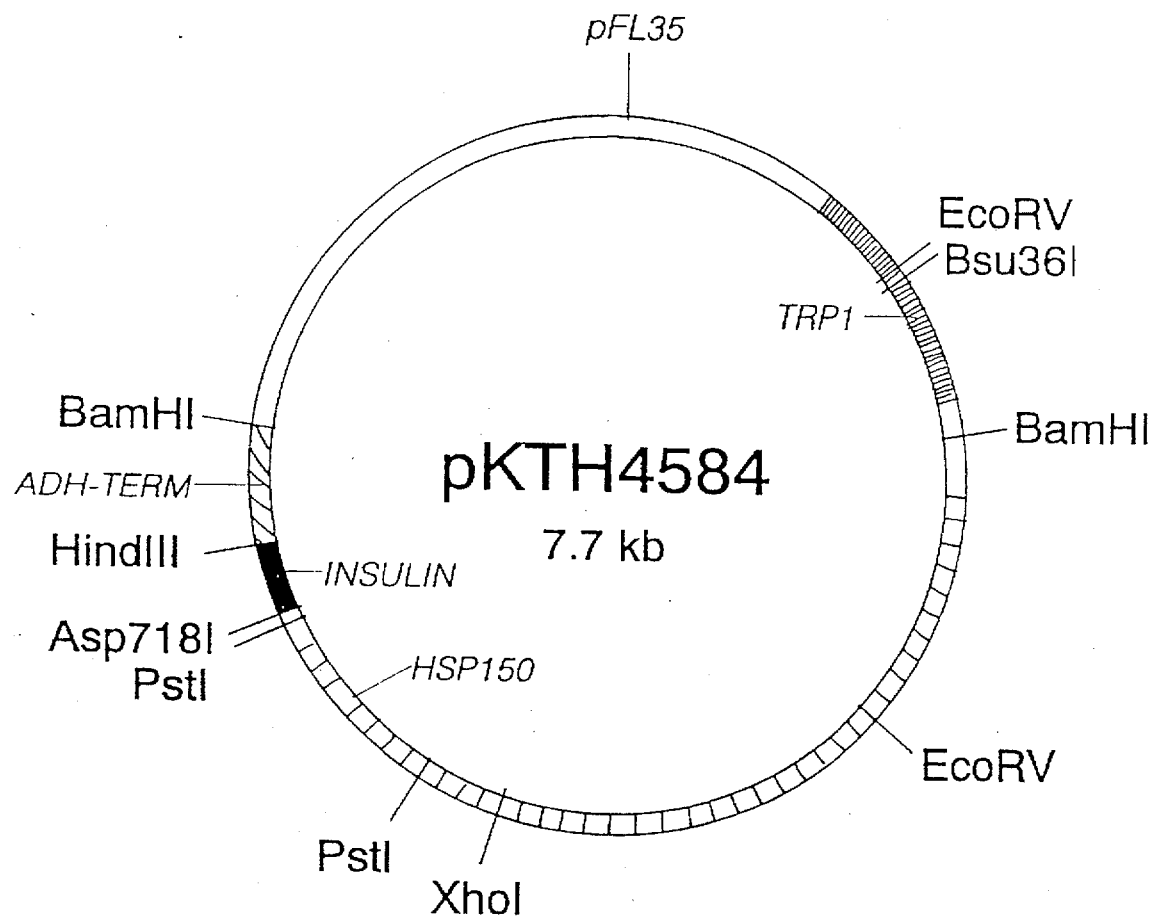

FIG. 22. PLASMID pKTH4584 pKTH4584 is identical to pKTH4583 (FIG. 21), except that the junction between HSP150 and insulin cDNA contains the sequence AAGAGA.

Figure 23:
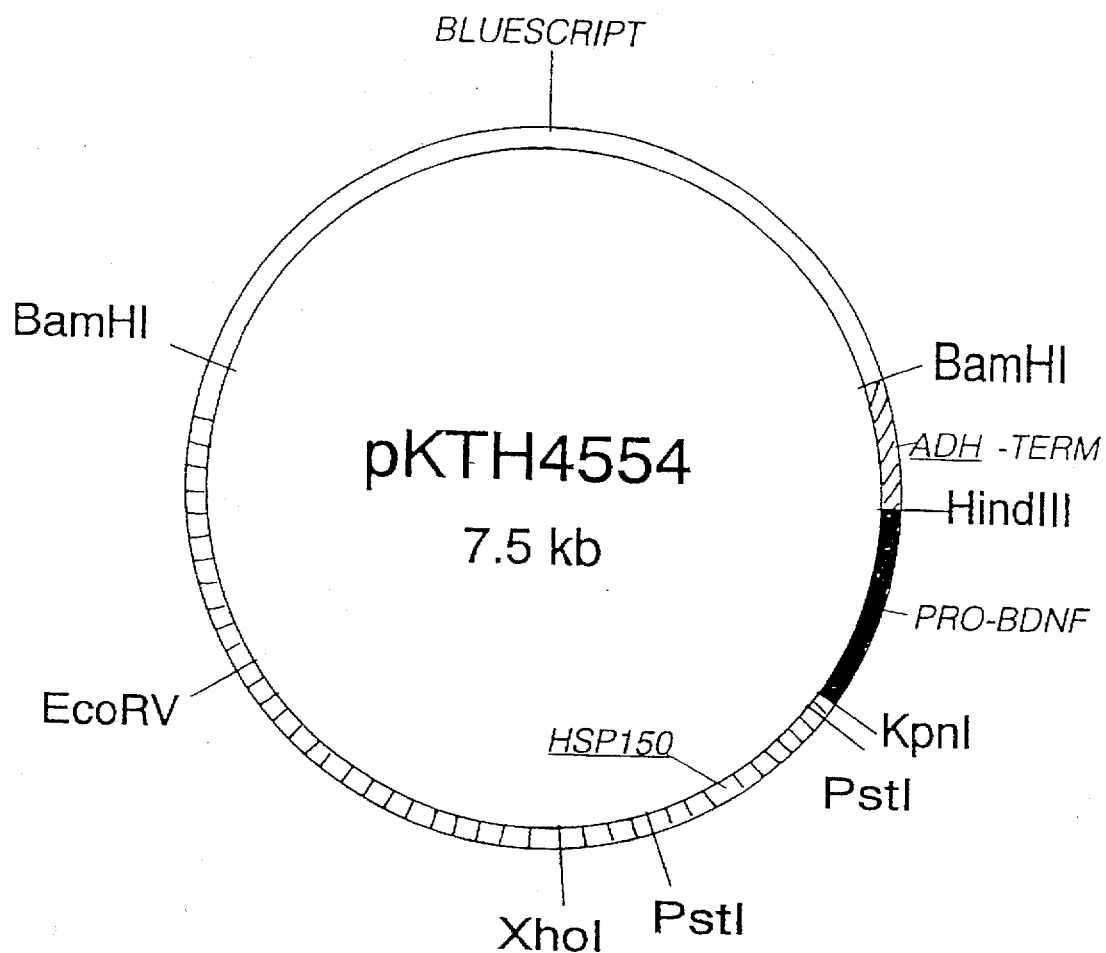

FIG. 23. PLASMID pKTH4554

Pro-BDNF fragment was ligated to the larger fragment of plasmid pKTH4536 (FIG. 9) which had been digested with KpnI and HindIII.

Figure 24:
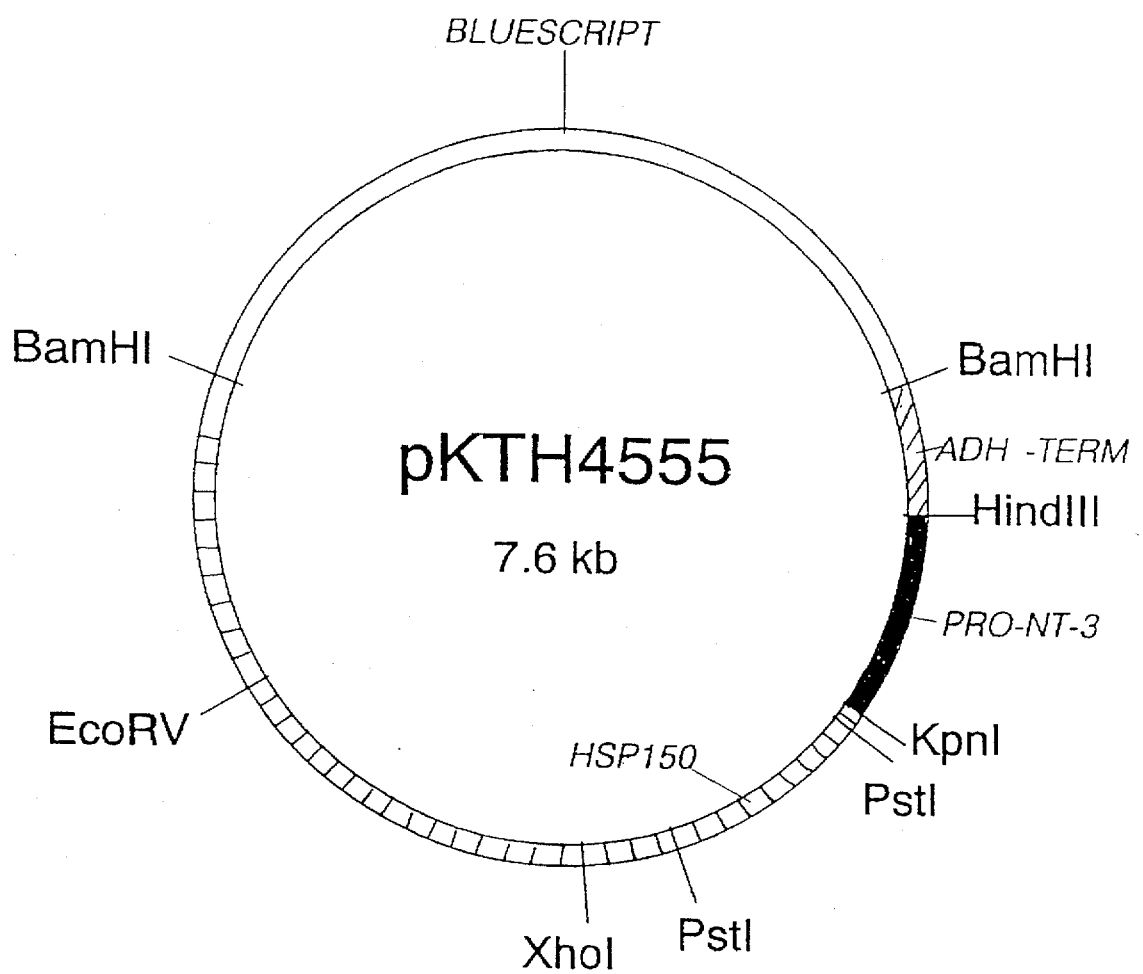

FIG. 24. PLASMID pKTH4555 pKTH4555 is identical to pKTH4554 (FIG. 23), except that the ligated fragment is pro-NT-3.

Figure 25:
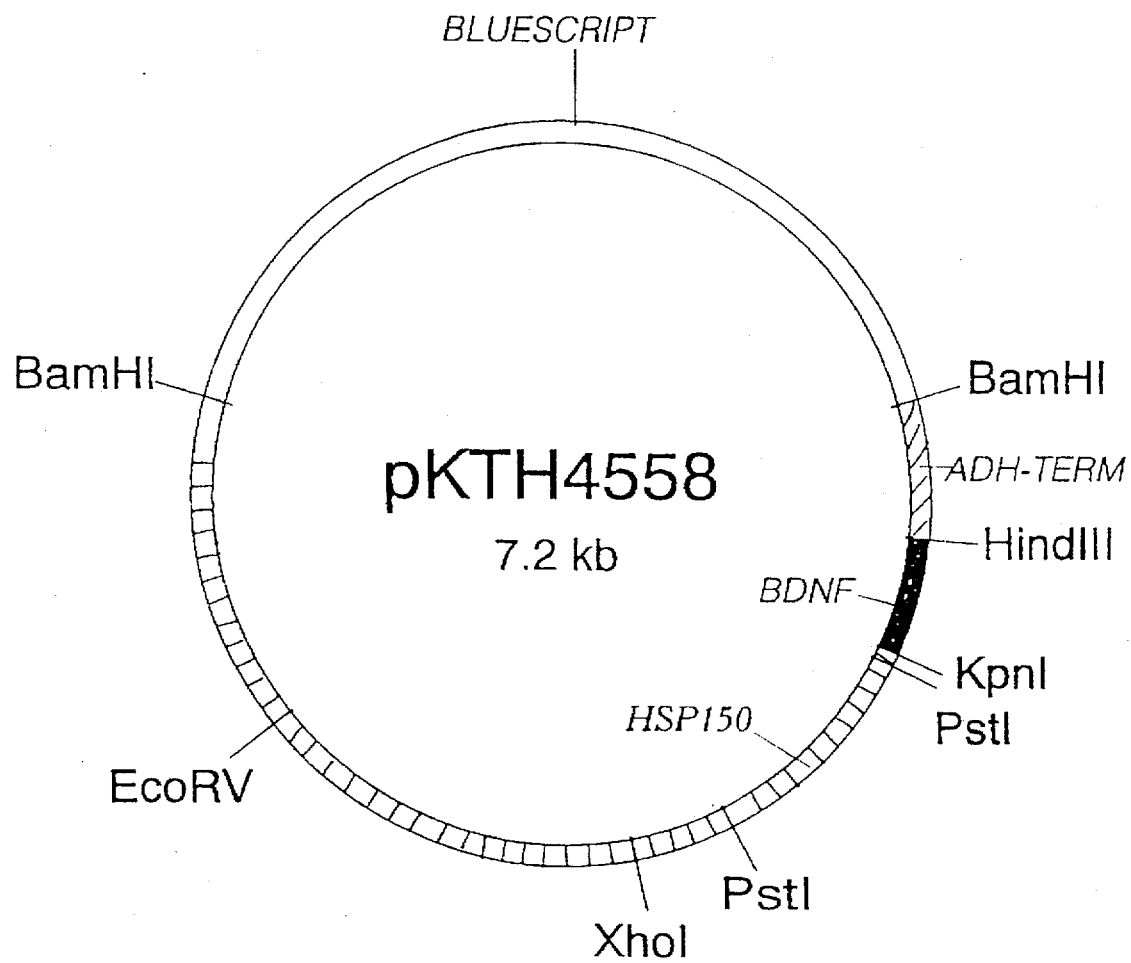

FIG. 25. PLASMID pKTH4558 pKTH4558 is identical to pKTH4554, except that the ligated fragment is BDNF.

Figure 26:
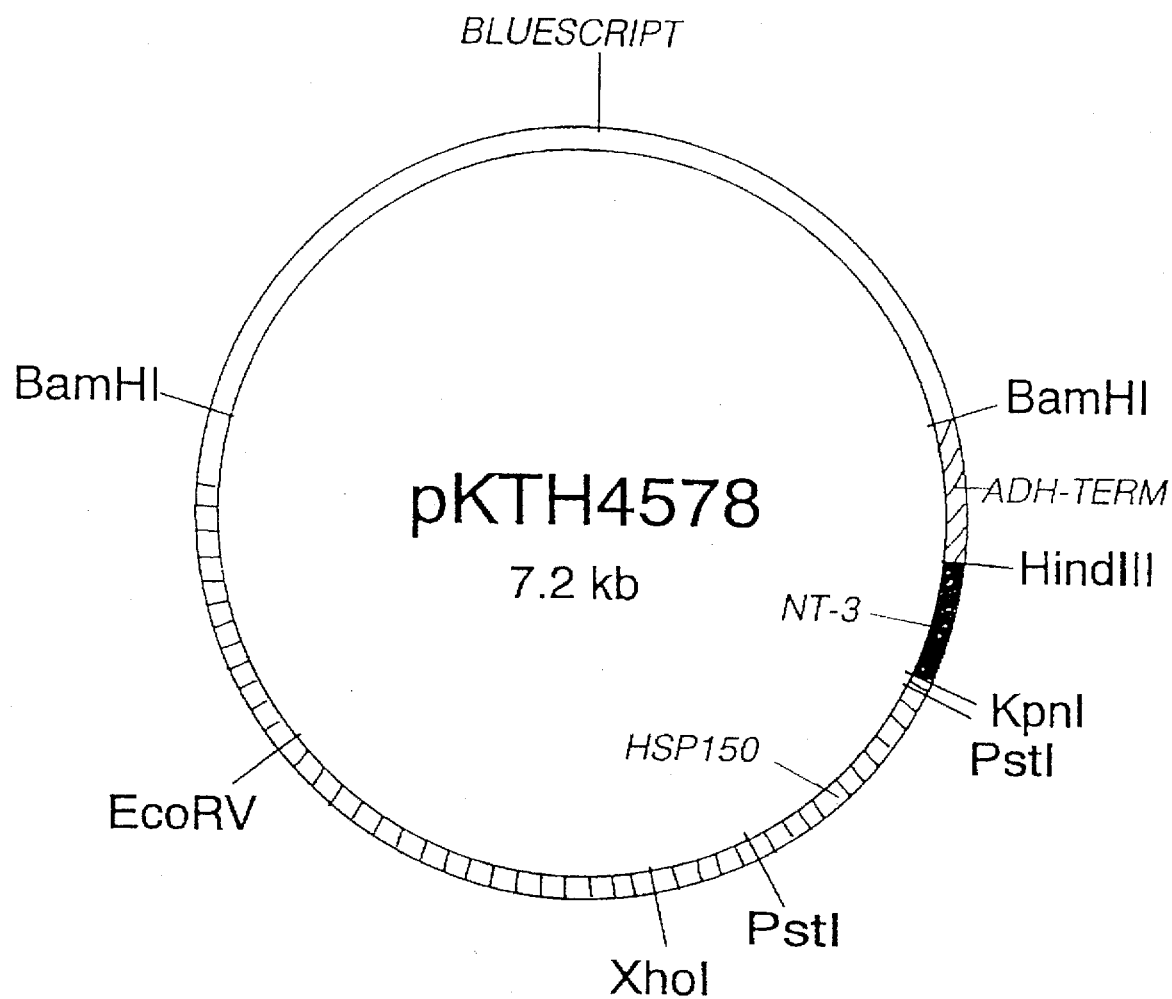

FIG. 26. PLASMID pKTH4578 pKTH4578 is identical to pKTH4554, except that the ligated fragment is NT-3.

Figure 27:
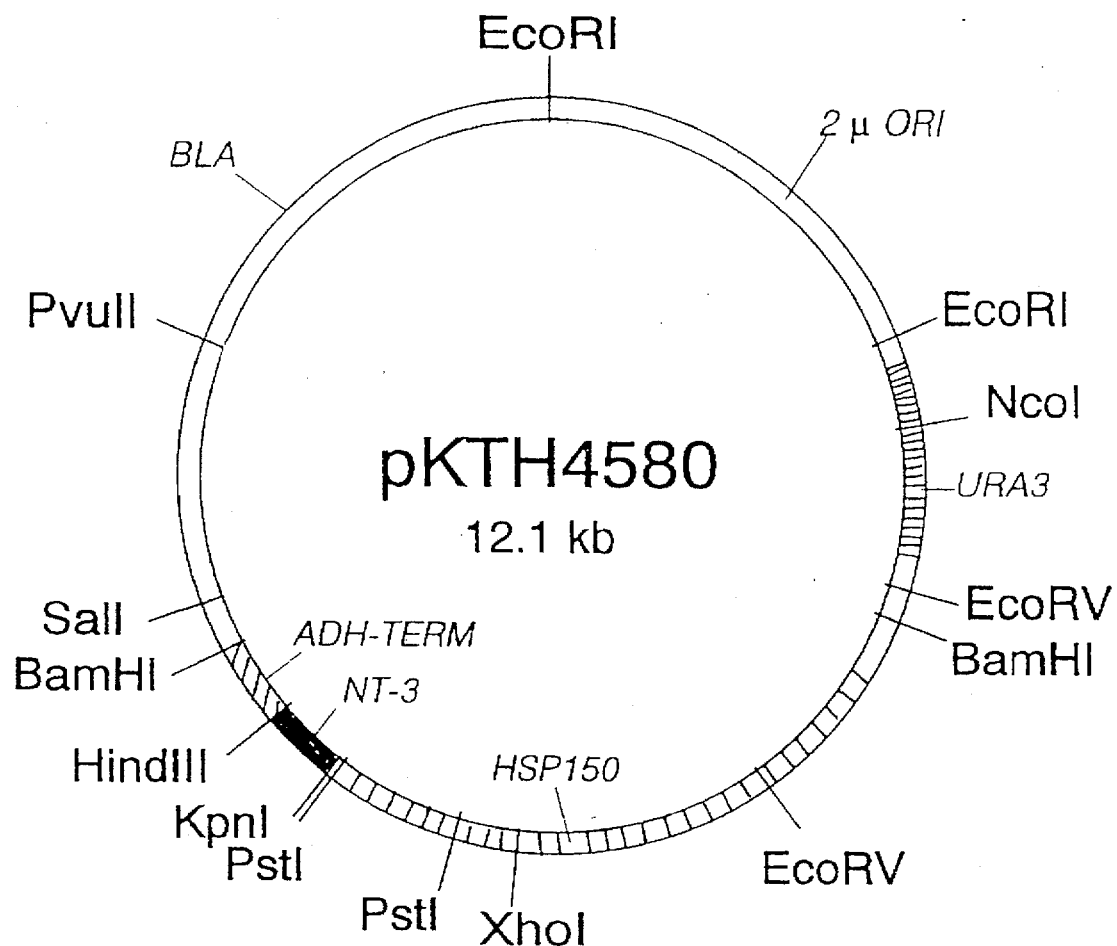

FIG. 27. PLASMID pKTH4580

The HSP150-NT-3 fragment was removed from pKTH4578 (FIG. 26) with BamHI digestion and ligated to the BamHI-site of YEp24.

Figure 28:
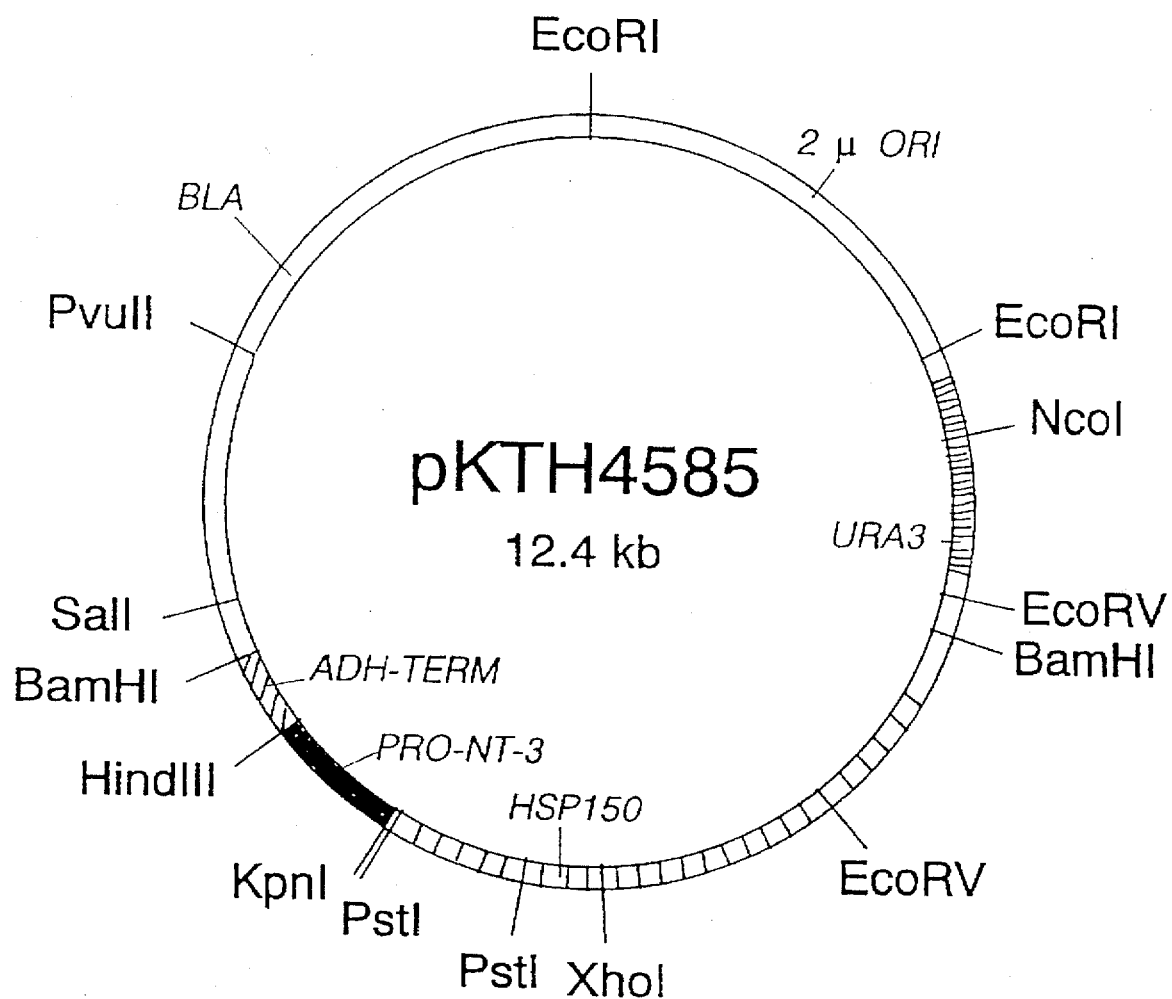

FIG. 28. PLASMID pKTH4585

The HSP150-proNT-3 fragment was removed from pKTH4555 (FIG. 24) and ligated to YEp24 like in FIG. 27.

Figure 29:
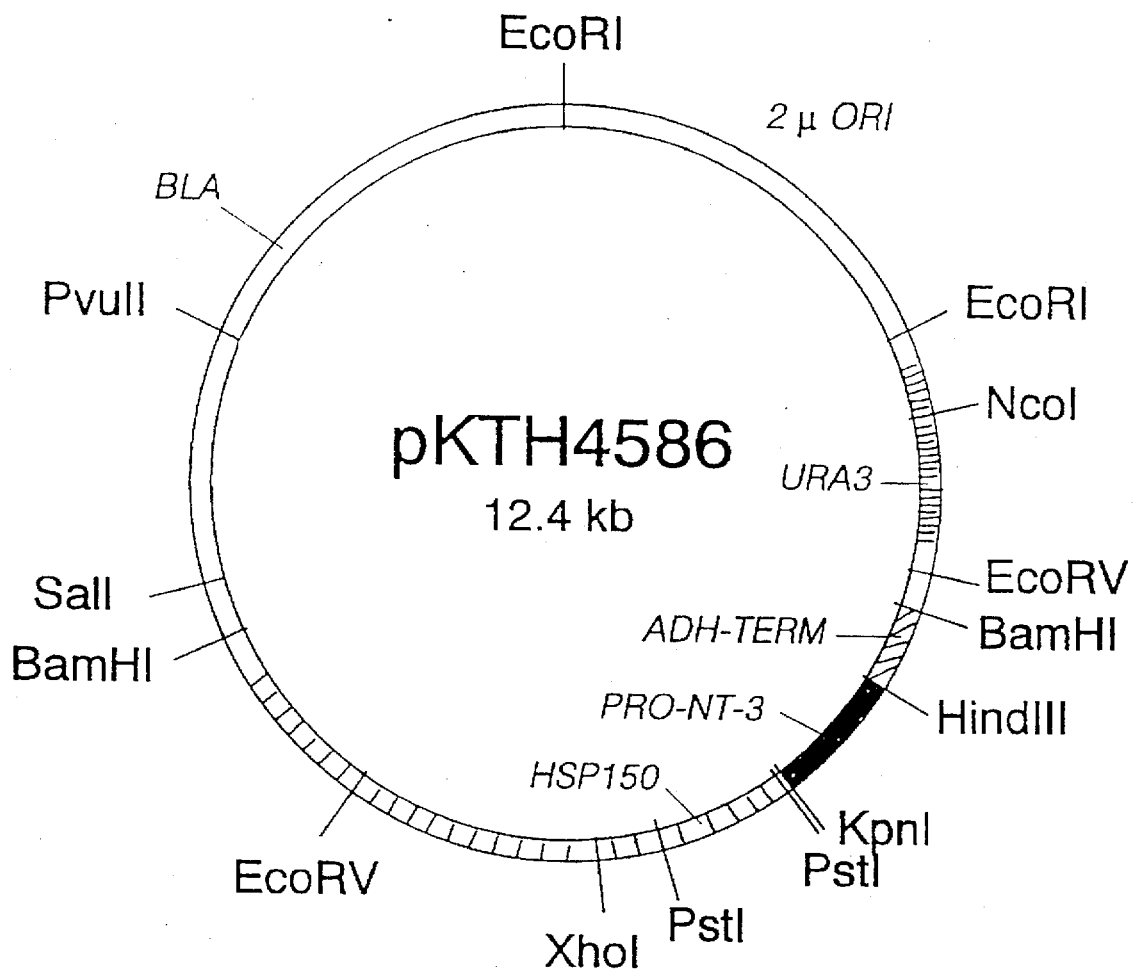

FIG. 29. PLASMID pKTH4586

Identical to pKTH4585 (FIG. 28), except that the HSP150-proNT-3 fragment is in the reverse orientation.

Figure 30:
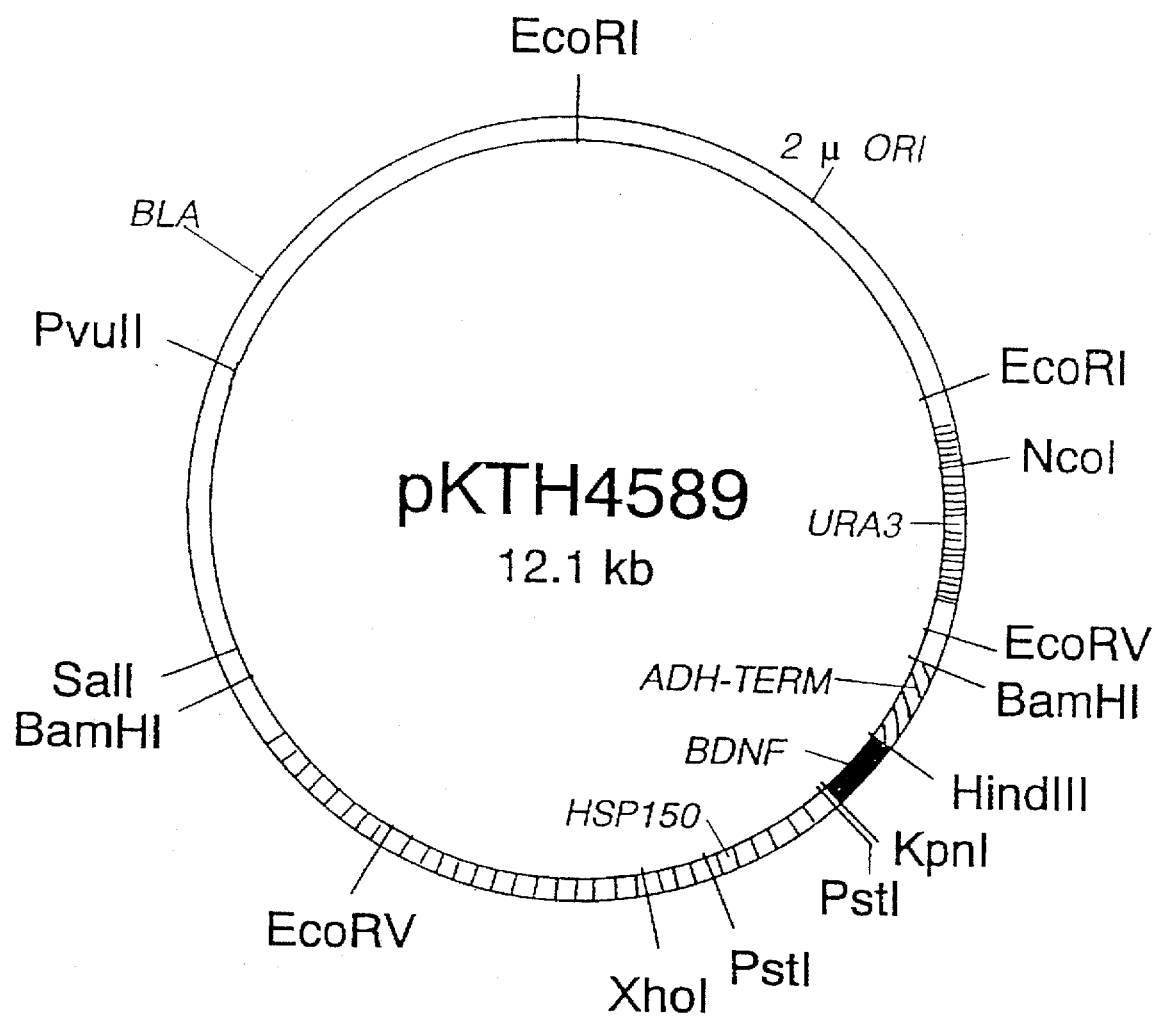

FIG. 30. PLASMID pKTH4589

The HSP150-BDNF fragment was removed from pKTH4558 (FIG. 25) and ligated to YEp24 like in FIG. 27.

Figure 31:
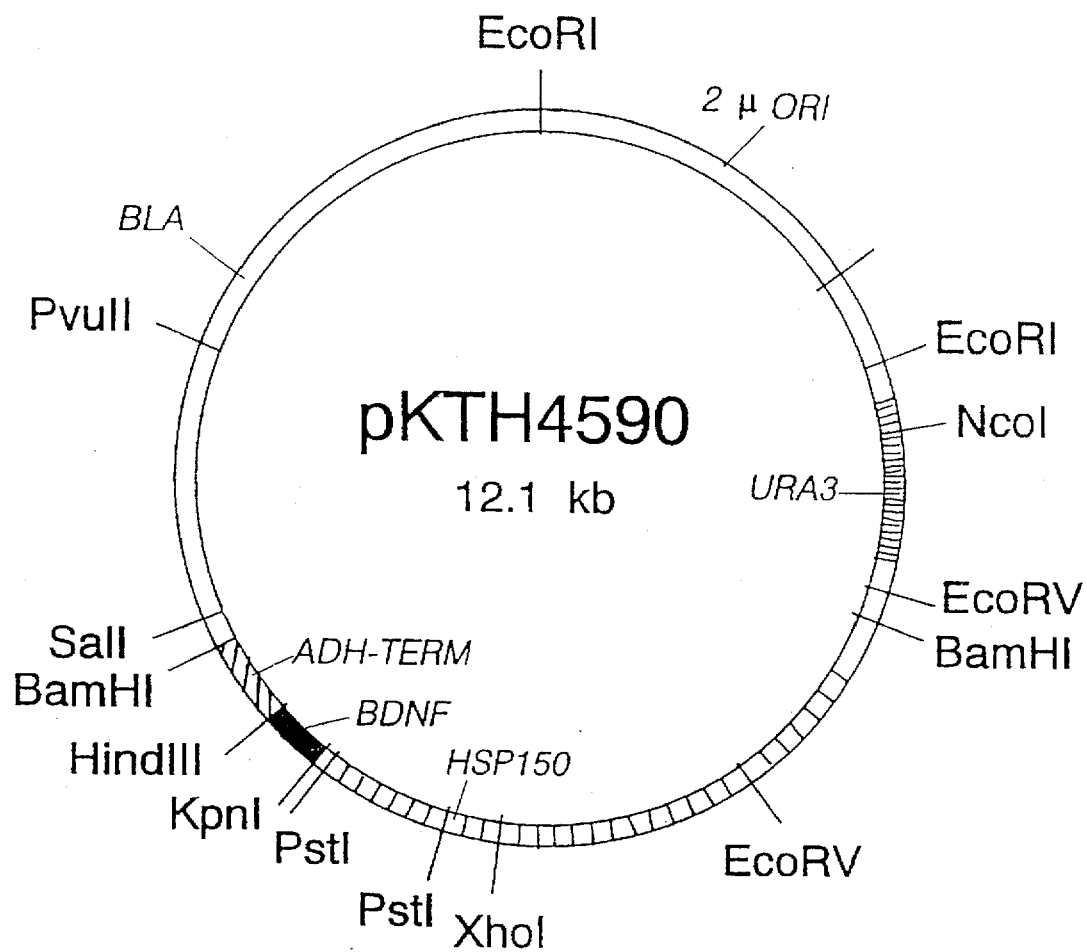

FIG. 31. PLASMID pKTH4590

Identical to pKTH4589 (FIG. 30), except that the HSP150-BDNF fragment is in the reverse orientation.

Figure 32:
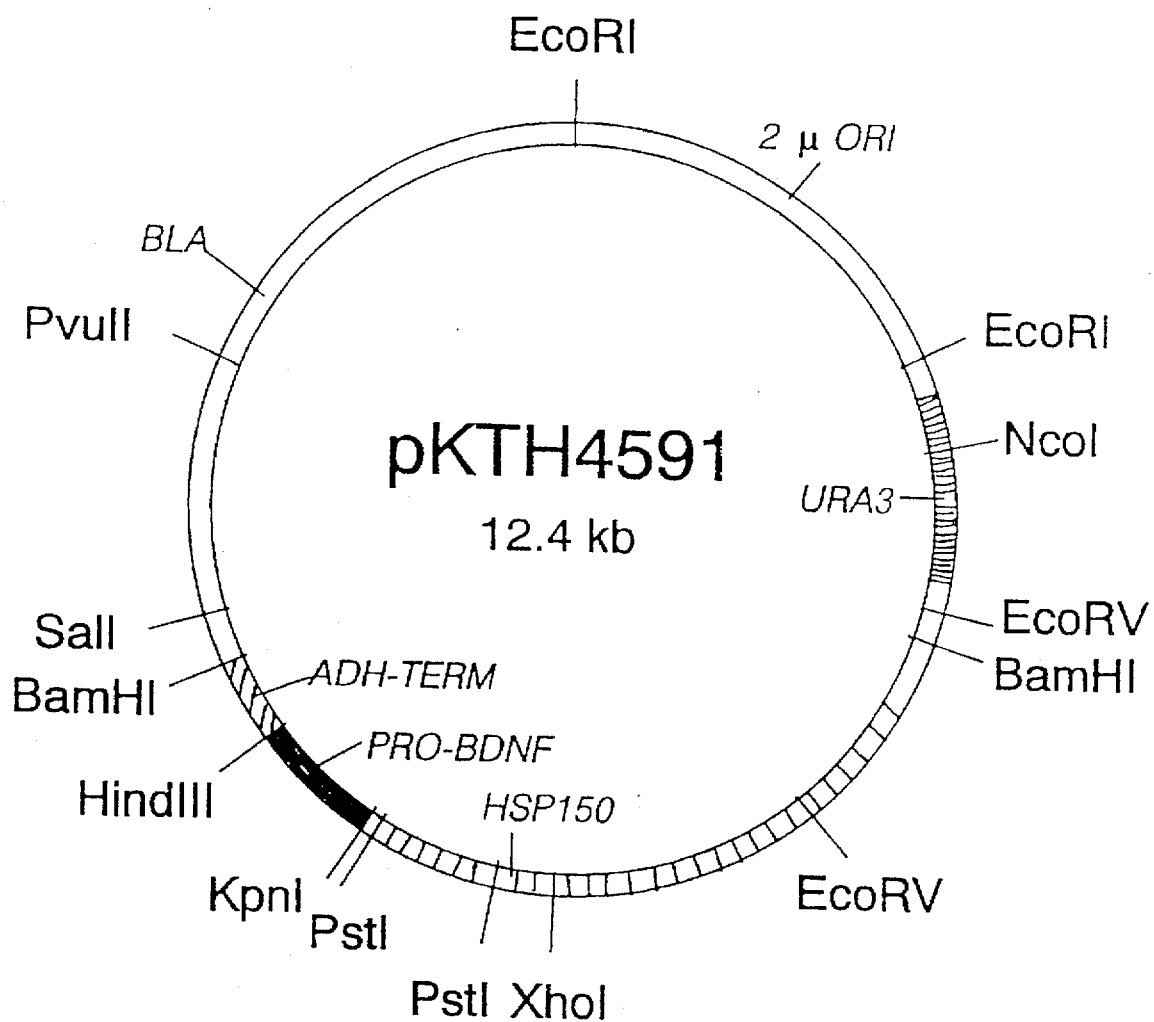

FIG. 32. PLASMID pKTH4591

The HSP150-pro-BDNF fragment was removed from pKTH4554 (FIG. 23) and ligated to YEp24.like in FIG. 27.

Figure 33:
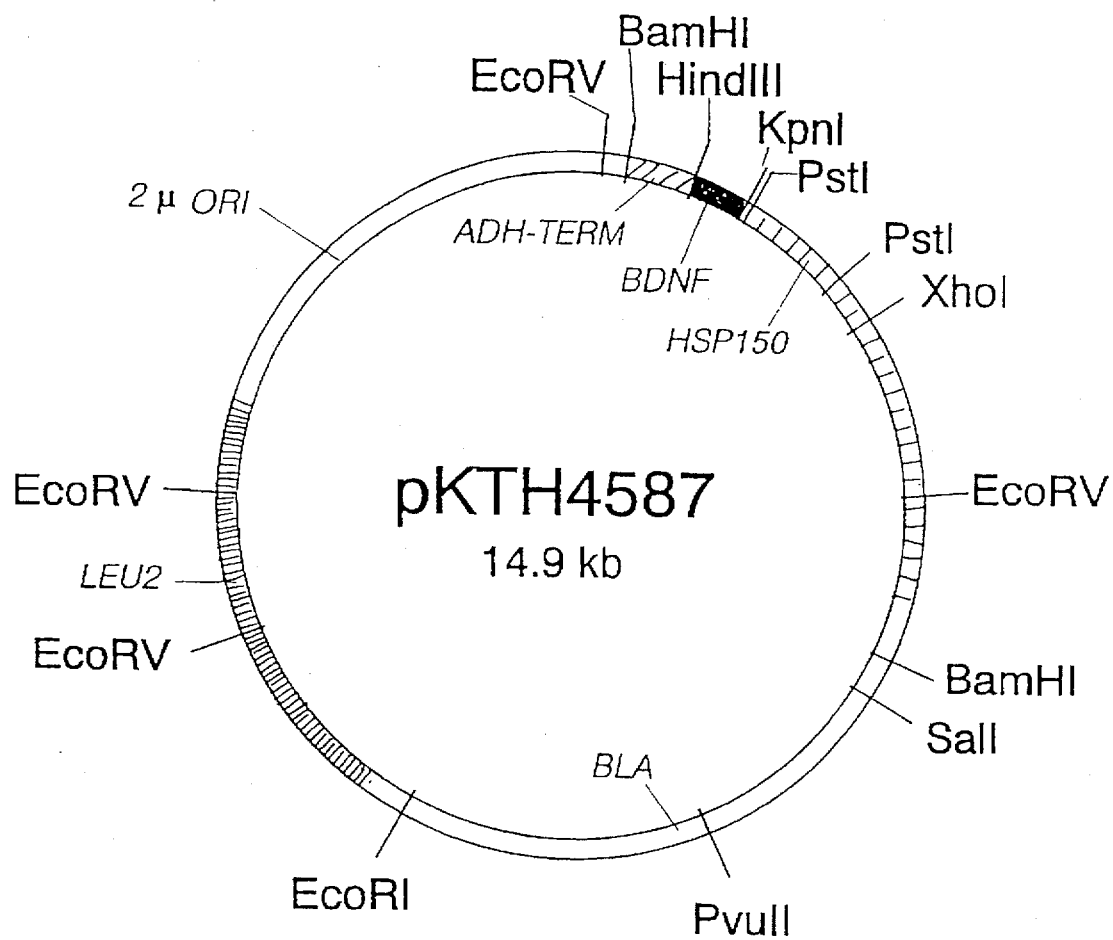

FIG. 33. PLASMID pKTH4587

The HSP150-BDNF fragment of pKTH4558 was ligated to the larger BamHI fragment of pAAH5 (FIG. 8).

Figure 34:
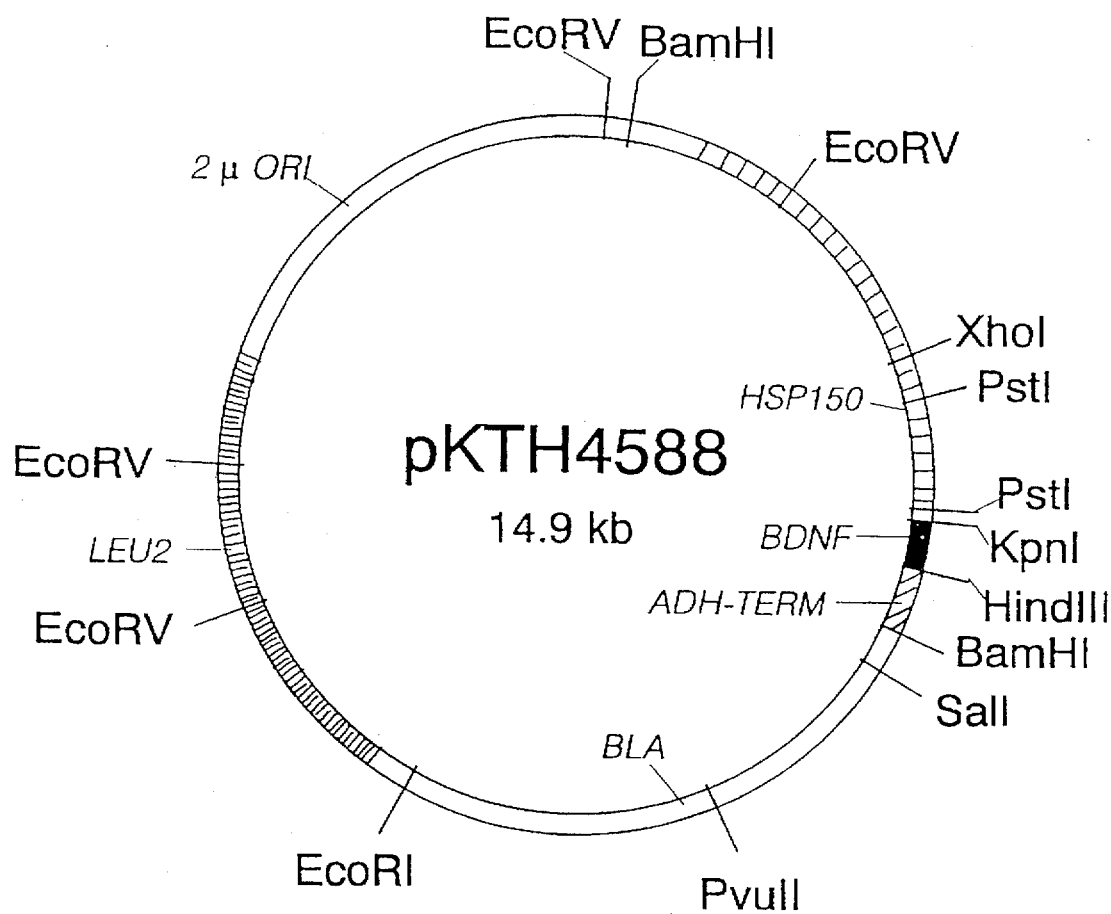

FIG. 34. PLASMID pKTH4588

Identical to pKTH4587 (FIG. 33), except that the HSP150-BDNF fragment is in the reverse orientation.

Figure 35A:
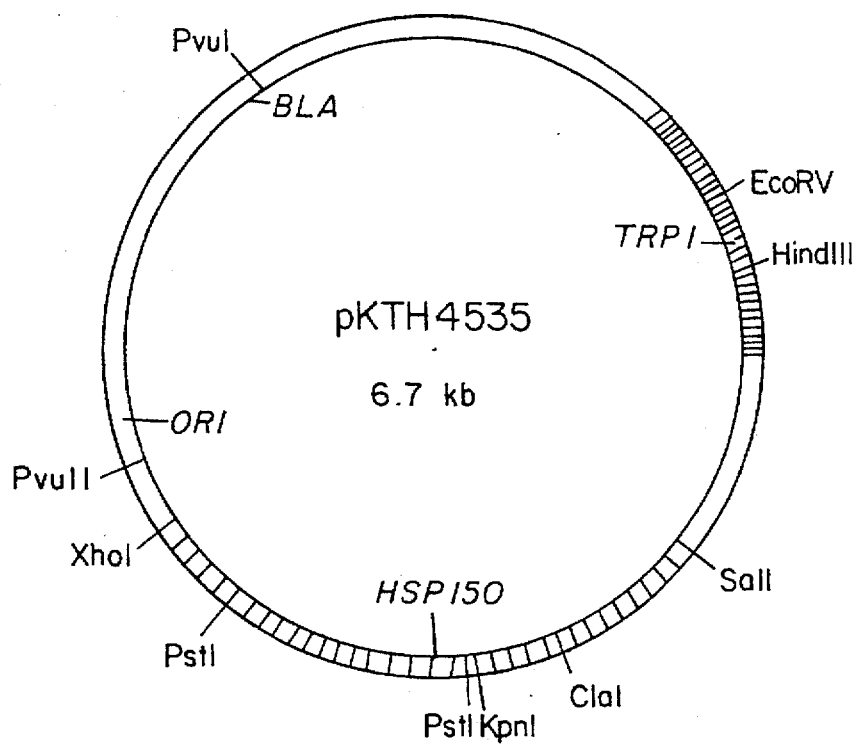
Figure 35B:
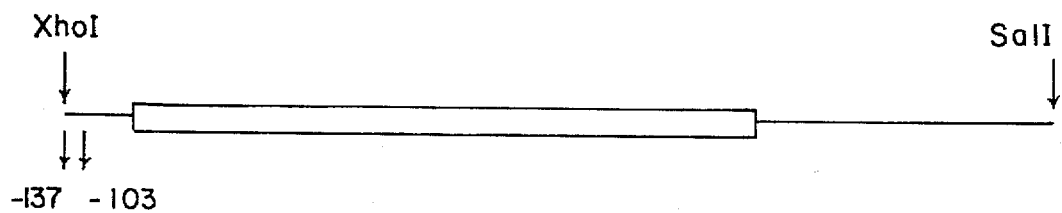

FIGS. 35A and 35B. PLASMIDS pKTH4535 AND pKTH4532

FIG. 35A is a restriction map of pKTH4535. The HSP150 fragment was removed from pKTH4508 (FIG. 5; by digestion with XhoI and SalI, and inserted between the XhoI and SalI sites of pRS414, to create plasmid pKTH4535.

Figure 35C:
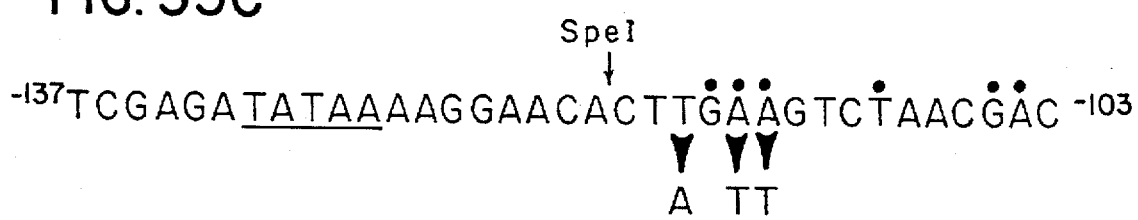

FIG. 35B represents the XhoI-SalI fragment of the HSP150 gene. FIG. 35C shows the sequence from nucleotide −137 to nucleotide −103 of the XhoI-SalI fragment. The dots indicate nucleotides conforming to the consensus heat shock element. This sequence was mutated by changing three nucleotides as indicated, creating a SpeI site. The mutated XhoI-SalI fragment was ligated to pRS414 to create pKTH4532.

EXPERIMENTAL

The following examples further illustrate the invention and should not be considered to restrict the invention. Throughout, general methods of molecular biology have been used, unless otherwise stated.

The restriction endonucleases were from New England Biolabs, Boehringer Mannheim and Promega, and they were used according to manufacturers' instructions. T4 DNA ligase was from Promega and and it was used according to Promega's instructions. The Bluescript II SK$^+$-vector was from Stratagene. DNA polymerase I (Klenow enzyme) was from Promega and it was used as described in the Cold Spring Harbor handbook (Sambrook et al., Molecular Cloning, 1989). The radioactive nucleotides dATP and dCTP were from Amersham. DNA sequencing was carried out by the dideoxy-chain termination method using 35S-dATP (Amersham), and either the CircumVent™ DNA Sequencing Kit (New England Biolabs) or the Multiwell microtitre plate DNA sequencing system (Amersham). E. coli was transformed according to Hanahan (J. Mol. Biol. 166:557–580, 1983). S. cerevisiae cells were transformed using the lithium acetate method (Ito et al., J. Bacteriol. 153:163–171, 1983), or electroporation (Becker and Guarante, Meth. Enzymol. 194:182–187, 1991). The phenol and ether extractions, ethanol precipitations and DNA isolations from E. coli were performed according to the Molecular Cloning handbook. The DNA fragments were eluted from agarose gel slices by crushing them carefully with a glass rod in Eppendorf tubes. The agarose bits were flushed from the rod with 200 μl of TE (10 mM Tris-HCl pH 8.0, 1 mM EDTA). After mixing, 400–500 μl of neutralized phenol was added and the mixture was vortexed vigorously for 1 min, and the tube was transferred immediately to liquid nitrogen. After 1 min, the suspension was centrifuged for 15 min at room temperature. The agarose, which settled at the bottom of the tube, was covered with the phenol phase, which in turn was covered with the aqueous phase containing the DNA. The aqueous phase was removed and treated with phenol, which was then removed by ether extraction. The DNA was precipitated with ethanol. The oligonucleotides were synthesized in the DNA-laboratory of the Institute of Biotechnology, University of Helsinki.

EXAMPLE 1

The HSP150 Gene and the hsp150 Protein

Purification and Amino Acid Sequencing of the hsp150 Protein.

The S. cerevisiae strain H3 (for list of strains, see Table 2) was grown in YPD-medium [1% yeast extract (Oxoid Ltd., Basingstoke, England, 2% bacto peptone (Difco, Detroit, USA), 2% glucose (BDH Pharmaceuticals Ltd., UK)] overnight at 25° C. to a density of about $25 \times 10^6$ cells/ml. The cell suspension was shifted for 15 min to 37° C., the cells were then collected by centrifugation and resuspended to a density of about $5 \times 10^{11}$ cells/l of fresh YPD-medium, prewarmed to 37° C. The cells were incubated for 1 h at 37° C., NaN$_3$ was added to a final concentration of 10 mM, and the suspension was filtered through a Seitz-filter. The growth medium was concentrated using a Romicon (Amicon) ultra-filtrator and precipitated with 60% ammonium sulphate. The precipitate was dialyzed against sterilized distilled water for 48 h. The dialyzate was concentrated by lyophilization, and passed over a Bio-Gel P-200 column, eluted with 20mMTris-HCl pH 7.6. The void volume fractions were pooled and passed over a Mono Q-column, eluted with 0–60% NaCl-gragient in 20 mM Tris-HCl pH 7.6. The hsp150 protein was detected from the fractions with Western analysis, where the proteins after SDS-polyacrylamide gel electrophoresis (Laemmli, Nature 227:680–685, 1970) were transferred to nitrocellulose membrane (Towbin et al., PNAS 76:4350–4354, 1979), and immunostained using anti-hsp150 antiserum (1:1500 dilution) and anti-rabbit IgG-conjugated alkaline phosphatase. The conjugate and the phosphatase substrates NBT and BCIP were from Promega and they were used according to Promega's instructions.

The purified hsp150 protein was digested with trypsin, and the peptides were resolved with reversed phase chromatography. Seven peptide sequences were determined with an automatic gas phase sequencer, attached to an on-line PTH-amino acid analyzer (Kalkkinen and Tilgman, J. Prot. Chem. 7:242–243, 1988).

Cloning and Characterization of the HSP150 Gene

Figure 4A:
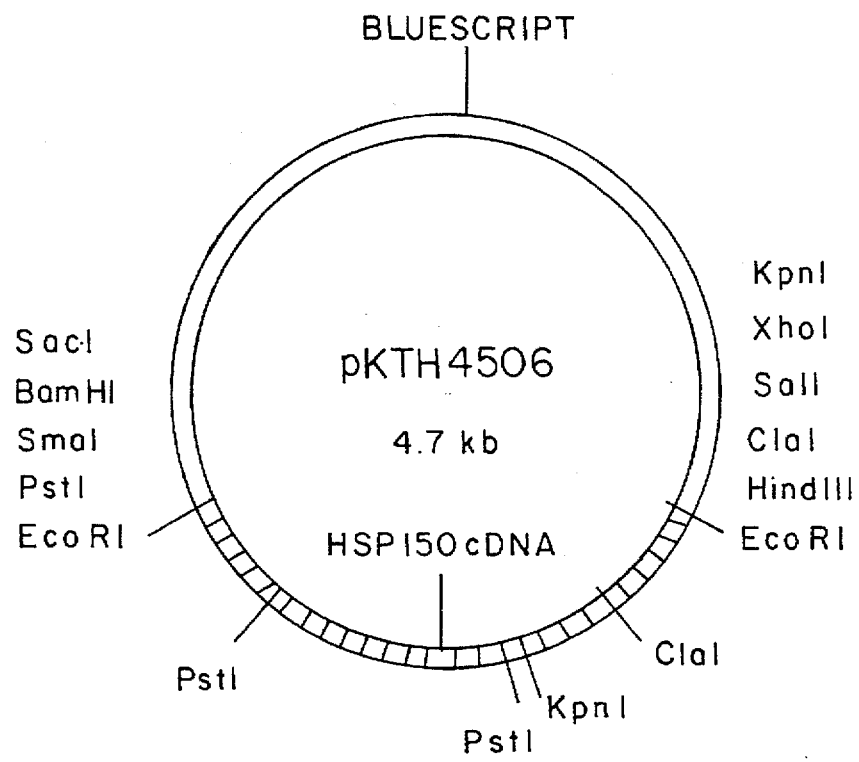
FIGS. 4A and 4B PLASMIDS pKTH4506 AND pKTH4507
Figure 4B:
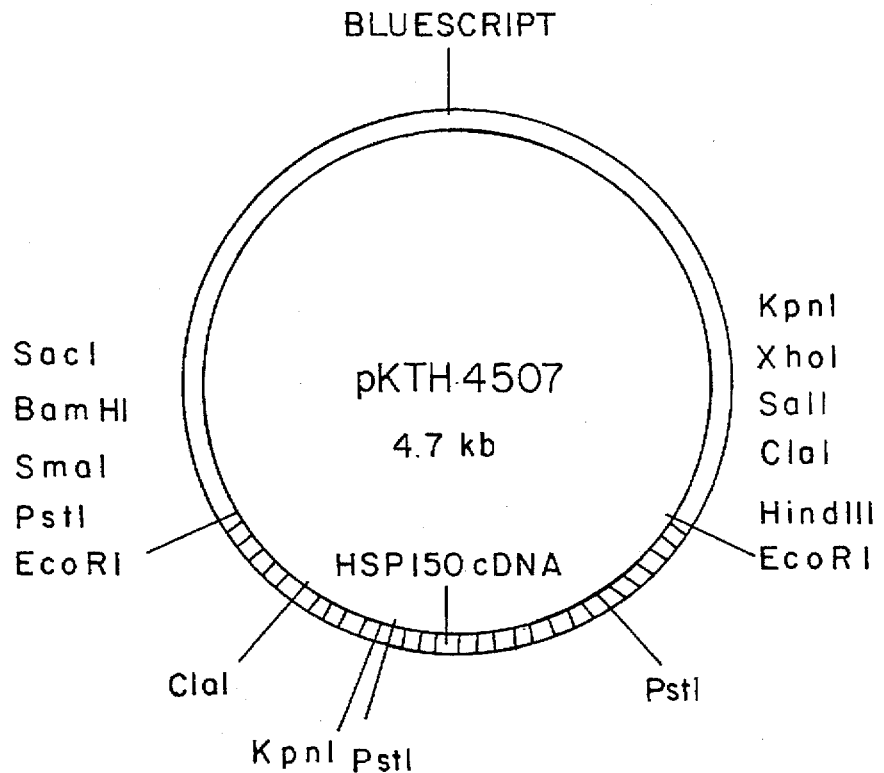

The HSP150 gene was cloned using oligonucleotide screening. The oligonucleotide T8977 (38 nucleotides, Table 1) was synthesized according to the sequence of peptide 5 (see FIGS. 1A–1C), and labeled with $\gamma$-$^{32}$P-ATP using T4 polynucleotide kinase (Sambrook et al., Molecular Cloning, 1989). Over 300,000 plaques of the S. cerevisiae cDNA $\lambda$gt11-library (Benton and Davis, Science 196:180–182, 1977) were screened with the probe. Two positive DNA fragments were cloned into the Bluescript II SK$^+$-vector (Stratagene), and their both strands were sequenced (Sanger et al., PNAS 74:5463–5467, 1977). These plasmids were named pKTH4506 and pKTH4507, and they differed from each other only by orientation (FIGS. 4A and 4B). The HSP150 structural gene extends from nucleotide +1 to ++1239, and encodes the amino acid sequence 1–413.

The Structure of the hsp150 Protein

Figures 2A, 2B:
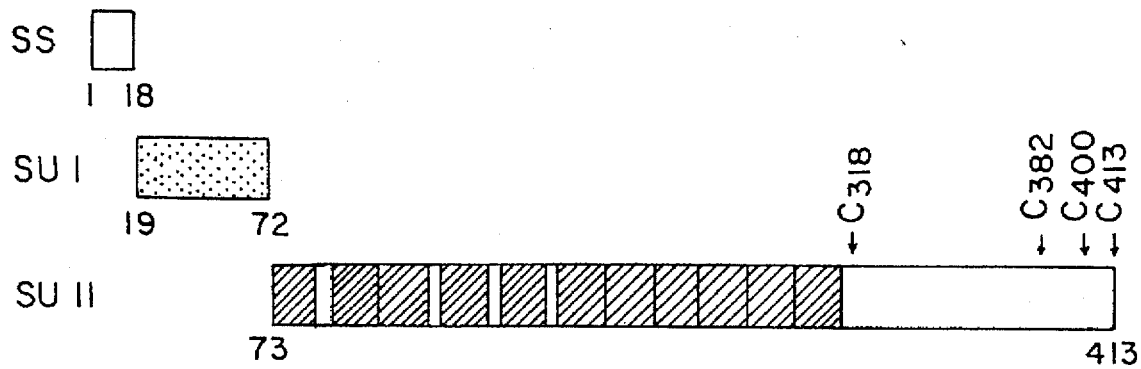
FIGS. 2A and 2B. THE hsp150 PROTEIN

The primary translation product of 413 amino acids of the HSP150 gene starts with an N-terminal signal sequence of 18 amino acids, which resembles the signal sequences of other secretory proteins of yeast, due to the pair of basic amino acids Lys$_4$-Lys$_5$ at the N-end, hydrophobic amino acids in the core-region, and small apolar amino acids Thr$_{16}$ and Ala$_{18}$ at the cleavage site. Direct N-terminal amino acid sequencing of purified hsp15 protein revealed two different N-termini in equimo! ar rati (underlined sequences 1 and 2, FIGS. 1A–1C). This shows that the signal sequence is removed, and that the polypeptide chain is cleaved between Arg$_{72}$ and Ala$_{73}$, resulting in subunit I of 54 amino acids and subunit II of 341 amino acids. The cleavage site is a recognition site of the kex2 protease due to the Lys$_{71}$-Arg$_{72}$ pair. About two thirds of subunit II consist of a 19 amino acid peptide which is repeated 11 times. Between some of tile peptides there is a spacer, but in most cases they are joined head-to-tail. The repetitive peptides are conserved, displaying only few nonconservative amino acid changes (FIGS. 2A and 2B). The consensus repetitive peptide (lines 6 and 9 in FIG. 2B) was synthesized and subjected to nuclear magnetic resonance spectrometry. All amino acids interacted only with those amino acids with which they formed peptide bonds. Thus, the peptide had no conformation but occured as a random coil. Subunit II was purified as described above and subjected to circular dichroism analysis. Most of subunit II had no conformation. Thus, at least the repetitive region of subunit II appears to be an unstructured random coil.

The Control Elements of the HSP150 Gene

For the characterization of the regulatory elements, HSP150 was cloned from the genomic library of S. cerevisiae (Carlson and Botstein, Cell 28:145–154, 1982), using the HSP150 cDNA, labeled with the random primer technique (Feinberg and Vogelstein, Anal. Biochem. 132:6–13, 1983), with $\alpha$-$^{32}$P-dCTP using the Multiprime DNA Labelling System (Amersham). Two positive clones with identical restriction maps were picked up. They were named pKTH4508 and pKTH4509. pKTH4508 (FIG. 5) was subcloned and sequenced. The coding region and the upstream and downstream flanking sequences were sequenced from both strands. 396 nucleotides upstream from the initiation codon ATG were sequenced. The open reading frame begins at nucleotide +1 and continues to the 3' direction to nucleotide +1239. Downstream from the structural gene, 413 nucleotides were sequenced. The genetic sequence HSP150, extending at the 5'-end from nucleotide –396 to the 3'-end to nucleotide +1652 is presented in SEQ ID No. 1 and in FIGS. 1A–1C.

The regulation of the HSP150 gene occurs at the transcriptional level, because the amount of the HSP150 mRNA increases after heat shock, as determined by Northern blot analysis. Northern analysis was performed by resolving S. cerevisiae total RNA by formaldehyde gel electrophoresis and transferring it to nylon membrane (Sherman et al., Laboratory Manual for Methods in Yeast Genetics, Cold Spring Harbor, N.Y., 1986). The membrane was hybridized overnight at 42° C. with the HSP150 cDNA clone, used before in the screening of the genomic library. Upstream from the structural gene, there is a TATA-element at position (–127)–(–131), and heat promoter-like sequences (HSE) at positions (–103)–(–115), (–185)–(–197), (–162)–(–174) and (–269)–(–282) (FIGS. 1A–1C). The TATA-element is responsible for the basic expression of most genes (Hahn et al., PNAS 86:5718–5722, 1989). The TATA-like element of HSP150 appears to be functional, since a construction (pKTH4535, FIGS. 35A–35C) having only 137 base pairs of upstream sequence, expresses HSP150 mRNA (FIGS. 1A–1C and 3A–3C).

A functional HSE consists of at least three alternating GAA and TTC motifs, punctuated by two nucleotides (Amin et al., Mol. Cell. Biol. 8:3761–3769, 1988). Many S. cerevisiae heat shock genes have been shown to have HSEs which deviate from the consensus HSE. The HSE-like sequence $_{-115}$CGAAGTCTAACGACA$_{-103}$ (SEQ. ID. NO.:1, residues 282–295), or a sequence overlapping it, is enough to confer heat-regulation to HSP150, because a construction having only the first 137 base pairs upstream from ATG expressed HSP150 mRNA in a heat-dependent fashion (strain H286, transformed with pKTH4535). When A$_{-114}$ and A$_{-113}$ were mutagenized to thymidines, and T$_{-116}$ to adenine, creating strain H314, the constitutive level of transcription at 24° C. was substantially increased, whereas shift of cells to 37° C. decreased transcription. The XhoI-SalI fragment of pKTH4508 (FIG. 5) was inserted between the XhoI and SalI sites of pRS414, and used to transform strain H23 to create strain H286.

A mutagenic oligonucleotide 91604 (Table 1) was prepared to destroy the single HSE-like sequence of the HSP150 gene in pKTH4535. A mutated HSP150 gene was obtained by PCR using 91604 as the mutagenic 5' primer and 9175 (Table 1) as the 3' primer. The 3' primer hybridizes to sequences 412 bp downstream of HSP150 stop codon. The template was pKTH4530 (FIGS. 7A and 7B) digested with SalI.

The PCR reaction was performed with 2.5 U of pfu-polymerase (Stratagene) in a volume of 50 μl. The concentration of the primers was 1 μM and that of the nucleotides 200 μM, and buffer #1 was from Stratagene. Denaturation was performed at 95° C. for 30 sec, annealing at 50° C. for 1 min and elongation at 72° C. for 3 min. The cycle was repeated 30 times. A DNA fragment of expected length (1787 bp) was obtained. The single stranded ends of the DNA fragment were removed with mung bean nuclease (Boehringer Mannheim), and the 5' end of the fragment was digested with XhoI. The fragment thus obtained was ligated to pRS414 that had been digested with XhoI and SmaI. The plasmid thus obtained was designated pKTH4532 (FIG. 35B). The correctness of pKTH4532 and the presence of the desired mutation was confirmed by restriction analysis and sequencing. pKTH4532 is similar to pKTH4535, except that the HSE-like sequence has been mutated and the 3' flanking region of HSP150 is 158 bp shorter.

The promoter region of HSP150 includes even an element which responds to nutrient starvation. When strain H314, grown overnight at 24° C. was incubated for 2 h at 24° C. in nitrogen starvation medium (synthetic complete medium according to Sherman, Meth. Enzymol. 194:3–20, 1991, lacking ammonium sulfate and amino acids), transcription of HSP150 mRNA was activated, as determined by Northern blotting performed as described above.

There are two transcription termination signals, TATATA (Russo et al., EMBO J. 10:563–571, 1991) and TTTTTTT-TATA (Henikoff and Cohen, Mol. Cell. Biol. 4:1515–1520), downstream from the structural gene (FIGS. 1A–1C).

Conservation of the HSP150 Gene

Heat-regulated antigenic homologs of the S. cerevisiae hsp150 protein were found by Western blotting, using anti-hsp150 antiserum, in Torulaspora delbrueckii, Kluyveromyces marxianus (NCYC587) and Schizosaccharomyces pombe (h⁻ leu1-32), suggesting that the hsp150 protein is conserved in very divergent yeasts.

A HSP150 homolog gene of S. pombe was searched as follows. An S. pombe cDNA library in kgtll was obtained from Dr. Altman (Institut fuer Biochemie, Bern, Switzerland). It was used to infect E. coli Y1090. The infected cells were plated and plaques were transferred onto duplicate Hybond N-membranes (Amersham). The plaques were sceened by hybridization with a $^{32}$P-dCTP-labelled probe prepared from the 1.7 kb HSP150 cDNA obtained from plasmid pKTH4506 (FIG. 4A).

Hybridization was performed in 5×SSC containing 5×Denhardt's solution, 50 mM potassium phosphate buffer pH 7, 200 μg/ml of herring sperm DNA and 106 cpm of radiolabeled probe/ml, as follows. The temperature was 65° C. for 3 h, and then it was allowed to decrease overnight to 37° C. The membrane was washed prior to exposure at 42° C. in 2×SSC containing 0.1% SDS. According to the present invention, the term "hybridization" means conventional hybridization conditions, preferably those described above for the cloning of HSP150 homologs in other yeasts.

Three positive clones were isolated and the λ-DNA was purified from them. They all contained an EcoRI insert of about 3 kb. The fragments were cloned into the EcoRI site of pUC19. DNA was isolated from transformants with inserts, digested with EcoRI and HindIII. The digestion patterns of the transformants were identical. The digested DNAs were hybridized with the HSP150 cDNA probe like before. The results showed that the hybridizing DNA indeed was the 3 kb EcoRI insert and not the vector DNA.

Secretion of hsp150

Secretion of hsp150 protein expressed from the chromosomal HSP150 gene was studied in immunoprecipitation experiments in the following way. Strain H1 was grown at 25° C. overnight in YPD-medium. 2×10⁸ cells were pelleted and resuspended in 400 μl of fresh YPD-medium and 50 μCi of $^{35}$S-methionine was added. The cells were labeled for 1 h at 25° C. or 37° C. Labeling was terminated by adding NaN₃ to 10 mM, the cells were pelleted and the supernatant was removed. A parallel similarly labeled cell sample was not treated with NaN₃ but pelleted and resuspended in 400 μl of fresh YPD-medium containing 100 μg/ml of cycloheximide. The cells were incubated for 1 h at 25° C., NaN₃ was added, the cells were pelleted and the supernatant removed as above. Both cell samples were lyzed mechanically with glass beads, and the lysates were reconstituted with NET-buffer to 400 μl. 200 μl samples of supernatants and cell lysates were diluted with one volume of NET-buffer (0.05 M Tris-HCl pH 8.0, 5 mM EDTA, 0.4M NaCl, 100 U/ml aprotinin, 1% NP-40), 8 μl of 100 mM phenyl methyl sulphonylfluoride and 4 μl of anti-hsp150 antiserum was added. The samples were incubated for 90 min in the cold (4° C.) in rotation, 100 μl of 5% protein-A-Sepharose (Pharmacia) was added and the incubation continued for 90 min. The Sepharose beads were pelleted and washed twice with NET-buffer diluted with one volume of water, then twice with wash buffer (0.1M Tris-HCl pH 7.5, 0.2M NaCl, 2M urea, 0.5 % Tween-20), then with 1% β-mercaptoethanol and finally with 0.1% SDS.

The immunoprecipitated $^{35}$S-proteins were analyzed with SDS-polyacrylamide gel electrophoresis and autoradiography. The immunoprecipitation experiments showed that in the H1 strain, about 90% of labeled hsp150 protein was secreted to the growth medium and the rest remained cell-associated and had the mature size. During the chase in the presence of cycloheximide, the cells secreted less than 10% of the amount of hsp150 secreted during labeling. When the labeling was performed at 25° C., the majority of hsp150 was again secreted, but the total amount of radiolabeled hsp150 was about 8-fold lower than that labeled at 37° C. Similar results were obtained with the H3 strain, showing that hsp150 was secreted under restrictive conditions in the sec7 strain similarly as in the wild type strain. Even a kex2 mutant (strain H269) secreted hsp150, according to immunoprecipitation experiments.

Disruption of the HSP150 Gene

To be able to study the regulation and expression of the HSP150 gene modified by gene technology, the chromosomal HSP150 gene of S. cerevisiae was disrupted (Rothstein, Meth. Enzymol. 194:281–301, 1991). The HSP150 gene was transferred as a SalI fragment of about 4.3 kb from pKTH4508 (FIG. 5) to the Bluescript SK⁺ vector, from which the PstI site had been removed. The HSP150 gene has two PstI sites, one of them in the region encoding subunit I and the other downstream from the sequence encoding the repetitive region of subunit II. The PstI fragment of 721 base pairs from the middle of HSP150 was removed with PstI digestion, the fragments were separated in agarose gel electrophoresis. The ends of the single-stranded fragment isolated from the gel were converted blunt ended with T4 DNA polymerase (Sambrook et al., Molecular Cloning, 1989). The URA3 gene was then ligated to this plasmid as a HindIII fragment of about 1000 base pairs, converted blunt ended with T4 DNA polymerase. The URA3 gene of the new plasmid (pKTH4510, FIG. 6) was flanked at the 5'-end with about 2500 base pairs, and at the 3'-end with about 900 base pairs of yeast chromosomal DNA. pKTH4510 was transformed into the diploid S. cerevisiae strain H246, where the plasmid borne disrupted HSP150 replaced the single HSP150 allele by homologous recombination. Uracil prototrophes were selected amongst the transformants and sporulated. Tetrad analysis showed that all URA+ spores were able to form colonies, indicating that the HSP150 gene is not essential for viability. Absence of the intact HSP150 in the disruptants was demonstrated by Southern hybridization, and the absence of correct HSP150 mRNA by Northern analysis (Sambrook et al., Molecular Cloning, 19898). One strain with a disrupted HSP150 gene was named H23. The HSP150 gene was disrupted also from the haploid strain H3. This disruptant was called H275.

Secretion of plasmid-expressed hsp150

The HSP150 gene was transferred in a plasmid to a HSP150-disruptant in the following way. The same 4.3 kbSalI fragment which contained the intact HSP150 gene and was used above for gene disruption, was transferred to the multilinker region of pRS414 (FIG. 7A; Sikorski and Hieter, Genetics 122:19–22, 1989). The new plasmid was denoted pKTH4530 (FIG. 7B). Because the vector contains the ARS sequence for autonomous replication, and the CEN region, the plasmid is relatively stable and occurs as a single copy in the transformant. pKTH4530 was transformed into strain H275, and the transformants were selected by tryptophane prototrophy. The new transformant was named H284. Northern analysis, using HSP150 cDNA as a probe, showed that transcription of the plasmid borne HSP150 gene was similarly heat regulated as the chromosomal gene. Strain H284 was metabolically labeled with $^{35}$S-methionine at 37° C., and the supernatant and cell lysate were analyzed by immunoprecipitation, as described above. Even the H284 strain secreted more than 80% of hsp150 protein into the YPD-medium. Note that the strain H284 harbors the sec7 mutation. Thus, this example shows that, firstly, plasmid-born hsp150 was expressed in a heat-regulated manner, and, secondly, it was secreted in spite of the sec7 mutation to the medium at 37° C.

EXAMPLE 2

Fusion of *Escherichia coli* TEM β-Lactamase Gene with Fragments of the HSP150 Gene, and the Expression of Respective Fusion Proteins in *S. cerevisiae*

Construction of HSP150-bla Fusions

β-Lactamase of *E. coli* is encoded by the bla gene, and has a signal peptide which takes it to the periplasm of *E. coli* (Sutcliffe, PNAS 75:3737–3741, 1978). When expressed in *S. cerevisiae* from its authentic structural gene, 90% of it remains cell-associated, and 10% is transported to the cell wall (Roggenkamp et al., J. Biol. Chem. 260:1508–1512, 1985).

The *E. coli* bla gene, without the signal sequence, was fused to the 3'-end of different fragments of the HSP150 gene. In each fusion, the upstream flanking region consisted of more than 2000 base pairs of the HSP150 promoter region, and 184 base pairs (SalI-PstI fusion), 962 base pairs (SalI-KpnI fusion) or 1226 base pairs (SalI-ClaI fusion) of the HSP150 structural gene. Thus, all fusions had the signal sequence of HSP150. In addition, there were 45 codons from the 54 codons of subunit I in the SalI-PstI fusion. The SalI-KpnI fusion had all codons of subunit I plus the 249 first codons of subunit II, which encode the entire repetitive random coil region. SalI-ClaI fusion lacked only the 4 last codons of HSP150 (FIGS. 3A–3D).

The HSP150 fusions were constructed in the pKTH4505 plasmid (FIG. 8), where the SalI-ClaI fragment of the genomic clone pKTH4508 had been transferred to the Bluescript SK⁻ vector. Since the transcription termination signals of HSP150 were missing in the pKTH4505 plasmid, the *S. cerevisiae* alcohol dehydrogenase terminator (ADH-TERM.) was ligated downstream from the ClaI site. The terminator was removed from pAAH5 (Ammerer, Meth. Enzymol. 101:192–201, 1983) as a 450 base pair HindIII-BamHI fragment, and ligated between the HindIII and BamHI sites of pKTH4505 (FIG. 8). Those restriction sites are downstream from the ClaI site. The resulting plasmid was named pKTH4529 (FIG. 8).

The pKTH4529 plasmid had to be modified further for the bla fusions, since the bla gene had been decided to be fused to the KpnI site of HSP150, and there was another KpnI site in the multilinker region of the vector. The latter KpnI site was removed as follows. pKTH4529 was linearized with SalI digestion. The DNA was hydrolyzed from both free ends with Bal31 nuclease (Promega) as follows: 3.5 µg of linearized pKTH4529 was incubated with Ba131 (0.25 U) at 30° C. in 20 mM Tris-HCl pH 8.0, containing 0.6M NaCl, 12 mM CaCl$_2$, 12 mM MgCl$_2$ and 10 mM EDTA, in a total volume of 60 µl. Samples of 20 µl were withdrawn at 10, 15 and 20 min time points, and the reaction was stopped by adding 5 µl of 100 mM EDTA and transferring the samples on ice. Bal31 was inactivated by heating at 65° C. for 15 min, whereafter the nuclease was removed from the samples by phenol extraction, and the DNA was concentrated by ethanol precipitation. Prior to phenol extraction, 2 µl samples were analyzed on agarose gels to estimate the extent of the nuclease digestion. The ends of the DNA molecules were converted blunt ended with Klenow enzyme (Sambrook et al., Molecular Cloning, 1989), and a BamHI linker of 8 base pairs was ligated to the ends. The molar ratio of vector and linker was 1:2, and the total amount of vector was 100 ng.

The ligation mixture was transformed to *E. coli* XL-1 Blue (Stratagene), and the transformants were selected on ampicillin plates (100 µg/ml). DNA was extracted from 40 transformants using the alkaline lysis method (Sambrook et al., Molecular Cloning, 1989). BamHI and KpnI digestions were used to screen for transformants which had obtained the BankHi linker and had lost the KpnI site of the multilinker region. Three plasmids were found which had only one KpnI site, the one within the HSP150 gene, and two BankHi sites. They were subjected to BamHI-EcoRV digestion to estimate the amount of DNA digested by Bal31 nuclease. One plasmid was chosen where about 100 base pairs to the direction of the HSP150 gene had been removed, and it was named pKTH4536 (FIG. 9). The genomic SalI fragment of HSP150 contained 276 base pairs of pBR322 sequence (the BamHI/Sau3AI-SalI fragment of the tetracyclin resistance gene) which originated from the gene bank from which HSP150 had been cloned. Removal of part of the pBR322 borne sequence was advantageous, because the vector in which the HSP150-bla fusions were to be transformed into yeast had the same pBR322 borne sequence. Now plasmid pKTH4536 was ready for fusion with the bla gene.

Since there is no convenient restriction site in the bla gene between the sequences encoding the signal peptide and the mature enzyme, the bla gene was synthesized in vitro with the polymerase chain reaction (PCR, Sambrook et al., Molecular Cloning, 1989). Thus, the bla sequence coding for the mature enzyme was synthesized, and in frame restriction sites for PstI, KpnI and ClaI were created upstream from the bla sequence. DNA fragments can be multiplied by PCR, provided that the sequences of both ends are known. Oligonucleotides (primers) are synthesized according to both ends of the fragment to be multiplied. The primers may contain changes, or incorporate new restriction sites. The template DNA is denatured to separate the strands. The primers are allowed to anneal to their complementary sequences on the template. DNA polymerase then synthesizes, starting from the primers, the DNA strands according to the template. Temperature-resistant polymerases are used in PCR, so that denaturation, the annealing of the primers, and synthesis can be repeated without adding more enzyme between the cycles.

The β-lactamase gene was synthesized using 5 ng of pUC8 plasmid, which had been linearized at the EcoRI site of the multilinker region. The β-lactamase gene encoded by pUC8 has the advantage, as compared to the original β-lactamase gene, that its PstI site has been destroyed, facilitating the construction of the HSP150-bla fusions. Primer 91683 was used in the 5'-end to obtain suitable bla fragments to be ligated to the KpnI and ClaI sites of HSP150 in the correct reading frame. Primer 2659 was used to obtain a suitable fragment for the PstI site. Primer 91684 was used for the 3'-end of all constructions (Table 1). Primer 91683 had 42 nucleotides and its melting temperature is 56° C. Primer 91684 had 32 nucleotides with a melting temperature of 54° C., and primer 2659 30 nucleotides with a melting temperature of 58° C. Primer 91683 was used to create the ClaI, KpnI and PstI sites, in this order, to the 5'-end of the bla gene. Primer 2659 created a PstI recognition site to the 5'-end of the bla gene. Primer 91684 created a HindIII site to the 3'-end of the bla fragments. 2.5 U of the Pfu-DNA polymerase of *Pyrococcus furiosus* (Stratagene) was used in PCR. The concentration of the primers was 1 μm and that of the deoxyribonucleotides was 200 μM, in a total volume of 50 μl. Buffer 1, recommended by Stratagene for DNA fragments which exceed 500 nucleotides, was used. The DNA was multiplied in 30 cycles. Denaturation was for 1 min at 94° C., annealing for 1 min at 51° C., and DNA synthesis for 2 min at 72° C. PCR yielded fragments of expected sizes, 845 base pairs and 836 base pairs, which were digested for the PstI fusion with PstI and HindIII, for the KpnI fusion with KpnI and HindIII, and for the ClaI fusion with ClaI and HindIII.

Fusion of the bla gene to the HSP150-fragments was performed as follows. pKTH4536 was digested with PstI and HindIII for the PstI fusion, with KpnI and HindIII for the KpnI fusion, and with ClaI and HindIII for the ClaI fusion. In the case of the KpnI and PstI fusions, agarose gel electrophoresis was used to separate the vector from the HSP150 fragment, which was to be replaced by the bla gene. The vector portion was isolated from the gel and purified. In the ClaI fusion, the ClaI and HindIII sites are close to each other, without a fragment to be separated in between. The bla gene, synthesized by PCR and digested appropriately, was ligated to the different vector portions of plasmid pKTH4536, prepared as described above. The ligation mixtures were transformed to *E. coli* DH5α (GIBCO BRL), and grown on ampicillin plates. The clones with the insertions were screened from the transformants as follows. Bacteria grown overnight were suspended in 50 μl of GET-medium (25mMTris-HCl pH 8.0, 10 mM EDTA, 0.5% glucose), the cells were disrupted with 5 μl of SDS-NaOH-EDTA (5% SDS, 500 mM NaOH, 50 mM EDTA), and incubated for 30 min at 68° C. 6 μl of glycerol, containing 10mMTris-HCl pH 8.0, 10mM EDTA, 0.1% SDS and 0.2% bromphenol blue, was added and 25 μl samples were resolved on 0.8% agarose gels. The plasmid DNA of the transformants with inserts was isolated and subjected to restriction enzyme analysis. Positive clones were named as follows: pKTH4538=PstI fusion (FIG. 10), pKTH4539=KpnI fusion (FIG. 11) and pKTH4540 =ClaI fusion (FIG. 12).

In these plasmids, the bla gene occurs as two copies, as a selection marker for *E. coli* and in the HSP150-bla fusions. Since the host *E. coli* strain is recA, the bla genes will not easily recombine with each other. However, since such yeast strains are not available, the fusions were transferred in the following way to the vector pKTH4542 containing the tetracyclin resistance gene TET of pBR322 as a selection marker (FIG. 13). The HSP150-bla fusions were removed from plasmids pKTH4538, pKTH4539 and pKTH4540 as BamHI-fragments of about 4000, 4700 and 5000 base pairs, respectively. The ends of the fragments were converted blunt ended with Klenow enzyme. Plasmids pKTH4543 (FIG. 14), pKTH4544 (FIG. 15) and pKTH4545 (FIG. 16) do not replicate in yeast. Thus, the 2241 base pair 2μ-replicon from plasmid YEp24 was transferred as an EcoRI fragment to the EcoRI site of plasmids pKTH4544 and pKTH4545, to yield plasmids pKTH4547 (FIG. 17) and pKTH4548 (FIG. 18), respectively. These were transformed into *E. coli* DH5α and transformants with inserts were screened for. Their plasmids were confirmed to be correct by restriction enzyme analysis, and the plasmids were transformed to *S. cerevisiae* strains H1 and H3 with electroporation. Transformants were selected by uracil prototrophy. The H1 strain transformed with plasmid pKTH4548 was named H329, and that transformed with pKTH4547 was named H331.

To integrate the fusion genes into the yeast genome, plasmids pKTH4543 (FIG. 14), pKTH4544 (FIG. 15) and pKTH4545 (FIG. 16) were linearized at the NcoI site of the URA3 gene, and transformed into strain H1. Transformants were selected by uracil prototrophy. H1 transformed with plasmids pKTH4543, pKTH4544 and pKTH4545 were named H333, H335 and H337, respectively. Southern blotting showed that each strain contained a single integrated HSP150-bla fusion gene.

Expression of the Fusion Genes at the Transcriptional Level

Northern analysis, perfomed as described above, using HSP150 cDNA PstI-fragment and PCR-prepared bla gene (primers 91683 and 91684) as probes, showed that H333, H335 and H337 produced mRNA molecules which hybridized with the bla probe, and that mRNA of H335 and H337 hybridized also with the HSP150 probe. The hybridizable mRNAs had the expected sizes of about 1.3 kb, 1.8 kb and 2.4 kb, respectively. Incubation of the cells, grown at 24° C. in YPD-medium, for 30 min at 37° C. prior to extraction of the RNA and Northern analysis showed that the expression of the hybrid mRNA molecules was activatd by heat shock.

Expression and Secretion of hsp150-β-Lactamase Fusion Proteins

The expression of the HSP150-bla fusion genes in strains H239, H331, H333, H335 and H337 were examined using the chromogenic substrate nitrocefin, which is hydrolyzed by β-lactamase to a red product (Simons et al., J. Mol. Biol. 126:673–690, 1978). Colonies of transformants, grown on selective plates, were resuspended in selective medium (2×10$^8$ cells/400 μl), and incubated for 1 h at 37° C. When nitrocefin was added to the media from which the cells had been removed by centrifugation, they turned red, indicating that the transformants secreted a novel protein which had β-lactamase activity. The parental strain H1 did not produce any chromophore from nitrocefin.

Secretion of novel fusion proteins in strains H333, H335 and H337 was studied as follows. The strains were grown in YPD-medium at 24° C. to A$_{600}$ of 1–2. Then, 2×10$^8$ cells were separated from the media by centrifugation, resuspended in 400 μl of YPD-medium, and incubated for 60 min at 37° C. The growth media were separated from the cells and the cells were lysed with glass beads as described in Example 1. The cell lysates and medium samples (40–80 μl) were analyzed by Western blotting using anti-hsp150 antiserum against subunit II (1:1500) and anti-β-lactamase antiserum (1:1000). The H335 strain secreted to the growth medium large amounts of a protein of about 140 kD, immunoreactive with both antisera. It was named hsp150 (KpnI)-β-lactamase. Much less of hsp150(KpnI)-β-lactamase or other immunoreactive material was detected from the cell lysate. Strain H337 secrete very little of a 145 kD protein which reacted with both antisera (hsp150(ClaI) -β-lactamase). Most of immunoreactive material of H337 was found from the cell lysate. Similar results as for H337 were obtained for strain H333, except that the apparent molecular weight of the secreted protein, hsp150(PstI)-μ-lactamase, was about 48 kD, and that all extra- and intracellular proteins reacted only with anti-μ-lactamase antiserum.

H333, H335 and H337 strains were labeled metabolically with 100 μCi/ml of $^{35}$S-methionine for 1 h at 37° C., and subjected to immunoprecipitations with anti-hsp150 antiserum and anti-β-lactamase antiserum, as described in Example 1. In the case of H335, the supernatant contained a hsp150-β-lactamase fusion protein of about 130 kD. About 10% of the de novo synthesized protein could be precipitated from the lysate, and it comigrated mostly with the secreted hsp150(KpnI)-β-lactamase. In the case of H333 and H337, very little of de novo $^{35}$S-fusion protein of about 48 kD and 145 kD, respectively, were detected from the growth media, as compared to H335. Most of the immunoprecipitated labeled protein was cell-associated, it was heterogenous in size and smaller than the respective secreted protein. The proteins immunoprecipitated from H333 reacted only with anti-β-lactamase antiserum.

For measurements of β-lactamase activities of the fusion proteins, H333, H335 and H337 were grown at 24° C. like above, resuspended in fresh YPD-medium, and incubated for 3 h at 24° C. or 37° C. Secreted activity was determined by assaying growth medium samples directly. Cell wall-trapped activity was measured from washed cell suspensions, since nitrocefin does not penetrate the yeast plasma membrane. Activities associated with the cell wall plus intracellular compartments were assayed from whole cell lysates which were prepared as described in Example 1 for immunoprecipitations, except that the lysis mixtures were not heated and no SDS was added to them. H335 secreted about 700 U/ml of β-lactamase activity to the medium in 3 h at 37° C. About 120 U/ml and 20 U/ml were found in the cell wall and intracellular compartments, respectively. At 24° C., about 130 U/ml was secreted in 3 h, and very little remained cell-associated. In the case of H333 and H337, less than 50 U/ml and 100 U/ml was secreted, respectively, and about the same amounts remained cell-associated. There was a linear increase of β-lactamase activity in the growth medium of H335 for at least 6 h at 37° C., showing that heat-activation of the expression was not transient. When wild type cells were shifted from 24° C. to 37° C., there was a 14-fold increase in the level of newly synthesized hsp150 protein within 15 min, however, thereafter the level of activation started to decline, indicating that heat-activation of the hsp150 expression was transient.

When H335 was grown overnight at 24° C. to $A_{600}$ of 1, and incubated thereafter at 37° C. to stationary phase ($A_{600}$ about 30), β-lactamase activity was secreted as long as the cells grew, and the activity was about 12000 U/ml when the cells reached stationary phase. The same activity persisted for 50 more hours. Coomassie blue staining of supernatant samples showed that the hsp150(KpnI)-β-lactamase fusion protein was the most abundant protein in the growth medium.

H335 grew with the same generation time as its parental strain H1, whereas that of H333 was twice as long as that of H1. The fusion gene in H335 seemed to remain stable in the chromosome. During growth in YPD-medium up to stationary phase, all cells retained the ability to secrete β-lactamase activity, as determined by the nitrocefin assay.

Thus, Example 2 shows that hsp150(KpnI)-β-lactamase, where β-lactamase was preceded by the signal sequence, subunit I and the repetitive random coil region of the hsp150 protein, was efficiently expressed in a heat-activated manner. The random coil region of hsp150 subunit II apparently did not interfere, not at least severely, with the folding of the β-lactamase portion since an enzymatically active fusion protein was produced. The fusion protein was compatible with the secretion machinery of S. cerevisiae, and was efficiently secreted to the growth medium. Contrary to the authentic hsp150, heat-regulation in strain H335 was not transient but persisted for tens of hours.

EXAMPLE 3

Fusion of the Human Insulin Gene with the HSP150 Gene and Expression of the Fusion Gene in S. cerevisiae Since the hsp150(Kpn)-β-lactamase fusion protein containing the random coil region of hsp150 subunit II and lacking its C-terminal portion (FIGS. 3A–3D) was efficiently expressed and secreted, we chose to join the human insulin protein, without its signal sequence, to this hsp150-fragment. The hsp150-insulin fusion protein was expressed either as a fusion where the hsp150 carrier was joined directly to the N-terminus of mature insulin, or as a fusion, where a kex2 recognition site was engineered between the hsp150 carrier and mature insulin.

Fusion of the HSP150 Gene with the Human Insulin cDNA

The human insulin cDNA was fused to plasmid pKTH4539 (FIG. 11). The insulin cDNA was synthesized with PCR (Mullis and Faloona, Meth. Enzymol. 155: 335–350, 1987), using a circular pchiI-19 plasmid (obtained from Dr. Graeme Bell, Howard Hughes Medical institute Research Laboratories) as a template. The plasmid contains a 500 base pair human insulin cDNA, part of whose terminator region has been ligated as an EcoRI fragment to the pBR328 vector. The PCR product was a 261 base pair insulin cDNA fragment, lacking the signal sequence. The primer for the 3'-end (2698; Table 1) consists of 20 nucleotides complementary to the insulin cDNA sequence starting from position 330, followed by a HindIII recognition site. The 5'-primers were 2697 or 2699 (Table 1), consisting both of 20 nucleotides according to the insulin cDNA sequence starting at position 73, both having an Asp718I recognition site at the 5'-end (Asp718I recognizes the same sequence as KpnI). Primer 2699 contains also an AAGAGA sequence to code for Lys-Arg, a recognition site for the kex2 protease.

PCR was performed in a volume of 50 μl using 5 ng of plasmid DNA and 50 pmol of both primers. The concentration of the deoxyribonucleotides were 200 μM, and 2.5 U of pfu-polymerase (Stratagene) was used in buffer #3 of Stratagene. 25 μl of mineral oil was added to prevent vaporization. The DNA was amplified for 25 cycles with a Techne PHC-2 instrument as follows: denaturation at 94° C. for 1 min, annealing at 55° C. for 30 sec and DNA polymerization at 72° C. for 1 min. The amplified DNA fragments of 261 base pairs were isolated by agarose gel electrophoresis and digested with Asp718I and HindIII.

The bla fragment was removed from plasmid pKTH4539 (FIG. 11) with Asp718I and HindIII, and replaced by the above insulin DNA fragments. The ligation was performed according to Sambrook et al., 1989 in 10 µl for 12 h at 16° C. 5 µl of the ligation mixture was transformed to *E. coli* DH5α and transformants were selected on ampicillin (100 µg/ml) plates. Plasmid DNA was isolated from transformants according to Holmes and Quigley (Anal. Biochem. 114:193–197, 1981), and digested with Asp718i and HindIII to screen for insertions. The correct plasmids were named pKTH4581 (FIG. 19) and pKTH4582 (FIG. 20). The latter contains a Lys-Arg encoding linker between the HSP150 and insulin sequences. The nucleotide sequence of insulin-cDNA was confirmed to be correct by sequencing, using as primers oligonucleotide MS2 (starts at position +902 of the HSP150 gene), and MS4 (proceeds upstream from position +1778 of the ADC1 gene (Table 1).

Transformation of *S. cerevisiae* with HSP150-insulin cDNA-fusions.

The HSP150-insulin cDNA fusions were then ligated to the yeast integrative vector. Plasmid pFL35 (Bonneaud et al., Yeast 7:609–615, 1991) was used as an integratire vector, containing the 843 base pair TRP1 marker for selection in yeast. Selection in *E. coli* was performed according to ampicillin resistance and α-complementation of β-galactosidase. The pFL35 vector was linearized with BamHI, isolated in agarose gel electrophoresis, and treated with alkaline phosphatase according to manufacturer's instructions (CIP, Boehringer Mannheim). The plasmids pKTH4581 and pKTH4582 were digested with BamHI, and HSP150-insulin cDNA fragments of about 4200 base pairs were isolated in agarose gel electrophoresis. These fragments were ligated to the pFL35 vector, which were then transformed to *E. coli* DH5α. Transformants were selected on ampicillin plates containing 40 µg/ml of X-Gal and 12 µg/ml of IPTG. Plasmid DNA from white colonies was isolated for restriction analysis with BamHI. The DNA from plasmids containing the right insert was digested with EcoRV to determine the orientation of the insert. Plasmids obtained in this way were named pKTH4583 (FIG. 21) and pKTH4584 (FIG. 22). The latter plasmid has the Lys-Arg encoding sequence between the HSP150 and the insulin DNA sequences.

To transform the *S. cerevisiae* strain H23 (Table 2) with the lithium acetate method, about 7 µg of plasmids pKTH4583 and pKTH4584 were linearized with Bsu36I which cuts the TRP1 gene. Transformants were screened according to tryptophane prototrophy and grown in YPD-medium for chromosomal DNA isolation. The DNA was then digested with EcoRV and subjected to Southern analysis (Sambrook et al., 1989), using a radiolabeled insulin cDNA fragment of 261 base pairs as a probe. Strain H23 transformed with plasmid pKTH4583 was named H398 and strain H23 transformed with plasmid pKTH4584 was named H412 (Table 2).

Expression of Hybrid mRNA Molecules

Strains H398 and H412 were grown overnight in YPD-medium to $A_{600}$ of 1 at 24° C. and subjected to RNA extraction and Northern blot analysis using the HSP150 cDNA PstI-fragment and the above 261 bp insulin cDNA-fragment as probes. The results showed that mRNA molecules hybridizing with both probes were produced in both strains. Incubation of the cells for 30 min at 37° C. prior to RNA extraction increased the expression of the hybrid mRNA.

Expression and Secretion of hsp150-Insulin Fusion Proteins

Strains H398 and H412 were grown overnight at 24° C. to $A_{600}$ of about 1, and $2 \times 10^8$ cells were pelleted and resuspended in fresh YPD-medium and incubated at 37° C. for 60 min. Growth media samples (80 µl) and cell lysate samples of respective size were subjected to Western blot analysis using anti-hsp150 antiserum against subunit II, and monoclonal antibodies (Novo Nordisk) against human insulin B-chain (HUI-001), C-peptide (PEP-001) and A-chain (HUI-018). The analysis revealed a fusion protein in the growth media of both strains of the apparent molecular weight of roughly 140 kD, which reacted with all four antibodies. The lysate samples contained a similar protein, the amount of which was approximately the same as that of the secreted protein. Thus, a hsp150-insulin fusion protein, containing A- and B-chains plus C-peptide, was expressed and secreted to the medium. Whether in part of the expressed fusion protein the cleavage sites between the B-chain, C-peptide and A-chain were processed in strain H398 is not known, since in the above Western blot analysis, released A-chains, B-chains and C-peptide would be lost in the blotting procedure due to their small size. In strain H412 the amount of extracellular and intracellular immunoreactive protein was smaller than in strain H399, suggesting that cleavage reactions at kex2 sites occured more frequently than in strain H398.

Strain H398 was metabolically labeled with Tran-$^{35}$S (Amersham), and the growth medum and cell lysate samples were subjected to immunoprecipitation with anti-hsp150 antiserum and anti-C peptide monoclonal antibody (1:100), as described in Example 2 for H333, H335 and H337. SDS-PAGE and autoradiography showed that the medium sample and the cell lysate sample contained only one band. Both were precipitated with both antibody preparations, and had the apparent molecular weight of about 140 kD. About 60–75% of the radiolabeled fusion protein had been secreted to the growth medium.

Strain H398 was grown in YPD-medium at 24° C., and samples were withdrawn till the cell density reached a plateau at about $A_{600}$ of 10. The 500 µl-samples were lyophilized and resolved on SDS-PAGE. Coomassie blue staining of the gel showed that the hsp150-insulin fusion protein was the most abundant protein secreted by the transformant.

Example 3 shows that human insulin can be secreted to the growth medium of *S. cerevisiae* using the random coil fragment of hsp150 as a carrier.

EXAMPLE 4

Construction of Fusion Genes Containing HSP150 and Neurotrophic Factor Genes

BDNF (brain derived neurotrophic factor) and NT-3 (neurotrophin 3) are secretory neurotrophic factors that are synthesized as preproproteins. The pre-portion is a signal peptide that leads the proteins to the secretory pathway. The pro-portion is cleaved off from the mature portion in the authentic host cells in the Golgi by a kex2-like protease. The function of the pro-portion is unknown, but it may be important for the proper folding of the proteins. Since it is not known whether the pro-regions are required for the activation and folding of the neurotrophins, they were fused to the hsp150 protein both with their pro-regions (pro forms) and without their pro-regions (mature forms).

Synthesis of the neurotrophic factor genes by PCR

The BDNF and NT-3 genes were cloned and sequenced from a rat hippocampus cDNA library by Dr. Mart Saarma (Institute of Biotechnology, University of Helsinki, Finland). We used these cDNA clones as templates in PCR to synthesize suitable gene fragments to be fused to the KpnI site of HSP150.

The pro forms and mature forms of BDNF and NT-3 were synthesized in the following way.

1) For proBDNF primer 2258 was used for the 5'-end and primer 91749 for the 3' end (Table 1). Primer 2258 starts from codon 16 of the proBDNF structural gene, which is supposed to be at the end of the signal sequence. The cleavage site of the BDNF signal peptide is not known. The 16th codon is preceded by a KpnI recognition site. Primer 91749 contains sequences from the 3' end of the BDNF gene, its stop codon and a HindIII recognition site.

2) For mature BDNF the 5' primer was 2259 (Table 1) and the 3' primer was the same as that for the proBDNF (91749). Primer 2259 contains a KpnI recognition site followed by the 4 last codons of the pro-region, which contain a kex2 recognition site, and 5 bp from sequences coding for the mature portion of BDNF. The melting temperature of all BDNF primers is 54° C. The template used was BDNF cDNA as a BamHI fragment in Bluescript SK$^+$. The plasmid was digested with BamHI before the PCR reactions.

3) For proNT-3 the 5' primer was 2260 and the 3' primer was 2261 (Table 1). Primer 2260 contains a KpnI site and immediately downstream of it the 19th codon of the NT-3 structural gene, which is at the putative signal sequence cleavage site. Again, the cleavage site is not known. The melting temperature of 2260 is 52° C. Primer 2261 contains sequences from the 3' end of the NT-3 gene, its stop codon and 6 codons downstream of it, and a recognition site for HindIII, and its melting temperature is 54° C.

4) For mature NT-3 the 5' primer was 2262 (Table 1) and the 3' primer was the same as that for the proNT-3 (2261). The 5' primer contains a KpnI recognition site followed by the 4 last codons of the pro-region, which contains a kex2 recognition site. This is followed by the 7 first nucleotides coding for the mature portion of NT-3. The melting temperature of 2262 is 56° C. The template was NT-3 cDNA in Bluescript KS$^+$, which was linearized with HindIII.

The PCR reactions were performed in a volume of 50 μl. The amount of the template was 2 ng, the concentration of primers was 1 μM, and that of the nucleotides was 200 2.5U of pfu-polymerase (Stratagene) was used per reaction. The proforms were synthesized in buffer #1 and the mature forms in buffer #2 provided by Stratagene. Denaturation was performed at 94° C. for 1 min, annealing at 51° C. for 2 min, and elongation at 72° C. for 1.5 min. The cycle was repeated 30 times in a DNA Thermal Cycler (Perkin Elmer Cetus). The products of PCR were of expected sizes as judged in an agarose gel: ProBDNF 726 bp, mature BDNF 392 bp, proNT-3 750 bp, and mature NT-3 397 bp. The fragments were purified by phenol extraction and ethanol precipitation, and digested with KpnI and HindIII. The fragments were ligated to the larger portion of pKTH4536 (FIG. 9), which had been digested with KpnI and HindIII and purified in an agarose gel. The ligation mixtures were used to transform E. coli DH5α, and the transformants were selected on L-ampicillin plates. The plasmids of apparently correct size were analysed by XhoI-HindIII digestion. By PCR it was confirmed that the plasmids indeed contained the desired insert. The presence of mature NT-3 insert was also confirmed by Southern hybridization. The resulting plasmids are called pKTH4554 (HSP150-proBDNF; FIG. 23), pKTH4555 (HSP150-proNT-3; FIG. 24), pKTH4558 (HSP150-mature BDNF; FIG. 25), and pKTH4578 (HSP150-mature NT-3; FIG. 26). The junctions between HSP150 and the neurotrophic factor sequences were also determined by sequencing.

In plasmids pKTH4554, pKTH4555, pKTH4558, and pKTH4578 the fusion genes are in the Bluescript SK$^-$ vector. The fusion genes were detached from Bluescript by BamHI digestion and the BamHI fragments were purified from an agarose gel. All fragments were ligated to the BamHI-site of YEp24. The presence of an insert was confirmed, and its orientation and correctness was analysed by BamHI, HindIII, and EcoRV digestions. HSP150-proNT-3 fusion and HSP150-BDNF fusion were obtained in both orientations. The new plasmids are pKTH4580 (HSP150-NT-3, FIG. 27); pKTH4585 (FIG. 28) and pKTH4586 (HSP150-proNT-3, FIG. 29); pKTH4589 (FIG. 30) and pKTH4590 (HSP150-BDNF, FIG. 31); and pKTH4591 (HSP150-proBDNF, FIG. 32). These plasmids were transformed to yeast strain H1 by electroporation and transformants were selected by their ability to grow without uracil. The new strains were designated H402 (HSP150-NT-3), H404 (HSP150-proNT-3), H405 (HSP150-proNT-3), H406 (HSP150-BDNF), H407 (HSP150-BDNF) and H408 (HSP150-proBDNF). The strains are listed in Table 2.

The HSP150-BDNF fusion was also ligated to the larger BamHI fragment (10.55 kb) of pAAH5 (FIG. 8; Ammerer, 1983). The insert was obtained in both orientations, and the resulting plasmids are called pKTH4587 (FIG. 33) and pKTH4588 (FIG. 34). These plasmids were transformed to the yeast HSP150-disruptant H23, and transformants were selected by their ability to grow without leucine. The new strains were designated H410 (HSP150-BDNF) and H411 (HSP150-BDNF) (see Table 2).

Expression of HSP150-Neurotrophic Factor Fusion Genes

The expression of the HSP150-NT-3 fusion was studied at the mRNA level by Northern blotting. A PCR-prepared proNT-3 probe hybridized with an mRNA species from strain H402.

Expression at the protein level was studied by analysing the culture medium of strain H404 (HSP150-proNT-3) by Western blotting. Anti-NGF antibody preparation recognized a protein of about 62 kD. Thus, HSP150-neurotrofic factor fusion protein appeared to be expressed and secreted in S. cerevisiae.

TABLE 1

OLIGONUCLEOTIDES AND LINKERS

T8977 (SEQ. ID. NO.: 3)    5' GCI CCI GCI TGI GGI GGI GGI CCG/A TCG/A AAC/T TGG/A AAT/ C TG 91683 (SEQ. ID. NO.: 4)    5' GCT TAT ATC GAT GGT ACC TGC AGT CAC CCA GAA ACG CTG GTG
                                ClaI       KpnI   PstI 91684 (SEQ. ID. NO.: 5)    5' GCA ACC AGG CTT GAG TAA ACT TGG TCT GAC AG
                                   HindIII 2659 (SEQ. ID. NO.: 6)    5' GCT TAT CTG CAG CTC ACC CAG AAA CGC TGG
                                  PstI BamHI linker    5' CGGATCCG 3'
                      3' GCCTAGGC 5'
                           BamHI 2698 (SEQ. ID. NO.: 7)    5' GCG AAG CTT CTA GTT GCA GTA GTT CTC CA
                              HindIII 2697 (SEQ. ID. NO.: 8)    5' GGC CGG TAC CTT TGT GAA CCA ACA CCT GTG
                               KpnI 2699 (SEQ. ID. NO.: 9)    5' GC CGG TAC CAA GAG ATT TGT GAA CCA ACA CCT GTG
                              KpnI

MS4 (SEQ. ID. NO.: 10)    5' ACG TAT CTA CCA ACG ATT TGA C

MS2 (SEQ. ID. NO.: 11)    5' TTC TGC AGC CGC TAC CTC 91749 (SEQ. ID. NO.: 12)    5' CTC CAA GCT TAC TAT CTT CCC CTT TTA ATG G
                                HindIII 2258 (SEQ. ID. NO.: 13)    5' ACA TGG TAC CAT GAA GGC TGC GCC CAT
                               KpnI 2259 (SEQ. ID. NO.: 14)    5' ACA TGG TAC CAG GGT TCG GCG CCA CTC
                               KpnI 2260 (SEQ. ID. NO.: 15)    5' ACA TGG TAC CAA CAA CAT GGA TCA AAG GA
                               KpnI 2261 (SEQ. ID. NO.: 16)    5' ACA TAA GCT TGC CAA TTC ATG TTC TTC CG
                               HindIII 2262 (SEQ. ID. NO.: 17)    5' ACA TGG TAC CCG GAG GAA ACG CTA TGC AG
                               KpnI 9175 (SEQ. ID. NO.: 18)    5' GAC GTA GCC ACA TGC AGC 91604 (SEQ. ID. NO.: 19)    5' GAA TCC TCG AGA TAT AAA AGG AAC ACT AGT TGT CTA ACG ACA ATC
                             XhoI                        SpeI

TABLE 2

SACCHAROMYCES CEREVISIAE STRAINS (H) AND ESCHERICHIA COLI STRAINS (B)

H1 Mata ade2-101 ura3-52 leu2-3, 112 suc2-Δ9 gal2
H3 Mata sec7-1 his4-580 ura3-52 leu2-3,112 trp1-289
H23 Matα his3-11,15 leu2-3,112 trp1-1 ade2-1 ura3-1 can1-100 HSP150::URA3
H246 Mata/α ura3-1 his3-11,15 leu2-3,112 trp1-1 ade2-1 can1-100
H275 Mata sec7-1 his4-580 ura3-52 leu2-3,112 trp1-289 HSP150::URA3
H284 H275 transformed with pKTH4530
H286 H275 transformed with pKTH4535
H314 H275 transformed with pKTH4532
H329 H1 transformed with pKTH4548
H331 H1 transformed with pKTH4547
H333 H1 transformed with pKTH4543
H335 H1 transformed with pKTH4544
H337 H1 transformed with pKTH4545
H398 H23 transformed with pKTH4583
H412 H23 transformed with pKTH4584
H402 H1 transformed with pKTH4580
H404 H1 transformed with pKTH4585
H405 H1 transformed with pKTH4586
H406 H1 transformed with pKTH4589
H407 H1 transformed with pKTH4590
H408 H1 transformed with pKTH4591
H410 H23 transformed with pKTH4587
H411 H23 transformed with pKTH4588
B36 HD5α F⁻ endA1 hsdR17 (R.k.⁻ M.k.⁺) supE44 thi-1 recA1 gyrA96 relA1 fi80d lacZ-δ-M15

B39 XL-1 Blue F'::Tn(Tc$^r$) proA+B+lacI$^R$ del(lacZ)M15/
recA1 endA1 gyrA96(NaI$^R$) Thi hsdR17 (R.k.$^-$ M.k.$^+$)
supE44 relA1 lac

---

I claim:

1. An isolated DNA molecule encoding a secretory hsp 150 protein consisting of:

(a) the DNA sequence of SEQ ID NO: 1; or
   (b) a DNA sequence which encodes an antigenic secretory homolog of hsp150; or
   (c) a DNA sequence which encodes a protein having the amino acid sequence of SEQ ID NO:2 or a functional fragment thereof having at least the N-terminal 321 amino acids of the hsp150 protein; or
   (d) an allelic variant of the sequence of (a) encoding a secretory hsp 150 protein.

2. An isolated DNA molecule encoding a fusion protein of the general, N-terminal to C-terminal, formula S—A—B; or

S—A—L—B;

wherein A is a protein encoded by a DNA molecule according to claim 1 without a signal sequence, B is a heterologous protein, L is a linker, and S is a signal peptide.

3. The DNA sequence according to claim 2 wherein the linker is a polypeptide.

4. The DNA sequence according to claim 3 wherein the linker can be cleaved by a chemical substance or by an intracellular or other protease to release the heterologous protein from the fusion protein.

5. An isolated DNA molecule encoding a peptide consisting of amino acid sequence −18 to −1 of SEQ ID NO: 2.

6. An isolated DNA molecule encoding the repetitive region of the hsp 150 protein, consisting of (a) nucleotides 613 to 1293 of SEQ ID NO:1; or
   (b) a DNA sequence which encodes an antigenie homolog of the repetitive region of the hsp150; or
   (c) a DNA sequence which has degenerate codons with respect to the sequence of (a); wherein said DNA sequence in combination with the signal sequence and subunit I portions of the hsp 150 encoding sequence encodes a secretory protein.

7. A recombinant DNA vector containing the DNA sequence according to claims 1 or 2.

8. The recombinant DNA vector according to claim 7 wherein said DNA sequence is under the control of a promoter allowing its expression in a desired host cell.

9. The recombinant DNA vector according to claim 8 wherein said DNA sequence is under the control of the upstream and downstream regulatory regions of the HSP150 gene.

10. The recombinant DNA vector according to claim 9 wherein the upstream regulatory region comprises at least one heat regulated promoter or a nutrient-responsive promoter.

11. The recombinant DNA vector according to claim 7 which is pKTH4543, pKTH4544, pKTH4545, pKTH4547, pKTH4548, pKTH4584, pKTH4580, pKTE4585, pKTH4586, pKTH4589, pKTH4590, pKTE4591, pKTH4587, pKTH4588, pKTH4535, and pKTH4532.

12. A yeast host containing a recombinant DNA vector according to claim 7.

13. The yeast host according to claim 12 which is *Saccharomyces cerevisiae*.

14. The yeast host according to claim 13 wherein said yeast host is a strain selected from the group consisting of E286 which is E275 transformed with pKTH4535, H314 which is E275 transformed with pKTH4532, E329 which is H1 transformed with pKTH4548, E331 which is H1 transformed with pKTH4547, H333 which is H1 transformed with pKTH4543, H335 which is H1 transformed with pKTE4544, E337 which is H1 transformed with pKTH4545, H398 which is H23 transformed with pKTH4583, H412 which is H23 transformed with pKTE4584, E402 which is H1 transformed with pKTH4580, E404 which is H1 transformed with pKTH4585, E405 which is H1 transformed with pKTH4586, H406 which is H1 transformed with pKTH4589, H407 which is H1 transformed with pKTH4590, H408 which is H1 transformed with pKTH4591, H410 which is H23 transformed with pKTH4587, and H411 which is H23 transformed with pKTH4588.

15. A method for the production of a hsp150 protein or fusion protein comprising the cultivation of a host cell according to claim 12 under conditions appropriate for expression of said DNA sequence and recovering said protein from the culture.

16. An isolated DNA molecule encoding the repetitive region of the hsp 150 protein, consisting of (a) nucleotides 613 to 1293 ofSEQ ID NO:1; or
   (b) a DNA sequence which encodes an antigenic homolog of the repetitive region of the hsp150; or (c) a DNA sequence which has degenerate codons with respect to the sequence of (a); and a functional heterologous protein or a functional fragment of the hsp 150 protein; wherein said DNA molecule, in combination with the signal sequence and subunit I portions of the hsp150 encoding sequence encodes a secretory protein.

17. A method for secreting a heterologous protein or a fusion protein from a yeast which comprises
(a) preparing a recombinant DNA vector comprising the DNA sequence of claim 2 or 16;
(b) transforming a suitable yeast host with said DNA vector;
(c) cultivating said transformed host under conditions appropriate for expression of said DNA sequence; and
(d) recovering said heterologous protein or fusion protein from the culture.

18. The method according to claim 17 wherein the heteroloqous protein to be secreted is selected from the qroup consisting of insulin, bovine derived neurotrophic factor and neurotrophin 3.

19. The method according to claim 17 wherein the host is a wild type yeast or a mutant yeast.

20. The method according to claim 19 wherein the host is Saccharomyces cerevisiae.

21. The method according to claim 20 wherein the host is a sec mutant or kex2 mutant of Saccharomyces cerevisiae.

* * * * *